US012698522B2

(12) United States Patent
White et al.

(10) Patent No.: US 12,698,522 B2
(45) Date of Patent: Aug. 4, 2026

(54) GENOTYPING OF POLYPLOIDS

(71) Applicant: Keygene N.V., Wageningen (NL)

(72) Inventors: Stefan John White, Wageningen (NL);
René Cornelis Josephus Hogers,
Wageningen (NL)

(73) Assignee: Keygene N.V., Wageningen (NL)

( * ) Notice: Subject to any disclaimer, the term of this
patent is extended or adjusted under 35
U.S.C. 154(b) by 959 days.

(21) Appl. No.: 17/402,037

(22) Filed: Aug. 13, 2021

(65) Prior Publication Data

US 2022/0025445 A1     Jan. 27, 2022

Related U.S. Application Data

(63) Continuation of application No.
PCT/EP2020/054676, filed on Feb. 21, 2020.

(30) Foreign Application Priority Data

Feb. 21, 2019     (EP) ..................................... 19158598

(51) Int. Cl.
| | |
|---|---|
| *C12Q 1/6827* | (2018.01) |
| *C12Q 1/6869* | (2018.01) |
| *G16B 20/20* | (2019.01) |
| *G16B 25/20* | (2019.01) |

(52) U.S. Cl.
CPC ......... *C12Q 1/6827* (2013.01); *C12Q 1/6869*
(2013.01); *G16B 20/20* (2019.02); *G16B
25/20* (2019.02)

(58) Field of Classification Search
None
See application file for complete search history.

(56) References Cited

U.S. PATENT DOCUMENTS

2009/0036323 A1 * 2/2009 van Eijk ................. G16B 20/20
506/9

FOREIGN PATENT DOCUMENTS

| | | | |
|---|---|---|---|
| WO | WO-2018136248 A1 * | 7/2018 | ........... C12Q 1/6869 |
| WO | WO-2018/175402 A1 | 9/2018 | |

OTHER PUBLICATIONS

Dirihan et al. Efficient analysis of ploidy levels in plant evolutionary ecology, Caryologia: International Journal of Cytology, Cytosystematics and Cytogenetics, 66:3, 251-256 (Year: 2013).*
Appleby et al. "New technologies for ultra-high throughput genotyping in plants", Methods in Molecular Biology, Plant Genomics, vol. 513 (pp. 19-39), Jan. 2009.
Fu (Yong-Bi) et al., "Genotyping-by-Sequencing and Its Application to Oat Genomic Research", Oat: Methods and Protocols, Methods in Molecular Biology, vol. 1536 (pp. 169-187), 2017.
He et al., "Genotyping-by-sequencing (GBS), an ultimate marker-assisted selection (MAS) tool to accelerate plant breeding", Frontiers in Plant Science, vol. 5, Sep. 30, 2014 (pp. 1-8).
International Search Report and Written Opinion on PCT Appl. Ser. No. PCT/EP2020/054676 dated Apr. 24, 2020 (12 pages).
Kim et al., "Application of genotyping by sequencing technology to a variety of crop breeding programs", Plant Science, vol. 242, Apr. 30, 2015 (pp. 14-22).
MacDonald et al., "A low-cost open-source SNP genotyping platform for association mapping applications", Genome Biology, Biomed Central Ltd., London, GB, vol. 6, No. 12, Dec. 2, 2005 (11 pages).
Rocher et al., "Validation of Genotyping-By-Sequencing Analysis in Populations of Tetraploid Alfalfa by 454 Sequencing", PLOS ONE, vol. 10, No. 6, Jun. 26, 2015 (pp. 1-18).
Scheben et al., "Genotyping-by-sequencing approaches to characterize crop genomes: choosing the right tool for the right application", plant Biotechnology Journal, vol. 15, No. 2, Jan. 24, 2017 (pp. 149-161).
Deschamps S. et al, Genotyping-by-Sequencing in Plants, Biology (Basel) (2012); 1(3): 460-483).
Pel et al., "Rapid and highly-specific generation of targeted DNA sequencing libraries enabled by linking capture probes with universal primers", PLOS One, Dec. 5, 2018, pp. 1-15.

* cited by examiner

*Primary Examiner* — Carla J Myers
(74) *Attorney, Agent, or Firm* — Foley & Lardner LLP

(57)     ABSTRACT

The current invention pertains to a reliable method for determining the relative frequency of a sequence variant of interest in a nucleic acid sample derived from at least one polyploid cell, wherein the method uses a UMI to correct for any amplification biases. The invention further pertains to the use of a UMI for accurately determining the relative frequency of a sequence variant of interest in a nucleic acid sample derived from at least one polyploid cell.

13 Claims, 4 Drawing Sheets

Figures 2A, 2B:
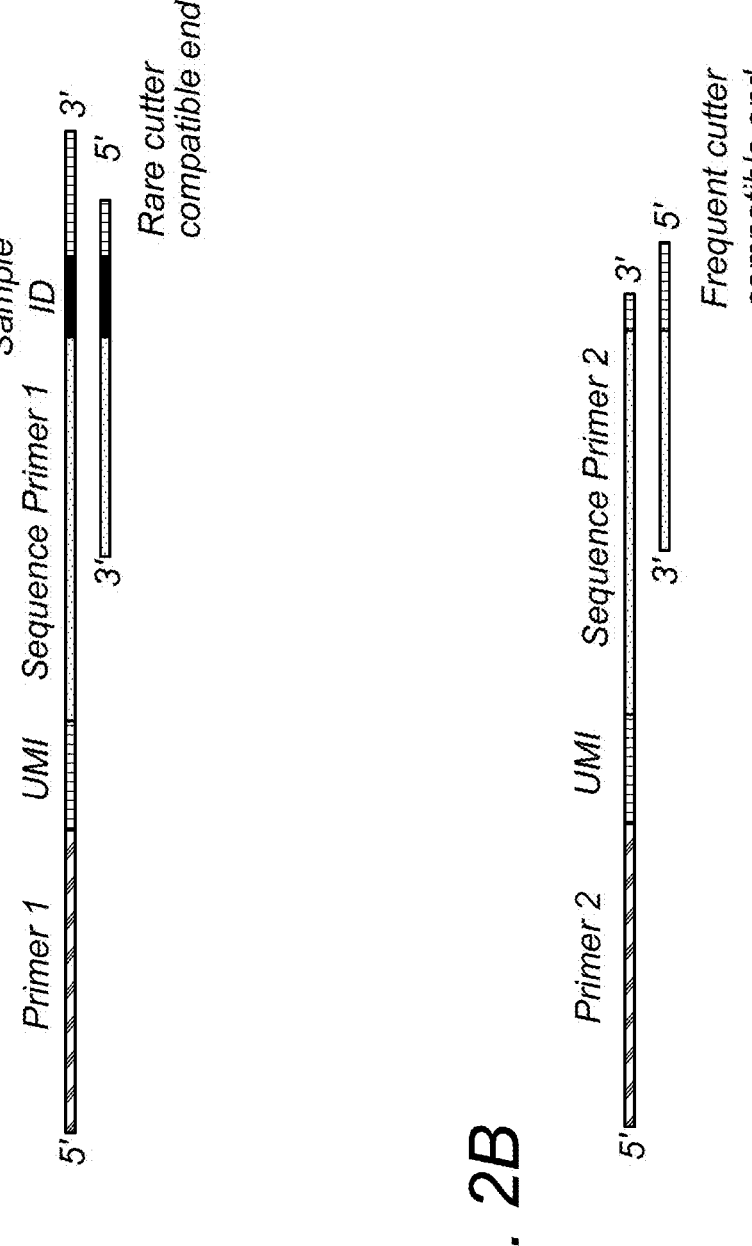

Specification includes a Sequence Listing.

FIG. 1

UMI analysis
Counts plot for locus PZE-101111015

Standard analysis
Counts plot for locus PZE-101111015

Polar coordinates plot for locus PZE-101111015

Polar coordinates plot for locus PZE-101111015

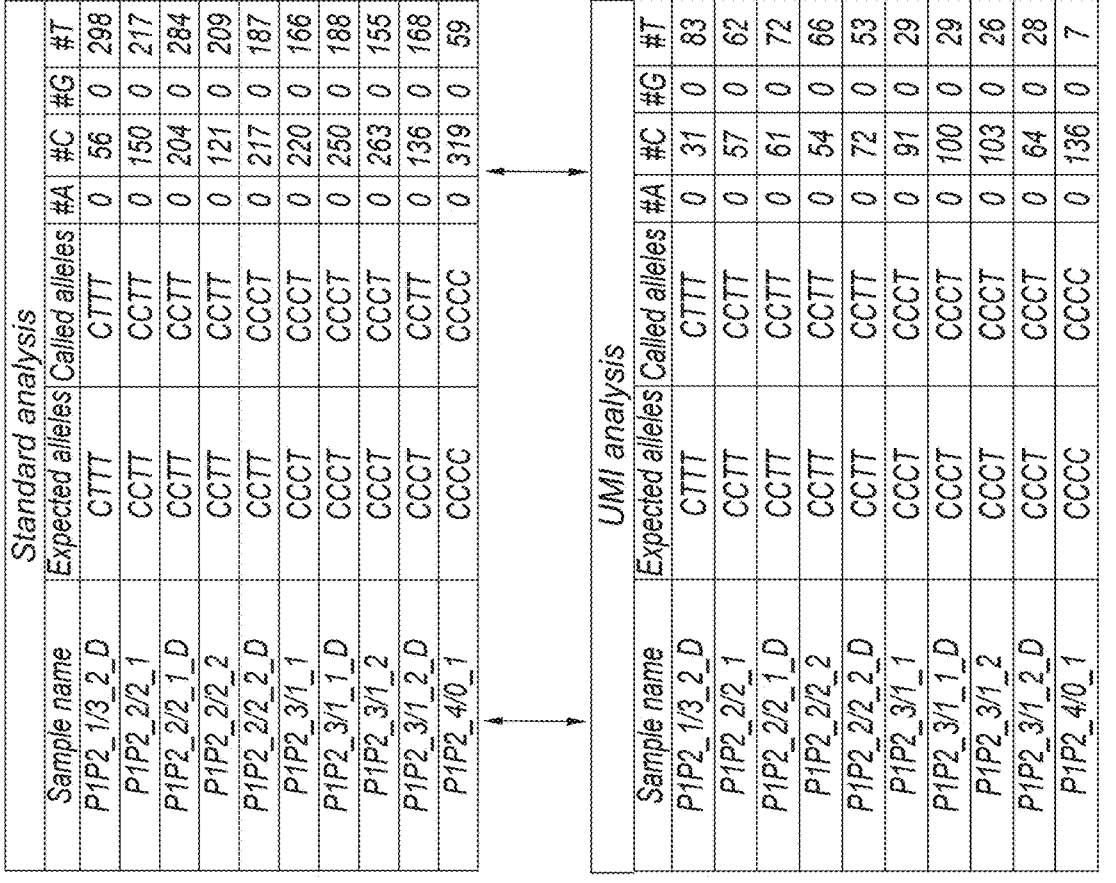

Standard analysis

| Sample name | Expected alleles | Called alleles | #A | #C | #G | #T |
|---|---|---|---|---|---|---|
| P1P2_1/3_2_D | CTTT | CTTT | 0 | 56 | 0 | 298 |
| P1P2_2/2_1 | CCTT | CCTT | 0 | 150 | 0 | 217 |
| P1P2_2/2_1_D | CCTT | CCTT | 0 | 204 | 0 | 284 |
| P1P2_2/2_2 | CCTT | CCTT | 0 | 121 | 0 | 209 |
| P1P2_2/2_2_D | CCCT | CCCT | 0 | 217 | 0 | 187 |
| P1P2_3/1_1 | CCCT | CCCT | 0 | 220 | 0 | 166 |
| P1P2_3/1_1_D | CCCT | CCCT | 0 | 250 | 0 | 188 |
| P1P2_3/1_2 | CCCT | CCCT | 0 | 263 | 0 | 155 |
| P1P2_3/1_2_D | CCCT | CCTT | 0 | 136 | 0 | 168 |
| P1P2_4/0_1 | CCCC | CCCC | 0 | 319 | 0 | 59 |

UMI analysis

| Sample name | Expected alleles | Called alleles | #A | #C | #G | #T |
|---|---|---|---|---|---|---|
| P1P2_1/3_2_D | CTTT | CTTT | 0 | 31 | 0 | 83 |
| P1P2_2/2_1 | CCTT | CCTT | 0 | 57 | 0 | 62 |
| P1P2_2/2_1_D | CCTT | CCTT | 0 | 61 | 0 | 72 |
| P1P2_2/2_2 | CCTT | CCTT | 0 | 54 | 0 | 66 |
| P1P2_2/2_2_D | CCCT | CCCT | 0 | 72 | 0 | 53 |
| P1P2_3/1_1 | CCCT | CCCT | 0 | 91 | 0 | 29 |
| P1P2_3/1_1_D | CCCT | CCCT | 0 | 100 | 0 | 29 |
| P1P2_3/1_2 | CCCT | CCCT | 0 | 103 | 0 | 26 |
| P1P2_3/1_2_D | CCCT | CCCT | 0 | 64 | 0 | 28 |
| P1P2_4/0_1 | CCCC | CCCC | 0 | 136 | 0 | 7 |

*FIG. 3E*

SEQUENCE LISTING

<160> NUMBER OF SEQ ID NOS: 978

<210> SEQ ID NO 1
<211> LENGTH: 60
<212> TYPE: DNA
<213> ORGANISM: artificial sequence
<220> FEATURE:
<223> OTHER INFORMATION: locus probe

<400> SEQUENCE: 1

-continued cgacaggagc aggctgtcct gagctctgaa gatcggaaga gcgtcgtgta gggaaagagt          60

<210> SEQ ID NO 2
<211> LENGTH: 62
<212> TYPE: DNA
<213> ORGANISM: artificial sequence
<220> FEATURE:
<223> OTHER INFORMATION: locus probe

<400> SEQUENCE: 2
aactggggtc tcaagaaagt ccatcgcaca cagatcggaa gagcgtcgtg tagggaaaga          60
gt                                                                          62

<210> SEQ ID NO 3
<211> LENGTH: 62
<212> TYPE: DNA
<213> ORGANISM: artificial sequence
<220> FEATURE:
<223> OTHER INFORMATION: locus probe

<400> SEQUENCE: 3
ggagtcatgg aagttggaga cattactcta cagatcggaa gagcgtcgtg tagggaaaga          60
gt                                                                          62

<210> SEQ ID NO 4
<211> LENGTH: 63
<212> TYPE: DNA
<213> ORGANISM: artificial sequence
<220> FEATURE:
<223> OTHER INFORMATION: locus probe

<400> SEQUENCE: 4
tcatctacga tgcacatcaa taccgtagag tcagatcgga agagcgtcgt gtagggaaag          60
agt                                                                         63

<210> SEQ ID NO 5
<211> LENGTH: 63
<212> TYPE: DNA
<213> ORGANISM: artificial sequence
<220> FEATURE:
<223> OTHER INFORMATION: locus probe

<400> SEQUENCE: 5
atttgaactt ccctccaaaa gtcctagact acagatcgga agagcgtcgt gtagggaaag          60
agt                                                                         63

<210> SEQ ID NO 6
<211> LENGTH: 63
<212> TYPE: DNA
<213> ORGANISM: artificial sequence
<220> FEATURE:
<223> OTHER INFORMATION: locus probe

<400> SEQUENCE: 6
taccttgcaa ccggtatatg atccgtcgac taagatcgga agagcgtcgt gtagggaaag          60
agt                                                                         63

<210> SEQ ID NO 7
<211> LENGTH: 63
<212> TYPE: DNA
<213> ORGANISM: artificial sequence
<220> FEATURE:

-continued

<223> OTHER INFORMATION: locus probe

<400> SEQUENCE: 7

```
caagttcaaa agcagcaaaa ggtggctagc agagatcgga agagcgtcgt gtagggaaag       60
agt                                                                    63
```

```
<210> SEQ ID NO 8
<211> LENGTH: 62
<212> TYPE: DNA
<213> ORGANISM: artificial sequence
<220> FEATURE:
<223> OTHER INFORMATION: locus probe
```

<400> SEQUENCE: 8

```
atgagctgca actggaagtt cagacagact gagatcggaa gagcgtcgtg tagggaaaga       60
gt                                                                     62
```

```
<210> SEQ ID NO 9
<211> LENGTH: 62
<212> TYPE: DNA
<213> ORGANISM: artificial sequence
<220> FEATURE:
<223> OTHER INFORMATION: locus probe
```

<400> SEQUENCE: 9

```
gcactgtagc tgcagactta acacgtagcg cagatcggaa gagcgtcgtg tagggaaaga       60
gt                                                                     62
```

```
<210> SEQ ID NO 10
<211> LENGTH: 61
<212> TYPE: DNA
<213> ORGANISM: artificial sequence
<220> FEATURE:
<223> OTHER INFORMATION: locus probe
```

<400> SEQUENCE: 10

```
agttcagctg ggtggcacag agtagtgata agatcggaag agcgtcgtgt agggaaagag       60
t                                                                      61
```

```
<210> SEQ ID NO 11
<211> LENGTH: 61
<212> TYPE: DNA
<213> ORGANISM: artificial sequence
<220> FEATURE:
<223> OTHER INFORMATION: locus probe
```

<400> SEQUENCE: 11

```
ctcccgatcc cgaccaacta acgtacgatc agatcggaag agcgtcgtgt agggaaagag       60
t                                                                      61
```

```
<210> SEQ ID NO 12
<211> LENGTH: 61
<212> TYPE: DNA
<213> ORGANISM: artificial sequence
<220> FEATURE:
<223> OTHER INFORMATION: locus probe
```

<400> SEQUENCE: 12

```
gttcttggca cctgcaagag accgacatca agatcggaag agcgtcgtgt agggaaagag       60
t                                                                      61
```

-continued

```
<210> SEQ ID NO 13
<211> LENGTH: 59
<212> TYPE: DNA
<213> ORGANISM: artificial sequence
<220> FEATURE:
<223> OTHER INFORMATION: locus probe

<400> SEQUENCE: 13
gtcccatacc cgcccgttgc gctactatag atcggaagag cgtcgtgtag ggaaagagt      59

<210> SEQ ID NO 14
<211> LENGTH: 62
<212> TYPE: DNA
<213> ORGANISM: artificial sequence
<220> FEATURE:
<223> OTHER INFORMATION: locus probe

<400> SEQUENCE: 14
ctctaaaaag tcgtacctga gcgagtcata tagatcggaa gagcgtcgtg tagggaaaga      60
gt                                                                    62

<210> SEQ ID NO 15
<211> LENGTH: 61
<212> TYPE: DNA
<213> ORGANISM: artificial sequence
<220> FEATURE:
<223> OTHER INFORMATION: locus probe

<400> SEQUENCE: 15
gtaaacgcgc tatagggagg gtagtgtaga agatcggaag agcgtcgtgt agggaaagag      60
t                                                                     61

<210> SEQ ID NO 16
<211> LENGTH: 62
<212> TYPE: DNA
<213> ORGANISM: artificial sequence
<220> FEATURE:
<223> OTHER INFORMATION: locus probe

<400> SEQUENCE: 16
agagagagag ttcatgccag tggcgacgca cagatcggaa gagcgtcgtg tagggaaaga      60
gt                                                                    62

<210> SEQ ID NO 17
<211> LENGTH: 63
<212> TYPE: DNA
<213> ORGANISM: artificial sequence
<220> FEATURE:
<223> OTHER INFORMATION: locus probe

<400> SEQUENCE: 17
atgtccaagt gaagtgatct tggtagagtg cgagatcgga agagcgtcgt gtagggaaag      60
agt                                                                   63

<210> SEQ ID NO 18
<211> LENGTH: 63
<212> TYPE: DNA
<213> ORGANISM: artificial sequence
<220> FEATURE:
<223> OTHER INFORMATION: locus probe

<400> SEQUENCE: 18
tctgaagata ttggagctca gcttactcag ctagatcgga agagcgtcgt gtagggaaag      60
```

-continued

```
agt                                                                    63

<210> SEQ ID NO 19
<211> LENGTH: 61
<212> TYPE: DNA
<213> ORGANISM: artificial sequence
<220> FEATURE:
<223> OTHER INFORMATION: locus probe

<400> SEQUENCE: 19
tgacgcgctt ggtacaacat cctgctagtg agatcggaag agcgtcgtgt agggaaagag    60
t                                                                      61

<210> SEQ ID NO 20
<211> LENGTH: 62
<212> TYPE: DNA
<213> ORGANISM: artificial sequence
<220> FEATURE:
<223> OTHER INFORMATION: locus probe

<400> SEQUENCE: 20
cggtccttgt tgtgaaggtt gtagtgcatc gagatcggaa gagcgtcgtg tagggaaaga    60
gt                                                                     62

<210> SEQ ID NO 21
<211> LENGTH: 63
<212> TYPE: DNA
<213> ORGANISM: artificial sequence
<220> FEATURE:
<223> OTHER INFORMATION: locus probe

<400> SEQUENCE: 21
attaaggtgt tgatccgttg tagcgtgtgt ctagatcgga agagcgtcgt gtagggaaag    60
agt                                                                    63

<210> SEQ ID NO 22
<211> LENGTH: 63
<212> TYPE: DNA
<213> ORGANISM: artificial sequence
<220> FEATURE:
<223> OTHER INFORMATION: locus probe

<400> SEQUENCE: 22
gatcctaata attcccacgc atgtagctgt cgagatcgga agagcgtcgt gtagggaaag    60
agt                                                                    63

<210> SEQ ID NO 23
<211> LENGTH: 61
<212> TYPE: DNA
<213> ORGANISM: artificial sequence
<220> FEATURE:
<223> OTHER INFORMATION: locus probe

<400> SEQUENCE: 23
tatggatgct gcgttgccac cctgagcata agatcggaag agcgtcgtgt agggaaagag    60
t                                                                      61

<210> SEQ ID NO 24
<211> LENGTH: 63
<212> TYPE: DNA
<213> ORGANISM: artificial sequence
<220> FEATURE:
<223> OTHER INFORMATION: locus probe
```

-continued

<400> SEQUENCE: 24
gaggcaccac ttaaatggtt ttctactact gcagatcgga agagcgtcgt gtagggaaag        60
agt                                                                       63

<210> SEQ ID NO 25
<211> LENGTH: 62
<212> TYPE: DNA
<213> ORGANISM: artificial sequence
<220> FEATURE:
<223> OTHER INFORMATION: locus probe

<400> SEQUENCE: 25
gcacaatcag acacagcaat aggtagagta tagatcggaa gagcgtcgtg tagggaaaga        60
gt                                                                        62

<210> SEQ ID NO 26
<211> LENGTH: 62
<212> TYPE: DNA
<213> ORGANISM: artificial sequence
<220> FEATURE:
<223> OTHER INFORMATION: locus probe

<400> SEQUENCE: 26
tgcatttctt ggctgcaagt ctgagagcat gagatcggaa gagcgtcgtg tagggaaaga        60
gt                                                                        62

<210> SEQ ID NO 27
<211> LENGTH: 63
<212> TYPE: DNA
<213> ORGANISM: artificial sequence
<220> FEATURE:
<223> OTHER INFORMATION: locus probe

<400> SEQUENCE: 27
cacaagatgg aatggaagag ctagcagata gtagatcgga agagcgtcgt gtagggaaag        60
agt                                                                       63

<210> SEQ ID NO 28
<211> LENGTH: 62
<212> TYPE: DNA
<213> ORGANISM: artificial sequence
<220> FEATURE:
<223> OTHER INFORMATION: locus probe

<400> SEQUENCE: 28
ggagtggaca gaatgaaact gaccatgtga cagatcggaa gagcgtcgtg tagggaaaga        60
gt                                                                        62

<210> SEQ ID NO 29
<211> LENGTH: 61
<212> TYPE: DNA
<213> ORGANISM: artificial sequence
<220> FEATURE:
<223> OTHER INFORMATION: locus probe

<400> SEQUENCE: 29
gcctctctgg atagcacaca agctcgctgt agatcggaag agcgtcgtgt agggaaagag        60
t                                                                         61

<210> SEQ ID NO 30

-continued

```
<211> LENGTH: 61
<212> TYPE: DNA
<213> ORGANISM: artificial sequence
<220> FEATURE:
<223> OTHER INFORMATION: locus probe

<400> SEQUENCE: 30
gaggcctcac gcacaacaac atctgactcg agatcggaag agcgtcgtgt agggaaagag       60
t                                                                        61

<210> SEQ ID NO 31
<211> LENGTH: 62
<212> TYPE: DNA
<213> ORGANISM: artificial sequence
<220> FEATURE:
<223> OTHER INFORMATION: locus probe

<400> SEQUENCE: 31
ctgactttct gccggggtaa aaacgatact gagatcggaa gagcgtcgtg tagggaaaga       60
gt                                                                       62

<210> SEQ ID NO 32
<211> LENGTH: 62
<212> TYPE: DNA
<213> ORGANISM: artificial sequence
<220> FEATURE:
<223> OTHER INFORMATION: locus probe

<400> SEQUENCE: 32
caatacagat acggacgacc gatgcatctg aagatcggaa gagcgtcgtg tagggaaaga       60
gt                                                                       62

<210> SEQ ID NO 33
<211> LENGTH: 62
<212> TYPE: DNA
<213> ORGANISM: artificial sequence
<220> FEATURE:
<223> OTHER INFORMATION: locus probe

<400> SEQUENCE: 33
tactactcaa caaagctcgc cgctgtgtca cagatcggaa gagcgtcgtg tagggaaaga       60
gt                                                                       62

<210> SEQ ID NO 34
<211> LENGTH: 63
<212> TYPE: DNA
<213> ORGANISM: artificial sequence
<220> FEATURE:
<223> OTHER INFORMATION: locus probe

<400> SEQUENCE: 34
gaggtaatgt atgtttccag tgacactata ctagatcgga agagcgtcgt gtagggaaag       60
agt                                                                      63

<210> SEQ ID NO 35
<211> LENGTH: 63
<212> TYPE: DNA
<213> ORGANISM: artificial sequence
<220> FEATURE:
<223> OTHER INFORMATION: locus probe

<400> SEQUENCE: 35
aaccaataat tacgcgtgaa cgtcctgatc gaagatcgga agagcgtcgt gtagggaaag       60
```

-continued

```
agt                                                          63

<210> SEQ ID NO 36
<211> LENGTH: 59
<212> TYPE: DNA
<213> ORGANISM: artificial sequence
<220> FEATURE:
<223> OTHER INFORMATION: locus probe

<400> SEQUENCE: 36
ggaaccagcg gccaggatcg agcacatgag atcggaagag cgtcgtgtag ggaaagagt    59

<210> SEQ ID NO 37
<211> LENGTH: 64
<212> TYPE: DNA
<213> ORGANISM: artificial sequence
<220> FEATURE:
<223> OTHER INFORMATION: locus probe

<400> SEQUENCE: 37
ggtcttcagt aaaatcactc atgtaacgta tagagatcgg aagagcgtcg tgtagggaaa    60
gagt                                                         64

<210> SEQ ID NO 38
<211> LENGTH: 63
<212> TYPE: DNA
<213> ORGANISM: artificial sequence
<220> FEATURE:
<223> OTHER INFORMATION: locus probe

<400> SEQUENCE: 38
gaatggaatt agatcatccg gatgtacaga cgagatcgga agagcgtcgt gtagggaaag    60
agt                                                          63

<210> SEQ ID NO 39
<211> LENGTH: 61
<212> TYPE: DNA
<213> ORGANISM: artificial sequence
<220> FEATURE:
<223> OTHER INFORMATION: locus probe

<400> SEQUENCE: 39
cgtgactgga acatcggaca gcctgatgac agatcggaag agcgtcgtgt agggaaagag    60
t                                                            61

<210> SEQ ID NO 40
<211> LENGTH: 65
<212> TYPE: DNA
<213> ORGANISM: artificial sequence
<220> FEATURE:
<223> OTHER INFORMATION: locus probe

<400> SEQUENCE: 40
ttttgaaatt tgctgctgat aagttgatgc tataagatcg gaagagcgtc gtgtagggaa    60
agagt                                                        65

<210> SEQ ID NO 41
<211> LENGTH: 62
<212> TYPE: DNA
<213> ORGANISM: artificial sequence
<220> FEATURE:
<223> OTHER INFORMATION: locus probe
```

-continued

```
<400> SEQUENCE: 41
caactactat cgtacacagc tgcactctca cagatcggaa gagcgtcgtg tagggaaaga    60
gt                                                                   62

<210> SEQ ID NO 42
<211> LENGTH: 63
<212> TYPE: DNA
<213> ORGANISM: artificial sequence
<220> FEATURE:
<223> OTHER INFORMATION: locus probe

<400> SEQUENCE: 42
ggcacttact agttactacg tacctgtgat cgagatcgga agagcgtcgt gtagggaaag    60
agt                                                                  63

<210> SEQ ID NO 43
<211> LENGTH: 63
<212> TYPE: DNA
<213> ORGANISM: artificial sequence
<220> FEATURE:
<223> OTHER INFORMATION: locus probe

<400> SEQUENCE: 43
cgagttgctg cagatattgg taagctcgtc gaagatcgga agagcgtcgt gtagggaaag    60
agt                                                                  63

<210> SEQ ID NO 44
<211> LENGTH: 64
<212> TYPE: DNA
<213> ORGANISM: artificial sequence
<220> FEATURE:
<223> OTHER INFORMATION: locus probe

<400> SEQUENCE: 44
agatagatgg gcacaaaatg gattccgacg ctaagatcgg aagagcgtcg tgtagggaaa    60
gagt                                                                 64

<210> SEQ ID NO 45
<211> LENGTH: 63
<212> TYPE: DNA
<213> ORGANISM: artificial sequence
<220> FEATURE:
<223> OTHER INFORMATION: locus probe

<400> SEQUENCE: 45
acctctgaaa gtttttgtgc tgctatcgta gaagatcgga agagcgtcgt gtagggaaag    60
agt                                                                  63

<210> SEQ ID NO 46
<211> LENGTH: 62
<212> TYPE: DNA
<213> ORGANISM: artificial sequence
<220> FEATURE:
<223> OTHER INFORMATION: locus probe

<400> SEQUENCE: 46
gcaagcacct gacattgatg ctcatcagct gagatcggaa gagcgtcgtg tagggaaaga    60
gt                                                                   62

<210> SEQ ID NO 47
<211> LENGTH: 63
```

-continued

```
<212> TYPE: DNA
<213> ORGANISM: artificial sequence
<220> FEATURE:
<223> OTHER INFORMATION: locus probe

<400> SEQUENCE: 47
cagtcagcgt aacaatgctt tgatgtagac gcagatcgga agagcgtcgt gtagggaaag        60
agt                                                                       63

<210> SEQ ID NO 48
<211> LENGTH: 62
<212> TYPE: DNA
<213> ORGANISM: artificial sequence
<220> FEATURE:
<223> OTHER INFORMATION: locus probe

<400> SEQUENCE: 48
ccgtacatct ttcagcatga cccgcagcga cagatcggaa gagcgtcgtg tagggaaaga        60
gt                                                                        62

<210> SEQ ID NO 49
<211> LENGTH: 62
<212> TYPE: DNA
<213> ORGANISM: artificial sequence
<220> FEATURE:
<223> OTHER INFORMATION: locus probe

<400> SEQUENCE: 49
gtgcaaccga gcctatatat gcaagatact aagatcggaa gagcgtcgtg tagggaaaga        60
gt                                                                        62

<210> SEQ ID NO 50
<211> LENGTH: 63
<212> TYPE: DNA
<213> ORGANISM: artificial sequence
<220> FEATURE:
<223> OTHER INFORMATION: locus probe

<400> SEQUENCE: 50
aatccccaac cacatttatg tagcctgaca gtagatcgga agagcgtcgt gtagggaaag        60
agt                                                                       63

<210> SEQ ID NO 51
<211> LENGTH: 62
<212> TYPE: DNA
<213> ORGANISM: artificial sequence
<220> FEATURE:
<223> OTHER INFORMATION: locus probe

<400> SEQUENCE: 51
gctcacaagc tgaaacagga acagcgctga tagatcggaa gagcgtcgtg tagggaaaga        60
gt                                                                        62

<210> SEQ ID NO 52
<211> LENGTH: 62
<212> TYPE: DNA
<213> ORGANISM: artificial sequence
<220> FEATURE:
<223> OTHER INFORMATION: locus probe

<400> SEQUENCE: 52
aagctccatc caacctgatc tgctcgcact aagatcggaa gagcgtcgtg tagggaaaga        60
``` gt                                                            62

<210> SEQ ID NO 53
<211> LENGTH: 61
<212> TYPE: DNA
<213> ORGANISM: artificial sequence
<220> FEATURE:
<223> OTHER INFORMATION: locus probe

<400> SEQUENCE: 53
gctcgggagc ctgctaaaga taactcatac agatcggaag agcgtcgtgt agggaaagag        60
t                                                             61

<210> SEQ ID NO 54
<211> LENGTH: 64
<212> TYPE: DNA
<213> ORGANISM: artificial sequence
<220> FEATURE:
<223> OTHER INFORMATION: locus probe

<400> SEQUENCE: 54
tcttgttcag tgccatagaa aaaagagcag ctcagatcgg aagagcgtcg tgtagggaaa        60
gagt                                                          64

<210> SEQ ID NO 55
<211> LENGTH: 62
<212> TYPE: DNA
<213> ORGANISM: artificial sequence
<220> FEATURE:
<223> OTHER INFORMATION: locus probe

<400> SEQUENCE: 55
tcgatgaaga tcctggaacc gacctgtcac tagatcggaa gagcgtcgtg tagggaaaga        60
gt                                                            62

<210> SEQ ID NO 56
<211> LENGTH: 65
<212> TYPE: DNA
<213> ORGANISM: artificial sequence
<220> FEATURE:
<223> OTHER INFORMATION: locus probe

<400> SEQUENCE: 56
cttcaatttt tcacaaatag tgcatgcatc gtgtagatcg gaagagcgtc gtgtagggaa        60
agagt                                                         65

<210> SEQ ID NO 57
<211> LENGTH: 60
<212> TYPE: DNA
<213> ORGANISM: artificial sequence
<220> FEATURE:
<223> OTHER INFORMATION: locus probe

<400> SEQUENCE: 57
acctgcaaga caggcgcacc ctcgacgcga gatcggaaga gcgtcgtgta gggaaagagt        60

<210> SEQ ID NO 58
<211> LENGTH: 62
<212> TYPE: DNA
<213> ORGANISM: artificial sequence
<220> FEATURE:
<223> OTHER INFORMATION: locus probe

<400> SEQUENCE: 58

-continued

```
ggtagctcgt gaaagctaag cttatacgta cagatcggaa gagcgtcgtg tagggaaaga        60
gt                                                                        62

<210> SEQ ID NO 59
<211> LENGTH: 62
<212> TYPE: DNA
<213> ORGANISM: artificial sequence
<220> FEATURE:
<223> OTHER INFORMATION: locus probe

<400> SEQUENCE: 59
tgtgtattcg cactccacct gacgcatgca tagatcggaa gagcgtcgtg tagggaaaga        60
gt                                                                        62

<210> SEQ ID NO 60
<211> LENGTH: 61
<212> TYPE: DNA
<213> ORGANISM: artificial sequence
<220> FEATURE:
<223> OTHER INFORMATION: locus probe

<400> SEQUENCE: 60
aatccggtgg tactgtacac ggcacgagac agatcggaag agcgtcgtgt agggaaagag        60
t                                                                         61

<210> SEQ ID NO 61
<211> LENGTH: 61
<212> TYPE: DNA
<213> ORGANISM: artificial sequence
<220> FEATURE:
<223> OTHER INFORMATION: locus probe

<400> SEQUENCE: 61
cagcagagag gttgttggat ccgagtatct agatcggaag agcgtcgtgt agggaaagag        60
t                                                                         61

<210> SEQ ID NO 62
<211> LENGTH: 63
<212> TYPE: DNA
<213> ORGANISM: artificial sequence
<220> FEATURE:
<223> OTHER INFORMATION: locus probe

<400> SEQUENCE: 62
tcacagaaag agagcattac ggtttgctga taagatcgga agagcgtcgt gtagggaaag        60
agt                                                                       63

<210> SEQ ID NO 63
<211> LENGTH: 61
<212> TYPE: DNA
<213> ORGANISM: artificial sequence
<220> FEATURE:
<223> OTHER INFORMATION: locus probe

<400> SEQUENCE: 63
atccgccatt gtaggccatg acagtagcga agatcggaag agcgtcgtgt agggaaagag        60
t                                                                         61

<210> SEQ ID NO 64
<211> LENGTH: 62
<212> TYPE: DNA
```

-continued

```
<213> ORGANISM: artificial sequence
<220> FEATURE:
<223> OTHER INFORMATION: locus probe

<400> SEQUENCE: 64
gttcaattcg caagctggag tagctagatg aagatcggaa gagcgtcgtg tagggaaaga        60
gt                                                                       62

<210> SEQ ID NO 65
<211> LENGTH: 59
<212> TYPE: DNA
<213> ORGANISM: artificial sequence
<220> FEATURE:
<223> OTHER INFORMATION: locus probe

<400> SEQUENCE: 65
ggaggcaatg gtggtggggg tagactcgag atcggaagag cgtcgtgtag ggaaagagt         59

<210> SEQ ID NO 66
<211> LENGTH: 60
<212> TYPE: DNA
<213> ORGANISM: artificial sequence
<220> FEATURE:
<223> OTHER INFORMATION: locus probe

<400> SEQUENCE: 66
gtccagggat cgtcttcccc agtagtgtga gatcggaaga gcgtcgtgta gggaaagagt        60

<210> SEQ ID NO 67
<211> LENGTH: 62
<212> TYPE: DNA
<213> ORGANISM: artificial sequence
<220> FEATURE:
<223> OTHER INFORMATION: locus probe

<400> SEQUENCE: 67
agagtttgcc atctgctgca tgcgagatga gagatcggaa gagcgtcgtg tagggaaaga        60
gt                                                                       62

<210> SEQ ID NO 68
<211> LENGTH: 61
<212> TYPE: DNA
<213> ORGANISM: artificial sequence
<220> FEATURE:
<223> OTHER INFORMATION: locus probe

<400> SEQUENCE: 68
tccatcgaca gagcttgcga gcctatagct agatcggaag agcgtcgtgt agggaaagag        60
t                                                                        61

<210> SEQ ID NO 69
<211> LENGTH: 62
<212> TYPE: DNA
<213> ORGANISM: artificial sequence
<220> FEATURE:
<223> OTHER INFORMATION: locus probe

<400> SEQUENCE: 69
agtcctagtg cttgtcctca atcatgctga gagatcggaa gagcgtcgtg tagggaaaga        60
gt                                                                       62

<210> SEQ ID NO 70
<211> LENGTH: 63
```

<212> TYPE: DNA
<213> ORGANISM: artificial sequence
<220> FEATURE:
<223> OTHER INFORMATION: locus probe

<400> SEQUENCE: 70
gtctccttga agagctgttc aaagcgctac gtagatcgga agagcgtcgt gtagggaaag      60
agt                                                                    63

<210> SEQ ID NO 71
<211> LENGTH: 60
<212> TYPE: DNA
<213> ORGANISM: artificial sequence
<220> FEATURE:
<223> OTHER INFORMATION: locus probe

<400> SEQUENCE: 71
cagagagagg tcgtggttgg ggcgcataca gatcggaaga gcgtcgtgta gggaaagagt      60

<210> SEQ ID NO 72
<211> LENGTH: 62
<212> TYPE: DNA
<213> ORGANISM: artificial sequence
<220> FEATURE:
<223> OTHER INFORMATION: locus probe

<400> SEQUENCE: 72
tctacaatga cccgtggcaa gttgtcacgc tagatcggaa gagcgtcgtg tagggaaaga      60
gt                                                                     62

<210> SEQ ID NO 73
<211> LENGTH: 62
<212> TYPE: DNA
<213> ORGANISM: artificial sequence
<220> FEATURE:
<223> OTHER INFORMATION: locus probe

<400> SEQUENCE: 73
tcgttccttt ctttccatcg tcggacatac aagatcggaa gagcgtcgtg tagggaaaga      60
gt                                                                     62

<210> SEQ ID NO 74
<211> LENGTH: 63
<212> TYPE: DNA
<213> ORGANISM: artificial sequence
<220> FEATURE:
<223> OTHER INFORMATION: locus probe

<400> SEQUENCE: 74
agcttcatgt gcactccaaa ctatgcacta gaagatcgga agagcgtcgt gtagggaaag      60
agt                                                                    63

<210> SEQ ID NO 75
<211> LENGTH: 64
<212> TYPE: DNA
<213> ORGANISM: artificial sequence
<220> FEATURE:
<223> OTHER INFORMATION: locus probe

<400> SEQUENCE: 75
acacacattt gatgaagcaa cgaatcagtc tgaagatcgg aagagcgtcg tgtagggaaa      60
gagt                                                                   64

-continued

```
<210> SEQ ID NO 76
<211> LENGTH: 61
<212> TYPE: DNA
<213> ORGANISM: artificial sequence
<220> FEATURE:
<223> OTHER INFORMATION: locus probe

<400> SEQUENCE: 76
ccttcagtct ctgccagtct gcatacacgc agatcggaag agcgtcgtgt agggaaagag      60
t                                                                     61

<210> SEQ ID NO 77
<211> LENGTH: 63
<212> TYPE: DNA
<213> ORGANISM: artificial sequence
<220> FEATURE:
<223> OTHER INFORMATION: locus probe

<400> SEQUENCE: 77
acatgaaggt caacaccaag atcaagctat gtagatcgga agagcgtcgt gtagggaaag      60
agt                                                                   63

<210> SEQ ID NO 78
<211> LENGTH: 63
<212> TYPE: DNA
<213> ORGANISM: artificial sequence
<220> FEATURE:
<223> OTHER INFORMATION: locus probe

<400> SEQUENCE: 78
agaccaattc agatgccaca cttttgcacg tcagatcgga agagcgtcgt gtagggaaag      60
agt                                                                   63

<210> SEQ ID NO 79
<211> LENGTH: 60
<212> TYPE: DNA
<213> ORGANISM: artificial sequence
<220> FEATURE:
<223> OTHER INFORMATION: locus probe

<400> SEQUENCE: 79
ctgtcgcgct ccaggtactc cgtctagtaa gatcggaaga gcgtcgtgta gggaaagagt      60

<210> SEQ ID NO 80
<211> LENGTH: 61
<212> TYPE: DNA
<213> ORGANISM: artificial sequence
<220> FEATURE:
<223> OTHER INFORMATION: locus probe

<400> SEQUENCE: 80
gaagacatgg taccggagct tcagcgagac agatcggaag agcgtcgtgt agggaaagag      60
t                                                                     61

<210> SEQ ID NO 81
<211> LENGTH: 61
<212> TYPE: DNA
<213> ORGANISM: artificial sequence
<220> FEATURE:
<223> OTHER INFORMATION: locus probe

<400> SEQUENCE: 81
agctagcatg gcatctcgac gaagctcagt agatcggaag agcgtcgtgt agggaaagag      60
```

```
t                                                                          61

<210> SEQ ID NO 82
<211> LENGTH: 63
<212> TYPE: DNA
<213> ORGANISM: artificial sequence
<220> FEATURE:
<223> OTHER INFORMATION: locus probe

<400> SEQUENCE: 82
tgttgccaaa attcgcacgt tagtcgatat agagatcgga agagcgtcgt gtagggaaag       60
agt                                                                        63

<210> SEQ ID NO 83
<211> LENGTH: 64
<212> TYPE: DNA
<213> ORGANISM: artificial sequence
<220> FEATURE:
<223> OTHER INFORMATION: locus probe

<400> SEQUENCE: 83
ttgcttgttt attggaacag ccattgatac gatagatcgg aagagcgtcg tgtagggaaa       60
gagt                                                                       64

<210> SEQ ID NO 84
<211> LENGTH: 63
<212> TYPE: DNA
<213> ORGANISM: artificial sequence
<220> FEATURE:
<223> OTHER INFORMATION: locus probe

<400> SEQUENCE: 84
tttacttcac ctgctctctc tctgcgacat atagatcgga agagcgtcgt gtagggaaag       60
agt                                                                        63

<210> SEQ ID NO 85
<211> LENGTH: 61
<212> TYPE: DNA
<213> ORGANISM: artificial sequence
<220> FEATURE:
<223> OTHER INFORMATION: locus probe

<400> SEQUENCE: 85
tcgacggtga catgccactt ccatctagag agatcggaag agcgtcgtgt agggaaagag       60
t                                                                          61

<210> SEQ ID NO 86
<211> LENGTH: 63
<212> TYPE: DNA
<213> ORGANISM: artificial sequence
<220> FEATURE:
<223> OTHER INFORMATION: locus probe

<400> SEQUENCE: 86
ttgcagcaaa ttgttcgttg catctgcgtg taagatcgga agagcgtcgt gtagggaaag       60
agt                                                                        63

<210> SEQ ID NO 87
<211> LENGTH: 63
<212> TYPE: DNA
<213> ORGANISM: artificial sequence
<220> FEATURE:
```

<223> OTHER INFORMATION: locus probe

<400> SEQUENCE: 87
gtaaaggagg atggattctg caatgagcag taagatcgga agagcgtcgt gtagggaaag        60
agt                                                                       63

<210> SEQ ID NO 88
<211> LENGTH: 61
<212> TYPE: DNA
<213> ORGANISM: artificial sequence
<220> FEATURE:
<223> OTHER INFORMATION: locus probe

<400> SEQUENCE: 88
gacttgctgt gaacgagccg ttgacacata agatcggaag agcgtcgtgt agggaaagag        60
t                                                                         61

<210> SEQ ID NO 89
<211> LENGTH: 60
<212> TYPE: DNA
<213> ORGANISM: artificial sequence
<220> FEATURE:
<223> OTHER INFORMATION: locus probe

<400> SEQUENCE: 89
tgacccgttc cgctcttgcg cgtatagcga gatcggaaga gcgtcgtgta gggaaagagt        60

<210> SEQ ID NO 90
<211> LENGTH: 63
<212> TYPE: DNA
<213> ORGANISM: artificial sequence
<220> FEATURE:
<223> OTHER INFORMATION: locus probe

<400> SEQUENCE: 90
catgacaggt attctgaaaa ccgttagatg acagatcgga agagcgtcgt gtagggaaag        60
agt                                                                       63

<210> SEQ ID NO 91
<211> LENGTH: 64
<212> TYPE: DNA
<213> ORGANISM: artificial sequence
<220> FEATURE:
<223> OTHER INFORMATION: locus probe

<400> SEQUENCE: 91
aaaataaaac ctcgcagcaa cttgggtcac atcagatcgg aagagcgtcg tgtagggaaa        60
gagt                                                                      64

<210> SEQ ID NO 92
<211> LENGTH: 62
<212> TYPE: DNA
<213> ORGANISM: artificial sequence
<220> FEATURE:
<223> OTHER INFORMATION: locus probe

<400> SEQUENCE: 92
ttttgtcgtg ggcgagccaa atctcgatgc aagatcggaa gagcgtcgtg tagggaaaga        60
gt                                                                        62

<210> SEQ ID NO 93
<211> LENGTH: 61

```
<212> TYPE: DNA
<213> ORGANISM: artificial sequence
<220> FEATURE:
<223> OTHER INFORMATION: locus probe

<400> SEQUENCE: 93
gtgtattggc taccagcctc agtcagctat agatcggaag agcgtcgtgt agggaaagag      60
t                                                                    61

<210> SEQ ID NO 94
<211> LENGTH: 60
<212> TYPE: DNA
<213> ORGANISM: artificial sequence
<220> FEATURE:
<223> OTHER INFORMATION: locus probe

<400> SEQUENCE: 94
gcttccatgg atctggaccg ggctactgaa gatcggaaga gcgtcgtgta gggaaagagt      60

<210> SEQ ID NO 95
<211> LENGTH: 61
<212> TYPE: DNA
<213> ORGANISM: artificial sequence
<220> FEATURE:
<223> OTHER INFORMATION: locus probe

<400> SEQUENCE: 95
cagtgaccct cgctttcgaa cctgcgcgac agatcggaag agcgtcgtgt agggaaagag      60
t                                                                    61

<210> SEQ ID NO 96
<211> LENGTH: 62
<212> TYPE: DNA
<213> ORGANISM: artificial sequence
<220> FEATURE:
<223> OTHER INFORMATION: locus probe

<400> SEQUENCE: 96
gaatggctgc gatcaagatt gggtcgctat cagatcggaa gagcgtcgtg tagggaaaga      60
gt                                                                   62

<210> SEQ ID NO 97
<211> LENGTH: 63
<212> TYPE: DNA
<213> ORGANISM: artificial sequence
<220> FEATURE:
<223> OTHER INFORMATION: locus probe

<400> SEQUENCE: 97
tgctgctggt gagctaataa tcttatagtc atagatcgga agagcgtcgt gtagggaaag      60
agt                                                                  63

<210> SEQ ID NO 98
<211> LENGTH: 62
<212> TYPE: DNA
<213> ORGANISM: artificial sequence
<220> FEATURE:
<223> OTHER INFORMATION: locus probe

<400> SEQUENCE: 98
acctctggag tattctgaag tggtgagtac gagatcggaa gagcgtcgtg tagggaaaga      60
gt                                                                   62
```

```
<210> SEQ ID NO 99
<211> LENGTH: 62
<212> TYPE: DNA
<213> ORGANISM: artificial sequence
<220> FEATURE:
<223> OTHER INFORMATION: locus probe

<400> SEQUENCE: 99
taccctttcc ttagggacga cagtgctcgc aagatcggaa gagcgtcgtg tagggaaaga      60
gt                                                                     62

<210> SEQ ID NO 100
<211> LENGTH: 62
<212> TYPE: DNA
<213> ORGANISM: artificial sequence
<220> FEATURE:
<223> OTHER INFORMATION: locus probe

<400> SEQUENCE: 100
tccactaggg tagatcactc tgcactcact gagatcggaa gagcgtcgtg tagggaaaga      60
gt                                                                     62

<210> SEQ ID NO 101
<211> LENGTH: 63
<212> TYPE: DNA
<213> ORGANISM: artificial sequence
<220> FEATURE:
<223> OTHER INFORMATION: locus probe

<400> SEQUENCE: 101
gataaacaaa gagctgcaat ggccatgcat ctagatcgga agagcgtcgt gtagggaaag      60
agt                                                                    63

<210> SEQ ID NO 102
<211> LENGTH: 62
<212> TYPE: DNA
<213> ORGANISM: artificial sequence
<220> FEATURE:
<223> OTHER INFORMATION: locus probe

<400> SEQUENCE: 102
acagatacct ctttagctgc acctactctg aagatcggaa gagcgtcgtg tagggaaaga      60
gt                                                                     62

<210> SEQ ID NO 103
<211> LENGTH: 62
<212> TYPE: DNA
<213> ORGANISM: artificial sequence
<220> FEATURE:
<223> OTHER INFORMATION: locus probe

<400> SEQUENCE: 103
gggagattca ggtaagtgtg tgcacgtagc gagatcggaa gagcgtcgtg tagggaaaga      60
gt                                                                     62

<210> SEQ ID NO 104
<211> LENGTH: 63
<212> TYPE: DNA
<213> ORGANISM: artificial sequence
<220> FEATURE:
<223> OTHER INFORMATION: locus probe

<400> SEQUENCE: 104
```
ttcctgaagt aaaagttcct cagcctctac gcagatcgga agagcgtcgt gtagggaaag        60
agt                                                                        63

<210> SEQ ID NO 105
<211> LENGTH: 59
<212> TYPE: DNA
<213> ORGANISM: artificial sequence
<220> FEATURE:
<223> OTHER INFORMATION: locus probe

<400> SEQUENCE: 105
caggccagcg tccctgacca gctcgtagag atcggaagag cgtcgtgtag ggaaagagt          59

<210> SEQ ID NO 106
<211> LENGTH: 62
<212> TYPE: DNA
<213> ORGANISM: artificial sequence
<220> FEATURE:
<223> OTHER INFORMATION: locus probe

<400> SEQUENCE: 106
atttcctctg cactcagtcc agcatgactc tagatcggaa gagcgtcgtg tagggaaaga        60
gt                                                                         62

<210> SEQ ID NO 107
<211> LENGTH: 62
<212> TYPE: DNA
<213> ORGANISM: artificial sequence
<220> FEATURE:
<223> OTHER INFORMATION: locus probe

<400> SEQUENCE: 107
gtttggatcc tctgtaactg cgtgtgagag aagatcggaa gagcgtcgtg tagggaaaga        60
gt                                                                         62

<210> SEQ ID NO 108
<211> LENGTH: 60
<212> TYPE: DNA
<213> ORGANISM: artificial sequence
<220> FEATURE:
<223> OTHER INFORMATION: locus probe

<400> SEQUENCE: 108
cgcggcatcg atggctacga gagctcataa gatcggaaga gcgtcgtgta gggaaagagt        60

<210> SEQ ID NO 109
<211> LENGTH: 64
<212> TYPE: DNA
<213> ORGANISM: artificial sequence
<220> FEATURE:
<223> OTHER INFORMATION: locus probe

<400> SEQUENCE: 109
cgtcatataa aagggattaa gaggccgtag cagagatcgg aagagcgtcg tgtagggaaa        60
gagt                                                                       64

<210> SEQ ID NO 110
<211> LENGTH: 64
<212> TYPE: DNA
<213> ORGANISM: artificial sequence
<220> FEATURE:
<223> OTHER INFORMATION: locus probe -continued

```
<400> SEQUENCE: 110
aagcatattt ctttctccga gtgattacat gtcagatcgg aagagcgtcg tgtagggaaa      60
gagt                                                                    64

<210> SEQ ID NO 111
<211> LENGTH: 62
<212> TYPE: DNA
<213> ORGANISM: artificial sequence
<220> FEATURE:
<223> OTHER INFORMATION: locus probe

<400> SEQUENCE: 111
acacgatata ccggcgacga ataagctcac gagatcggaa gagcgtcgtg tagggaaaga      60
gt                                                                      62

<210> SEQ ID NO 112
<211> LENGTH: 63
<212> TYPE: DNA
<213> ORGANISM: artificial sequence
<220> FEATURE:
<223> OTHER INFORMATION: locus probe

<400> SEQUENCE: 112
ccatcaacat attgctgcag tgtcgagcag ctagatcgga agagcgtcgt gtagggaaag      60
agt                                                                     63

<210> SEQ ID NO 113
<211> LENGTH: 63
<212> TYPE: DNA
<213> ORGANISM: artificial sequence
<220> FEATURE:
<223> OTHER INFORMATION: locus probe

<400> SEQUENCE: 113
tgcttgggtt taacgtcaga aacatcagag atagatcgga agagcgtcgt gtagggaaag      60
agt                                                                     63

<210> SEQ ID NO 114
<211> LENGTH: 64
<212> TYPE: DNA
<213> ORGANISM: artificial sequence
<220> FEATURE:
<223> OTHER INFORMATION: locus probe

<400> SEQUENCE: 114
aatactcctt gagatggaac agaagcgagc tagagatcgg aagagcgtcg tgtagggaaa      60
gagt                                                                    64

<210> SEQ ID NO 115
<211> LENGTH: 60
<212> TYPE: DNA
<213> ORGANISM: artificial sequence
<220> FEATURE:
<223> OTHER INFORMATION: locus probe

<400> SEQUENCE: 115
tctcctcccc tagtggctga gtgcacacga gatcggaaga gcgtcgtgta gggaaagagt      60

<210> SEQ ID NO 116
<211> LENGTH: 63
<212> TYPE: DNA
<213> ORGANISM: artificial sequence
```

-continued

```
<220> FEATURE:
<223> OTHER INFORMATION: locus probe

<400> SEQUENCE: 116
aacaaaaacg tctttattgc cggcatcgag tcagatcgga agagcgtcgt gtagggaaag      60
agt                                                                    63

<210> SEQ ID NO 117
<211> LENGTH: 65
<212> TYPE: DNA
<213> ORGANISM: artificial sequence
<220> FEATURE:
<223> OTHER INFORMATION: locus probe

<400> SEQUENCE: 117
gagaatgatc agtaaatgca ataagcgtga cataagatcg gaagagcgtc gtgtagggaa      60
agagt                                                                  65

<210> SEQ ID NO 118
<211> LENGTH: 64
<212> TYPE: DNA
<213> ORGANISM: artificial sequence
<220> FEATURE:
<223> OTHER INFORMATION: locus probe

<400> SEQUENCE: 118
aacataccat gcaaatgtgt tgacgcacga gcgagatcgg aagagcgtcg tgtagggaaa      60
gagt                                                                   64

<210> SEQ ID NO 119
<211> LENGTH: 62
<212> TYPE: DNA
<213> ORGANISM: artificial sequence
<220> FEATURE:
<223> OTHER INFORMATION: locus probe

<400> SEQUENCE: 119
ggcagtcaga atctttgatg cgccatgtca tagatcggaa gagcgtcgtg tagggaaaga      60
gt                                                                     62

<210> SEQ ID NO 120
<211> LENGTH: 61
<212> TYPE: DNA
<213> ORGANISM: artificial sequence
<220> FEATURE:
<223> OTHER INFORMATION: locus probe

<400> SEQUENCE: 120
gttggacgtt ttgaagtccc ggtatctctg agatcggaag agcgtcgtgt agggaaagag      60
t                                                                      61

<210> SEQ ID NO 121
<211> LENGTH: 60
<212> TYPE: DNA
<213> ORGANISM: artificial sequence
<220> FEATURE:
<223> OTHER INFORMATION: locus probe

<400> SEQUENCE: 121
ggtgagcacg gttccgtgat cctgagtgta gatcggaaga gcgtcgtgta gggaaagagt      60

<210> SEQ ID NO 122
```

```
<211> LENGTH: 62
<212> TYPE: DNA
<213> ORGANISM: artificial sequence
<220> FEATURE:
<223> OTHER INFORMATION: locus probe

<400> SEQUENCE: 122
cttttctgga tcacaccgac taggtagata tagatcggaa gagcgtcgtg tagggaaaga      60
gt                                                                    62

<210> SEQ ID NO 123
<211> LENGTH: 61
<212> TYPE: DNA
<213> ORGANISM: artificial sequence
<220> FEATURE:
<223> OTHER INFORMATION: locus probe

<400> SEQUENCE: 123
ggtggactct ctctcctttg gccactagtg agatcggaag agcgtcgtgt agggaaagag      60
t                                                                     61

<210> SEQ ID NO 124
<211> LENGTH: 63
<212> TYPE: DNA
<213> ORGANISM: artificial sequence
<220> FEATURE:
<223> OTHER INFORMATION: locus probe

<400> SEQUENCE: 124
gatagcgcaa taattaaacc ggcgcgacgt ctagatcgga agagcgtcgt gtagggaaag      60
agt                                                                   63

<210> SEQ ID NO 125
<211> LENGTH: 61
<212> TYPE: DNA
<213> ORGANISM: artificial sequence
<220> FEATURE:
<223> OTHER INFORMATION: locus probe

<400> SEQUENCE: 125
gcaacaagcc acgacctctt gactagtagc agatcggaag agcgtcgtgt agggaaagag      60
t                                                                     61

<210> SEQ ID NO 126
<211> LENGTH: 62
<212> TYPE: DNA
<213> ORGANISM: artificial sequence
<220> FEATURE:
<223> OTHER INFORMATION: locus probe

<400> SEQUENCE: 126
gacctgccaa cacaaaatag tgcgcgtctg cagatcggaa gagcgtcgtg tagggaaaga      60
gt                                                                    62

<210> SEQ ID NO 127
<211> LENGTH: 62
<212> TYPE: DNA
<213> ORGANISM: artificial sequence
<220> FEATURE:
<223> OTHER INFORMATION: locus probe

<400> SEQUENCE: 127
ctctacttgc gaacacgttc tgttagtcac tagatcggaa gagcgtcgtg tagggaaaga      60
```

-continued gt                                                                                       62

<210> SEQ ID NO 128
<211> LENGTH: 63
<212> TYPE: DNA
<213> ORGANISM: artificial sequence
<220> FEATURE:
<223> OTHER INFORMATION: locus probe

<400> SEQUENCE: 128
tagacacatg taataaggcc accctacatc gtagatcgga agagcgtcgt gtagggaaag       60
agt                                                                                      63

<210> SEQ ID NO 129
<211> LENGTH: 62
<212> TYPE: DNA
<213> ORGANISM: artificial sequence
<220> FEATURE:
<223> OTHER INFORMATION: locus probe

<400> SEQUENCE: 129
aattagaacg aaccaagctg cgcctgatca tagatcggaa gagcgtcgtg tagggaaaga       60
gt                                                                                       62

<210> SEQ ID NO 130
<211> LENGTH: 63
<212> TYPE: DNA
<213> ORGANISM: artificial sequence
<220> FEATURE:
<223> OTHER INFORMATION: locus probe

<400> SEQUENCE: 130
catttgagtg gtcgtttgtt tcgtgatcac taagatcgga agagcgtcgt gtagggaaag       60
agt                                                                                      63

<210> SEQ ID NO 131
<211> LENGTH: 61
<212> TYPE: DNA
<213> ORGANISM: artificial sequence
<220> FEATURE:
<223> OTHER INFORMATION: locus probe

<400> SEQUENCE: 131
agctgagccg gtctagaaac cggcgactcg agatcggaag agcgtcgtgt agggaaagag       60
t                                                                                        61

<210> SEQ ID NO 132
<211> LENGTH: 63
<212> TYPE: DNA
<213> ORGANISM: artificial sequence
<220> FEATURE:
<223> OTHER INFORMATION: locus probe

<400> SEQUENCE: 132
gcccctttat tttgatgttt gcgcctagat ctagatcgga agagcgtcgt gtagggaaag       60
agt                                                                                      63

<210> SEQ ID NO 133
<211> LENGTH: 62
<212> TYPE: DNA
<213> ORGANISM: artificial sequence
<220> FEATURE:

<223> OTHER INFORMATION: locus probe

<400> SEQUENCE: 133
catcatagca ctgtcagcat ggaatcgcgc tagatcggaa gagcgtcgtg tagggaaaga        60
gt                                                                        62

<210> SEQ ID NO 134
<211> LENGTH: 63
<212> TYPE: DNA
<213> ORGANISM: artificial sequence
<220> FEATURE:
<223> OTHER INFORMATION: locus probe

<400> SEQUENCE: 134
ctaatgactc ttgcaaggtg gaacactgat atagatcgga agagcgtcgt gtagggaaag        60
agt                                                                       63

<210> SEQ ID NO 135
<211> LENGTH: 64
<212> TYPE: DNA
<213> ORGANISM: artificial sequence
<220> FEATURE:
<223> OTHER INFORMATION: locus probe

<400> SEQUENCE: 135
ataaactaac gctcaattgc gtctcatctg tgcagatcgg aagagcgtcg tgtagggaaa        60
gagt                                                                      64

<210> SEQ ID NO 136
<211> LENGTH: 62
<212> TYPE: DNA
<213> ORGANISM: artificial sequence
<220> FEATURE:
<223> OTHER INFORMATION: locus probe

<400> SEQUENCE: 136
agagaggggc tagaaaggta gaaagtgtgc aagatcggaa gagcgtcgtg tagggaaaga        60
gt                                                                        62

<210> SEQ ID NO 137
<211> LENGTH: 62
<212> TYPE: DNA
<213> ORGANISM: artificial sequence
<220> FEATURE:
<223> OTHER INFORMATION: locus probe

<400> SEQUENCE: 137
cgtgatttcg cacaacgtta cagcactaca cagatcggaa gagcgtcgtg tagggaaaga        60
gt                                                                        62

<210> SEQ ID NO 138
<211> LENGTH: 62
<212> TYPE: DNA
<213> ORGANISM: artificial sequence
<220> FEATURE:
<223> OTHER INFORMATION: locus probe

<400> SEQUENCE: 138
ccgtccaaat aacatcagag gcccacgata tagatcggaa gagcgtcgtg tagggaaaga        60
gt                                                                        62

-continued

```
<210> SEQ ID NO 139
<211> LENGTH: 63
<212> TYPE: DNA
<213> ORGANISM: artificial sequence
<220> FEATURE:
<223> OTHER INFORMATION: locus probe

<400> SEQUENCE: 139
gcttcggcat ataagaccaa actgcacgct agagatcgga agagcgtcgt gtagggaaag      60
agt                                                                    63

<210> SEQ ID NO 140
<211> LENGTH: 62
<212> TYPE: DNA
<213> ORGANISM: artificial sequence
<220> FEATURE:
<223> OTHER INFORMATION: locus probe

<400> SEQUENCE: 140
gcctctactt ttccttgctc gtaatcgcat aagatcggaa gagcgtcgtg tagggaaaga      60
gt                                                                     62

<210> SEQ ID NO 141
<211> LENGTH: 63
<212> TYPE: DNA
<213> ORGANISM: artificial sequence
<220> FEATURE:
<223> OTHER INFORMATION: locus probe

<400> SEQUENCE: 141
ttcttgtcct tgttttcgat tgccgcatcg ctagatcgga agagcgtcgt gtagggaaag      60
agt                                                                    63

<210> SEQ ID NO 142
<211> LENGTH: 63
<212> TYPE: DNA
<213> ORGANISM: artificial sequence
<220> FEATURE:
<223> OTHER INFORMATION: locus probe

<400> SEQUENCE: 142
tgttctattc cagttggcat ggtatcatct acagatcgga agagcgtcgt gtagggaaag      60
agt                                                                    63

<210> SEQ ID NO 143
<211> LENGTH: 64
<212> TYPE: DNA
<213> ORGANISM: artificial sequence
<220> FEATURE:
<223> OTHER INFORMATION: locus probe

<400> SEQUENCE: 143
tggaaactaa cattctatcg gtaggtgcac tcaagatcgg aagagcgtcg tgtagggaaa      60
gagt                                                                   64

<210> SEQ ID NO 144
<211> LENGTH: 61
<212> TYPE: DNA
<213> ORGANISM: artificial sequence
<220> FEATURE:
<223> OTHER INFORMATION: locus probe

<400> SEQUENCE: 144
```

-continued

```
cacccgattc agaggtgcat cagcgatgta agatcggaag agcgtcgtgt agggaaagag        60
t                                                                        61

<210> SEQ ID NO 145
<211> LENGTH: 64
<212> TYPE: DNA
<213> ORGANISM: artificial sequence
<220> FEATURE:
<223> OTHER INFORMATION: locus probe

<400> SEQUENCE: 145
gtagagacag ttaagttcag ttcattatag cagagatcgg aagagcgtcg tgtagggaaa        60
gagt                                                                     64

<210> SEQ ID NO 146
<211> LENGTH: 61
<212> TYPE: DNA
<213> ORGANISM: artificial sequence
<220> FEATURE:
<223> OTHER INFORMATION: locus probe

<400> SEQUENCE: 146
tggcgaagat ggcaagagca gctgcgagca agatcggaag agcgtcgtgt agggaaagag        60
t                                                                        61

<210> SEQ ID NO 147
<211> LENGTH: 63
<212> TYPE: DNA
<213> ORGANISM: artificial sequence
<220> FEATURE:
<223> OTHER INFORMATION: locus probe

<400> SEQUENCE: 147
attgatggag agaagataca tgggagacta gaagatcgga agagcgtcgt gtagggaaag        60
agt                                                                      63

<210> SEQ ID NO 148
<211> LENGTH: 62
<212> TYPE: DNA
<213> ORGANISM: artificial sequence
<220> FEATURE:
<223> OTHER INFORMATION: locus probe

<400> SEQUENCE: 148
aagatcgaaa ttagtcccgg tggtcactca cagatcggaa gagcgtcgtg tagggaaaga        60
gt                                                                       62

<210> SEQ ID NO 149
<211> LENGTH: 61
<212> TYPE: DNA
<213> ORGANISM: artificial sequence
<220> FEATURE:
<223> OTHER INFORMATION: locus probe

<400> SEQUENCE: 149
ggatcagcgc gtgaagcatt catcagatgt agatcggaag agcgtcgtgt agggaaagag        60
t                                                                        61

<210> SEQ ID NO 150
<211> LENGTH: 62
<212> TYPE: DNA
<213> ORGANISM: artificial sequence
```

```
<220> FEATURE:
<223> OTHER INFORMATION: locus probe

<400> SEQUENCE: 150
gtttagaatg gtcagcttcc ctgatctgtc aagatcggaa gagcgtcgtg tagggaaaga      60
gt                                                                     62

<210> SEQ ID NO 151
<211> LENGTH: 62
<212> TYPE: DNA
<213> ORGANISM: artificial sequence
<220> FEATURE:
<223> OTHER INFORMATION: locus probe

<400> SEQUENCE: 151
tgtgctcact ggttcttggt tcgcagtact gagatcggaa gagcgtcgtg tagggaaaga      60
gt                                                                     62

<210> SEQ ID NO 152
<211> LENGTH: 62
<212> TYPE: DNA
<213> ORGANISM: artificial sequence
<220> FEATURE:
<223> OTHER INFORMATION: locus probe

<400> SEQUENCE: 152
ctacatcctt agatgtggcg acatcagtga gagatcggaa gagcgtcgtg tagggaaaga      60
gt                                                                     62

<210> SEQ ID NO 153
<211> LENGTH: 63
<212> TYPE: DNA
<213> ORGANISM: artificial sequence
<220> FEATURE:
<223> OTHER INFORMATION: locus probe

<400> SEQUENCE: 153
tacgttcaag gctgactgga atttacgcat caagatcgga agagcgtcgt gtagggaaag      60
agt                                                                    63

<210> SEQ ID NO 154
<211> LENGTH: 63
<212> TYPE: DNA
<213> ORGANISM: artificial sequence
<220> FEATURE:
<223> OTHER INFORMATION: locus probe

<400> SEQUENCE: 154
tctcccatcg aaaaatcact atcccgtctc atagatcgga agagcgtcgt gtagggaaag      60
agt                                                                    63

<210> SEQ ID NO 155
<211> LENGTH: 65
<212> TYPE: DNA
<213> ORGANISM: artificial sequence
<220> FEATURE:
<223> OTHER INFORMATION: locus probe

<400> SEQUENCE: 155
tgctttattt tgatagctgc aacttggact cagaagatcg gaagagcgtc gtgtagggaa      60
agagt                                                                  65
```

-continued

```
<210> SEQ ID NO 156
<211> LENGTH: 63
<212> TYPE: DNA
<213> ORGANISM: artificial sequence
<220> FEATURE:
<223> OTHER INFORMATION: locus probe

<400> SEQUENCE: 156
ctgccttgtt cagtctgcta attatacaga gtagatcgga agagcgtcgt gtagggaaag      60
agt                                                                     63

<210> SEQ ID NO 157
<211> LENGTH: 64
<212> TYPE: DNA
<213> ORGANISM: artificial sequence
<220> FEATURE:
<223> OTHER INFORMATION: locus probe

<400> SEQUENCE: 157
aacaatgaag ttgcagcaaa cacaaagtca cgcagatcgg aagagcgtcg tgtagggaaa      60
gagt                                                                    64

<210> SEQ ID NO 158
<211> LENGTH: 62
<212> TYPE: DNA
<213> ORGANISM: artificial sequence
<220> FEATURE:
<223> OTHER INFORMATION: locus probe

<400> SEQUENCE: 158
cgtttctgct aggaggacca tactctgcta gagatcggaa gagcgtcgtg tagggaaaga      60
gt                                                                      62

<210> SEQ ID NO 159
<211> LENGTH: 64
<212> TYPE: DNA
<213> ORGANISM: artificial sequence
<220> FEATURE:
<223> OTHER INFORMATION: locus probe

<400> SEQUENCE: 159
gccacttaca taatcatagc taatcatctc tcgagatcgg aagagcgtcg tgtagggaaa      60
gagt                                                                    64

<210> SEQ ID NO 160
<211> LENGTH: 63
<212> TYPE: DNA
<213> ORGANISM: artificial sequence
<220> FEATURE:
<223> OTHER INFORMATION: locus probe

<400> SEQUENCE: 160
agaggcaata ttctacacgt gcaagagaca cgagatcgga agagcgtcgt gtagggaaag      60
agt                                                                     63

<210> SEQ ID NO 161
<211> LENGTH: 60
<212> TYPE: DNA
<213> ORGANISM: artificial sequence
<220> FEATURE:
<223> OTHER INFORMATION: locus probe

<400> SEQUENCE: 161
```
gagcgccggt tttggaacca gtgtagctca gatcggaaga gcgtcgtgta gggaaagagt          60

<210> SEQ ID NO 162
<211> LENGTH: 63
<212> TYPE: DNA
<213> ORGANISM: artificial sequence
<220> FEATURE:
<223> OTHER INFORMATION: locus probe

<400> SEQUENCE: 162
gtgctttcgg agttattgtt tggagctcac gtagatcgga agagcgtcgt gtagggaaag          60
agt                                                                        63

<210> SEQ ID NO 163
<211> LENGTH: 59
<212> TYPE: DNA
<213> ORGANISM: artificial sequence
<220> FEATURE:
<223> OTHER INFORMATION: locus probe

<400> SEQUENCE: 163
ggcgaggacg acccgtagca gcgatatgag atcggaagag cgtcgtgtag ggaaagagt           59

<210> SEQ ID NO 164
<211> LENGTH: 62
<212> TYPE: DNA
<213> ORGANISM: artificial sequence
<220> FEATURE:
<223> OTHER INFORMATION: locus probe

<400> SEQUENCE: 164
agccgtgttg catcatgctt ctactcgaga gagatcggaa gagcgtcgtg tagggaaaga          60
gt                                                                         62

<210> SEQ ID NO 165
<211> LENGTH: 63
<212> TYPE: DNA
<213> ORGANISM: artificial sequence
<220> FEATURE:
<223> OTHER INFORMATION: locus probe

<400> SEQUENCE: 165
tcttacgatc ttgtcaaaca gctcgagatg tcagatcgga agagcgtcgt gtagggaaag          60
agt                                                                        63

<210> SEQ ID NO 166
<211> LENGTH: 63
<212> TYPE: DNA
<213> ORGANISM: artificial sequence
<220> FEATURE:
<223> OTHER INFORMATION: locus probe

<400> SEQUENCE: 166
agagaaacaa cagatcagac catgagcgtg agagatcgga agagcgtcgt gtagggaaag          60
agt                                                                        63

<210> SEQ ID NO 167
<211> LENGTH: 63
<212> TYPE: DNA
<213> ORGANISM: artificial sequence
<220> FEATURE:
<223> OTHER INFORMATION: locus probe

```
<400> SEQUENCE: 167
cttggcgctg ctcttgtatt ttttgacgct atagatcgga agagcgtcgt gtagggaaag        60
agt                                                                       63

<210> SEQ ID NO 168
<211> LENGTH: 61
<212> TYPE: DNA
<213> ORGANISM: artificial sequence
<220> FEATURE:
<223> OTHER INFORMATION: locus probe

<400> SEQUENCE: 168
ggcactcatg catgatcctc ctcgactgcg agatcggaag agcgtcgtgt agggaaagag        60
t                                                                         61

<210> SEQ ID NO 169
<211> LENGTH: 62
<212> TYPE: DNA
<213> ORGANISM: artificial sequence
<220> FEATURE:
<223> OTHER INFORMATION: locus probe

<400> SEQUENCE: 169
actagtgctt gccagtattc cagtactgat gagatcggaa gagcgtcgtg tagggaaaga        60
gt                                                                        62

<210> SEQ ID NO 170
<211> LENGTH: 62
<212> TYPE: DNA
<213> ORGANISM: artificial sequence
<220> FEATURE:
<223> OTHER INFORMATION: locus probe

<400> SEQUENCE: 170
ttgcacctgc agcctatcta ttcactgtac aagatcggaa gagcgtcgtg tagggaaaga        60
gt                                                                        62

<210> SEQ ID NO 171
<211> LENGTH: 63
<212> TYPE: DNA
<213> ORGANISM: artificial sequence
<220> FEATURE:
<223> OTHER INFORMATION: locus probe

<400> SEQUENCE: 171
tccgatgtgc taaattcatc acccgtagta caagatcgga agagcgtcgt gtagggaaag        60
agt                                                                       63

<210> SEQ ID NO 172
<211> LENGTH: 64
<212> TYPE: DNA
<213> ORGANISM: artificial sequence
<220> FEATURE:
<223> OTHER INFORMATION: locus probe

<400> SEQUENCE: 172
ctacctttta tgtccttact actgcgacac gacagatcgg aagagcgtcg tgtagggaaa        60
gagt                                                                      64

<210> SEQ ID NO 173
<211> LENGTH: 63
```

-continued

```
<212> TYPE: DNA
<213> ORGANISM: artificial sequence
<220> FEATURE:
<223> OTHER INFORMATION: locus probe

<400> SEQUENCE: 173
tatttggatg attctgagtg gggcgcgcgt gcagatcgga agagcgtcgt gtagggaaag        60
agt                                                                       63

<210> SEQ ID NO 174
<211> LENGTH: 63
<212> TYPE: DNA
<213> ORGANISM: artificial sequence
<220> FEATURE:
<223> OTHER INFORMATION: locus probe

<400> SEQUENCE: 174
aaggagttag agagacaagg actacacgtg caagatcgga agagcgtcgt gtagggaaag        60
agt                                                                       63

<210> SEQ ID NO 175
<211> LENGTH: 61
<212> TYPE: DNA
<213> ORGANISM: artificial sequence
<220> FEATURE:
<223> OTHER INFORMATION: locus probe

<400> SEQUENCE: 175
cagcctgggg aacctagttt tgctactata agatcggaag agcgtcgtgt agggaaagag        60
t                                                                         61

<210> SEQ ID NO 176
<211> LENGTH: 63
<212> TYPE: DNA
<213> ORGANISM: artificial sequence
<220> FEATURE:
<223> OTHER INFORMATION: locus probe

<400> SEQUENCE: 176
cgcagcaata cgtctcaaaa tctactgcgt cgagatcgga agagcgtcgt gtagggaaag        60
agt                                                                       63

<210> SEQ ID NO 177
<211> LENGTH: 62
<212> TYPE: DNA
<213> ORGANISM: artificial sequence
<220> FEATURE:
<223> OTHER INFORMATION: locus probe

<400> SEQUENCE: 177
tagttccatt agcagcctgt ggaagtatat aagatcggaa gagcgtcgtg tagggaaaga        60
gt                                                                        62

<210> SEQ ID NO 178
<211> LENGTH: 62
<212> TYPE: DNA
<213> ORGANISM: artificial sequence
<220> FEATURE:
<223> OTHER INFORMATION: locus probe

<400> SEQUENCE: 178
gtccatcttc catactccca ctttgacagt cagatcggaa gagcgtcgtg tagggaaaga        60
```

-continued

```
gt                                                                                62

<210> SEQ ID NO 179
<211> LENGTH: 61
<212> TYPE: DNA
<213> ORGANISM: artificial sequence
<220> FEATURE:
<223> OTHER INFORMATION: locus probe

<400> SEQUENCE: 179
gcgacagctt tgcgagtcct tcatcgcagc agatcggaag agcgtcgtgt agggaaagag        60
t                                                                                 61

<210> SEQ ID NO 180
<211> LENGTH: 63
<212> TYPE: DNA
<213> ORGANISM: artificial sequence
<220> FEATURE:
<223> OTHER INFORMATION: locus probe

<400> SEQUENCE: 180
ttcaccattc gccaaactat agcaacactc tgagatcgga agagcgtcgt gtagggaaag        60
agt                                                                              63

<210> SEQ ID NO 181
<211> LENGTH: 63
<212> TYPE: DNA
<213> ORGANISM: artificial sequence
<220> FEATURE:
<223> OTHER INFORMATION: locus probe

<400> SEQUENCE: 181
aataagcagc tgtcaaatca gcacctgctg taagatcgga agagcgtcgt gtagggaaag        60
agt                                                                              63

<210> SEQ ID NO 182
<211> LENGTH: 61
<212> TYPE: DNA
<213> ORGANISM: artificial sequence
<220> FEATURE:
<223> OTHER INFORMATION: locus probe

<400> SEQUENCE: 182
gtggacaagg gtacagggaa gagagcacac agatcggaag agcgtcgtgt agggaaagag        60
t                                                                                 61

<210> SEQ ID NO 183
<211> LENGTH: 62
<212> TYPE: DNA
<213> ORGANISM: artificial sequence
<220> FEATURE:
<223> OTHER INFORMATION: locus probe

<400> SEQUENCE: 183
aagcagctca gagttggatt cctgagctct gagatcggaa gagcgtcgtg tagggaaaga        60
gt                                                                                62

<210> SEQ ID NO 184
<211> LENGTH: 61
<212> TYPE: DNA
<213> ORGANISM: artificial sequence
<220> FEATURE:
<223> OTHER INFORMATION: locus probe
```

-continued

<400> SEQUENCE: 184
gaccgtctaa acagctgctc tcgtatcacg agatcggaag agcgtcgtgt agggaaagag        60
t                                                                                                          61

<210> SEQ ID NO 185
<211> LENGTH: 63
<212> TYPE: DNA
<213> ORGANISM: artificial sequence
<220> FEATURE:
<223> OTHER INFORMATION: locus probe

<400> SEQUENCE: 185
gatgtgaggt aatctgaata cagcgctgac taagatcgga agagcgtcgt gtagggaaag        60
agt                                                                                                        63

<210> SEQ ID NO 186
<211> LENGTH: 64
<212> TYPE: DNA
<213> ORGANISM: artificial sequence
<220> FEATURE:
<223> OTHER INFORMATION: locus probe

<400> SEQUENCE: 186
tgttcctttc atatggaaaa acagctctgt actagatcgg aagagcgtcg tgtagggaaa        60
gagt                                                                                                       64

<210> SEQ ID NO 187
<211> LENGTH: 62
<212> TYPE: DNA
<213> ORGANISM: artificial sequence
<220> FEATURE:
<223> OTHER INFORMATION: locus probe

<400> SEQUENCE: 187
caccgaaaga tttggacagg agtgagcgca gagatcggaa gagcgtcgtg tagggaaaga        60
gt                                                                                                          62

<210> SEQ ID NO 188
<211> LENGTH: 63
<212> TYPE: DNA
<213> ORGANISM: artificial sequence
<220> FEATURE:
<223> OTHER INFORMATION: locus probe

<400> SEQUENCE: 188
ggaatagaaa atcgcagcat cactacgact gtagatcgga agagcgtcgt gtagggaaag        60
agt                                                                                                        63

<210> SEQ ID NO 189
<211> LENGTH: 61
<212> TYPE: DNA
<213> ORGANISM: artificial sequence
<220> FEATURE:
<223> OTHER INFORMATION: locus probe

<400> SEQUENCE: 189
gagattgcga gatgatgagc cctcgagtgt agatcggaag agcgtcgtgt agggaaagag        60
t                                                                                                          61

<210> SEQ ID NO 190

```
<211> LENGTH: 60
<212> TYPE: DNA
<213> ORGANISM: artificial sequence
<220> FEATURE:
<223> OTHER INFORMATION: locus probe

<400> SEQUENCE: 190
ctctggcacc tgcagcactt cgctctacaa gatcggaaga gcgtcgtgta gggaaagagt        60

<210> SEQ ID NO 191
<211> LENGTH: 61
<212> TYPE: DNA
<213> ORGANISM: artificial sequence
<220> FEATURE:
<223> OTHER INFORMATION: locus probe

<400> SEQUENCE: 191
tggaataact ggtctctgcc ggcatactat agatcggaag agcgtcgtgt agggaaagag        60
t                                                                        61

<210> SEQ ID NO 192
<211> LENGTH: 62
<212> TYPE: DNA
<213> ORGANISM: artificial sequence
<220> FEATURE:
<223> OTHER INFORMATION: locus probe

<400> SEQUENCE: 192
cggcagcacc tacatcatac taagcgatgc gagatcggaa gagcgtcgtg tagggaaaga        60
gt                                                                       62

<210> SEQ ID NO 193
<211> LENGTH: 62
<212> TYPE: DNA
<213> ORGANISM: artificial sequence
<220> FEATURE:
<223> OTHER INFORMATION: locus probe

<400> SEQUENCE: 193
agtttgacgc ttgcattgcc atgactacgt aagatcggaa gagcgtcgtg tagggaaaga        60
gt                                                                       62

<210> SEQ ID NO 194
<211> LENGTH: 62
<212> TYPE: DNA
<213> ORGANISM: artificial sequence
<220> FEATURE:
<223> OTHER INFORMATION: locus probe

<400> SEQUENCE: 194
tctctgtttg aatccagctg tgcacgtgtg cagatcggaa gagcgtcgtg tagggaaaga        60
gt                                                                       62

<210> SEQ ID NO 195
<211> LENGTH: 62
<212> TYPE: DNA
<213> ORGANISM: artificial sequence
<220> FEATURE:
<223> OTHER INFORMATION: locus probe

<400> SEQUENCE: 195
gataatggtc cggtggctca ttgatatctc tagatcggaa gagcgtcgtg tagggaaaga        60
gt                                                                       62
```

<210> SEQ ID NO 196
<211> LENGTH: 63
<212> TYPE: DNA
<213> ORGANISM: artificial sequence
<220> FEATURE:
<223> OTHER INFORMATION: locus probe

<400> SEQUENCE: 196
ggggacatta tcaacatgat gtgggtgagt cgagatcgga agagcgtcgt gtagggaaag      60
agt                                                                    63

<210> SEQ ID NO 197
<211> LENGTH: 62
<212> TYPE: DNA
<213> ORGANISM: artificial sequence
<220> FEATURE:
<223> OTHER INFORMATION: locus probe

<400> SEQUENCE: 197
gtgatgagtg tttcgcgaac caacgcagcg tagatcggaa gagcgtcgtg tagggaaaga      60
gt                                                                     62

<210> SEQ ID NO 198
<211> LENGTH: 61
<212> TYPE: DNA
<213> ORGANISM: artificial sequence
<220> FEATURE:
<223> OTHER INFORMATION: locus probe

<400> SEQUENCE: 198
catgtaccct gactaccctt gctctgtgat agatcggaag agcgtcgtgt agggaaagag      60
t                                                                      61

<210> SEQ ID NO 199
<211> LENGTH: 61
<212> TYPE: DNA
<213> ORGANISM: artificial sequence
<220> FEATURE:
<223> OTHER INFORMATION: locus probe

<400> SEQUENCE: 199
gctgttagct aggctgcttg tgatgtatat agatcggaag agcgtcgtgt agggaaagag      60
t                                                                      61

<210> SEQ ID NO 200
<211> LENGTH: 64
<212> TYPE: DNA
<213> ORGANISM: artificial sequence
<220> FEATURE:
<223> OTHER INFORMATION: locus probe

<400> SEQUENCE: 200
gcattttgtt gtgcttgaac atgaaatcac tcaagatcgg aagagcgtcg tgtagggaaa      60
gagt                                                                   64

<210> SEQ ID NO 201
<211> LENGTH: 60
<212> TYPE: DNA
<213> ORGANISM: artificial sequence
<220> FEATURE:
<223> OTHER INFORMATION: locus probe

```
<400> SEQUENCE: 201
ttggtgtcca gcttgggggc agacgatcta gatcggaaga gcgtcgtgta gggaaagagt      60

<210> SEQ ID NO 202
<211> LENGTH: 64
<212> TYPE: DNA
<213> ORGANISM: artificial sequence
<220> FEATURE:
<223> OTHER INFORMATION: locus probe

<400> SEQUENCE: 202
tccatttact gatacttgtg agcttgtatg actagatcgg aagagcgtcg tgtagggaaa      60
gagt                                                                   64

<210> SEQ ID NO 203
<211> LENGTH: 62
<212> TYPE: DNA
<213> ORGANISM: artificial sequence
<220> FEATURE:
<223> OTHER INFORMATION: locus probe

<400> SEQUENCE: 203
caaccgatgt gcattgaaca tgggctcgct aagatcggaa gagcgtcgtg tagggaaaga      60
gt                                                                     62

<210> SEQ ID NO 204
<211> LENGTH: 63
<212> TYPE: DNA
<213> ORGANISM: artificial sequence
<220> FEATURE:
<223> OTHER INFORMATION: locus probe

<400> SEQUENCE: 204
ggtgaaagat gcttacagct catcgcatac gtagatcgga agagcgtcgt gtagggaaag      60
agt                                                                    63

<210> SEQ ID NO 205
<211> LENGTH: 63
<212> TYPE: DNA
<213> ORGANISM: artificial sequence
<220> FEATURE:
<223> OTHER INFORMATION: locus probe

<400> SEQUENCE: 205
ttgtcagatt gcctagatgt tagctgctgc atagatcgga agagcgtcgt gtagggaaag      60
agt                                                                    63

<210> SEQ ID NO 206
<211> LENGTH: 63
<212> TYPE: DNA
<213> ORGANISM: artificial sequence
<220> FEATURE:
<223> OTHER INFORMATION: locus probe

<400> SEQUENCE: 206
cagttgttga ttcaactctg cgtgcactca taagatcgga agagcgtcgt gtagggaaag      60
agt                                                                    63

<210> SEQ ID NO 207
<211> LENGTH: 62
<212> TYPE: DNA
<213> ORGANISM: artificial sequence
```

```
<220> FEATURE:
<223> OTHER INFORMATION: locus probe

<400> SEQUENCE: 207
gacaggccct gtacctattg atgcagtcta cagatcggaa gagcgtcgtg tagggaaaga      60
gt                                                                     62

<210> SEQ ID NO 208
<211> LENGTH: 64
<212> TYPE: DNA
<213> ORGANISM: artificial sequence
<220> FEATURE:
<223> OTHER INFORMATION: locus probe

<400> SEQUENCE: 208
aactaaattt cttgccaacc tgcaggagta gcgagatcgg aagagcgtcg tgtagggaaa      60
gagt                                                                   64

<210> SEQ ID NO 209
<211> LENGTH: 64
<212> TYPE: DNA
<213> ORGANISM: artificial sequence
<220> FEATURE:
<223> OTHER INFORMATION: locus probe

<400> SEQUENCE: 209
tttttcacag ttgcctgctt tttggcagac tgtagatcgg aagagcgtcg tgtagggaaa      60
gagt                                                                   64

<210> SEQ ID NO 210
<211> LENGTH: 62
<212> TYPE: DNA
<213> ORGANISM: artificial sequence
<220> FEATURE:
<223> OTHER INFORMATION: locus probe

<400> SEQUENCE: 210
gtaggccagt ctgttacaga caaacgcgtc tagatcggaa gagcgtcgtg tagggaaaga      60
gt                                                                     62

<210> SEQ ID NO 211
<211> LENGTH: 62
<212> TYPE: DNA
<213> ORGANISM: artificial sequence
<220> FEATURE:
<223> OTHER INFORMATION: locus probe

<400> SEQUENCE: 211
tatccaagct tccaaggtga ggtagatcga tagatcggaa gagcgtcgtg tagggaaaga      60
gt                                                                     62

<210> SEQ ID NO 212
<211> LENGTH: 62
<212> TYPE: DNA
<213> ORGANISM: artificial sequence
<220> FEATURE:
<223> OTHER INFORMATION: locus probe

<400> SEQUENCE: 212
gttccacatg gagtgaacag aactgcagta cagatcggaa gagcgtcgtg tagggaaaga      60
gt                                                                     62
```

-continued

<210> SEQ ID NO 213
<211> LENGTH: 61
<212> TYPE: DNA
<213> ORGANISM: artificial sequence
<220> FEATURE:
<223> OTHER INFORMATION: locus probe

<400> SEQUENCE: 213
cagagcttga aggctacttg ggtcgagcac agatcggaag agcgtcgtgt agggaaagag        60
t                                                                       61

<210> SEQ ID NO 214
<211> LENGTH: 63
<212> TYPE: DNA
<213> ORGANISM: artificial sequence
<220> FEATURE:
<223> OTHER INFORMATION: locus probe

<400> SEQUENCE: 214
atcagcgaag gaaatatcag gtactactga caagatcgga agagcgtcgt gtagggaaag        60
agt                                                                     63

<210> SEQ ID NO 215
<211> LENGTH: 62
<212> TYPE: DNA
<213> ORGANISM: artificial sequence
<220> FEATURE:
<223> OTHER INFORMATION: locus probe

<400> SEQUENCE: 215
caggaatttg tccctgatga gcgtgatgct cagatcggaa gagcgtcgtg tagggaaaga        60
gt                                                                      62

<210> SEQ ID NO 216
<211> LENGTH: 61
<212> TYPE: DNA
<213> ORGANISM: artificial sequence
<220> FEATURE:
<223> OTHER INFORMATION: locus probe

<400> SEQUENCE: 216
tgccgcaaat gatgaggcct ggcgtctcga agatcggaag agcgtcgtgt agggaaagag        60
t                                                                       61

<210> SEQ ID NO 217
<211> LENGTH: 62
<212> TYPE: DNA
<213> ORGANISM: artificial sequence
<220> FEATURE:
<223> OTHER INFORMATION: locus probe

<400> SEQUENCE: 217
cacgatgtag tttcagtgtg ctgtcgcatc gagatcggaa gagcgtcgtg tagggaaaga        60
gt                                                                      62

<210> SEQ ID NO 218
<211> LENGTH: 62
<212> TYPE: DNA
<213> ORGANISM: artificial sequence
<220> FEATURE:
<223> OTHER INFORMATION: locus probe

<400> SEQUENCE: 218

```
aatggacgcg agatcacgag tacctgatat aagatcggaa gagcgtcgtg tagggaaaga        60
gt                                                                        62
```

<210> SEQ ID NO 219
<211> LENGTH: 63
<212> TYPE: DNA
<213> ORGANISM: artificial sequence
<220> FEATURE:
<223> OTHER INFORMATION: locus probe

<400> SEQUENCE: 219

```
ataacagcgg acaacacgat gtacatatgc atagatcgga agagcgtcgt gtagggaaag        60
agt                                                                       63
```

<210> SEQ ID NO 220
<211> LENGTH: 61
<212> TYPE: DNA
<213> ORGANISM: artificial sequence
<220> FEATURE:
<223> OTHER INFORMATION: locus probe

<400> SEQUENCE: 220

```
gcatgtgact gctgcctgac taagacgaca agatcggaag agcgtcgtgt agggaaagag        60
t                                                                         61
```

<210> SEQ ID NO 221
<211> LENGTH: 62
<212> TYPE: DNA
<213> ORGANISM: artificial sequence
<220> FEATURE:
<223> OTHER INFORMATION: locus probe

<400> SEQUENCE: 221

```
gatgtgttat tagccctggc tgcgtcagta cagatcggaa gagcgtcgtg tagggaaaga        60
gt                                                                        62
```

<210> SEQ ID NO 222
<211> LENGTH: 63
<212> TYPE: DNA
<213> ORGANISM: artificial sequence
<220> FEATURE:
<223> OTHER INFORMATION: locus probe

<400> SEQUENCE: 222

```
aatgttacag cagataaatc cgcggtgcta gtagatcgga agagcgtcgt gtagggaaag        60
agt                                                                       63
```

<210> SEQ ID NO 223
<211> LENGTH: 61
<212> TYPE: DNA
<213> ORGANISM: artificial sequence
<220> FEATURE:
<223> OTHER INFORMATION: locus probe

<400> SEQUENCE: 223

```
aaaggctggt gtctgagaag gcctgacgta agatcggaag agcgtcgtgt agggaaagag        60
t                                                                         61
```

<210> SEQ ID NO 224
<211> LENGTH: 64
<212> TYPE: DNA

```
<213> ORGANISM: artificial sequence
<220> FEATURE:
<223> OTHER INFORMATION: locus probe

<400> SEQUENCE: 224
tgcatacctt ccaatgaaag ctatagtctc gatagatcgg aagagcgtcg tgtagggaaa      60
gagt                                                                     64

<210> SEQ ID NO 225
<211> LENGTH: 64
<212> TYPE: DNA
<213> ORGANISM: artificial sequence
<220> FEATURE:
<223> OTHER INFORMATION: locus probe

<400> SEQUENCE: 225
tacaataagc aaacacaaat cccgggacgt agaagatcgg aagagcgtcg tgtagggaaa      60
gagt                                                                     64

<210> SEQ ID NO 226
<211> LENGTH: 62
<212> TYPE: DNA
<213> ORGANISM: artificial sequence
<220> FEATURE:
<223> OTHER INFORMATION: locus probe

<400> SEQUENCE: 226
agtaatcctc ctcagctagt ctgcgacatg cagatcggaa gagcgtcgtg tagggaaaga      60
gt                                                                       62

<210> SEQ ID NO 227
<211> LENGTH: 61
<212> TYPE: DNA
<213> ORGANISM: artificial sequence
<220> FEATURE:
<223> OTHER INFORMATION: locus probe

<400> SEQUENCE: 227
cacccttacc cgggaactaa gcacacgcta agatcggaag agcgtcgtgt agggaaagag      60
t                                                                        61

<210> SEQ ID NO 228
<211> LENGTH: 64
<212> TYPE: DNA
<213> ORGANISM: artificial sequence
<220> FEATURE:
<223> OTHER INFORMATION: locus probe

<400> SEQUENCE: 228
tctaatcaat cctagttacc atggctagtg ctcagatcgg aagagcgtcg tgtagggaaa      60
gagt                                                                     64

<210> SEQ ID NO 229
<211> LENGTH: 62
<212> TYPE: DNA
<213> ORGANISM: artificial sequence
<220> FEATURE:
<223> OTHER INFORMATION: locus probe

<400> SEQUENCE: 229
ttgcgaataa cgcatctgct gggcgatcga gagatcggaa gagcgtcgtg tagggaaaga      60
gt                                                                       62
```

<210> SEQ ID NO 230
<211> LENGTH: 63
<212> TYPE: DNA
<213> ORGANISM: artificial sequence
<220> FEATURE:
<223> OTHER INFORMATION: locus probe

<400> SEQUENCE: 230
tgataaactg taacgcatac cggtctcacg agagatcgga agagcgtcgt gtagggaaag        60
agt                                                                     63

<210> SEQ ID NO 231
<211> LENGTH: 61
<212> TYPE: DNA
<213> ORGANISM: artificial sequence
<220> FEATURE:
<223> OTHER INFORMATION: locus probe

<400> SEQUENCE: 231
ggaatagggg ctgcctgtga ttgtactctg agatcggaag agcgtcgtgt agggaaagag        60
t                                                                       61

<210> SEQ ID NO 232
<211> LENGTH: 64
<212> TYPE: DNA
<213> ORGANISM: artificial sequence
<220> FEATURE:
<223> OTHER INFORMATION: locus probe

<400> SEQUENCE: 232
attaagcatg gagtgtcatc catacctaca tcgagatcgg aagagcgtcg tgtagggaaa        60
gagt                                                                    64

<210> SEQ ID NO 233
<211> LENGTH: 62
<212> TYPE: DNA
<213> ORGANISM: artificial sequence
<220> FEATURE:
<223> OTHER INFORMATION: locus probe

<400> SEQUENCE: 233
caggatcatg ttccatgcca tgctgtgcat gagatcggaa gagcgtcgtg tagggaaaga        60
gt                                                                      62

<210> SEQ ID NO 234
<211> LENGTH: 62
<212> TYPE: DNA
<213> ORGANISM: artificial sequence
<220> FEATURE:
<223> OTHER INFORMATION: locus probe

<400> SEQUENCE: 234
ctcaaagtca tacaccgaag cgcgtgcacg tagatcggaa gagcgtcgtg tagggaaaga        60
gt                                                                      62

<210> SEQ ID NO 235
<211> LENGTH: 62
<212> TYPE: DNA
<213> ORGANISM: artificial sequence
<220> FEATURE:
<223> OTHER INFORMATION: locus probe

<400> SEQUENCE: 235
gctatctgca gtcctagtcg ttcgcacaga gagatcggaa gagcgtcgtg tagggaaaga     60
gt                                                                    62

<210> SEQ ID NO 236
<211> LENGTH: 63
<212> TYPE: DNA
<213> ORGANISM: artificial sequence
<220> FEATURE:
<223> OTHER INFORMATION: locus probe

<400> SEQUENCE: 236
tagttgctgt acttgttgag ctgtcatgcg atagatcgga agagcgtcgt gtagggaaag     60
agt                                                                   63

<210> SEQ ID NO 237
<211> LENGTH: 64
<212> TYPE: DNA
<213> ORGANISM: artificial sequence
<220> FEATURE:
<223> OTHER INFORMATION: locus probe

<400> SEQUENCE: 237
tataccctca gcttatatgt gtagttctga tacagatcgg aagagcgtcg tgtagggaaa     60
gagt                                                                  64

<210> SEQ ID NO 238
<211> LENGTH: 64
<212> TYPE: DNA
<213> ORGANISM: artificial sequence
<220> FEATURE:
<223> OTHER INFORMATION: locus probe

<400> SEQUENCE: 238
gtttgtgtgt ttatgtgatg cgaatgcgat cagagatcgg aagagcgtcg tgtagggaaa     60
gagt                                                                  64

<210> SEQ ID NO 239
<211> LENGTH: 62
<212> TYPE: DNA
<213> ORGANISM: artificial sequence
<220> FEATURE:
<223> OTHER INFORMATION: locus probe

<400> SEQUENCE: 239
gctacaaatg gcttcagcag tgtgcgcaca tagatcggaa gagcgtcgtg tagggaaaga     60
gt                                                                    62

<210> SEQ ID NO 240
<211> LENGTH: 63
<212> TYPE: DNA
<213> ORGANISM: artificial sequence
<220> FEATURE:
<223> OTHER INFORMATION: locus probe

<400> SEQUENCE: 240
gctgcgatta ttttgtgtgg tcagagatct gtagatcgga agagcgtcgt gtagggaaag     60
agt                                                                   63

<210> SEQ ID NO 241
<211> LENGTH: 64

```
<212> TYPE: DNA
<213> ORGANISM: artificial sequence
<220> FEATURE:
<223> OTHER INFORMATION: locus probe

<400> SEQUENCE: 241 gactttttgat ttgcttccag taaaggatcg tgcagatcgg aagagcgtcg tgtagggaaa    60
gagt                                                                  64

<210> SEQ ID NO 242
<211> LENGTH: 62
<212> TYPE: DNA
<213> ORGANISM: artificial sequence
<220> FEATURE:
<223> OTHER INFORMATION: locus probe

<400> SEQUENCE: 242
tcatgtgatg tgcaggaacc tgaacgcgtg aagatcggaa gagcgtcgtg tagggaaaga    60
gt                                                                    62

<210> SEQ ID NO 243
<211> LENGTH: 60
<212> TYPE: DNA
<213> ORGANISM: artificial sequence
<220> FEATURE:
<223> OTHER INFORMATION: locus probe

<400> SEQUENCE: 243
atgacaccga ggagggcatc gcgcgcgcaa gatcggaaga gcgtcgtgta gggaaagagt    60

<210> SEQ ID NO 244
<211> LENGTH: 65
<212> TYPE: DNA
<213> ORGANISM: artificial sequence
<220> FEATURE:
<223> OTHER INFORMATION: locus probe

<400> SEQUENCE: 244
atttgatcgt aattagttag ctgaccgtga tcacagatcg gaagagcgtc gtgtagggaa    60
agagt                                                                 65

<210> SEQ ID NO 245
<211> LENGTH: 63
<212> TYPE: DNA
<213> ORGANISM: artificial sequence
<220> FEATURE:
<223> OTHER INFORMATION: locus probe

<400> SEQUENCE: 245
ttgttttgtt ggtgaagcaa cctggtgagc tcagatcgga agagcgtcgt gtagggaaag    60
agt                                                                   63

<210> SEQ ID NO 246
<211> LENGTH: 63
<212> TYPE: DNA
<213> ORGANISM: artificial sequence
<220> FEATURE:
<223> OTHER INFORMATION: locus probe

<400> SEQUENCE: 246
gcgcaatcaa agtcaaaacc tagccgcgac tgagatcgga agagcgtcgt gtagggaaag    60
agt                                                                   63
```

```
<210> SEQ ID NO 247
<211> LENGTH: 62
<212> TYPE: DNA
<213> ORGANISM: artificial sequence
<220> FEATURE:
<223> OTHER INFORMATION: locus probe

<400> SEQUENCE: 247
gtggctctct tcgagctcaa taaatcatgc aagatcggaa gagcgtcgtg tagggaaaga      60
gt                                                                    62

<210> SEQ ID NO 248
<211> LENGTH: 62
<212> TYPE: DNA
<213> ORGANISM: artificial sequence
<220> FEATURE:
<223> OTHER INFORMATION: locus probe

<400> SEQUENCE: 248
gatgccattg gtgtgaatca ggccgtgtct cagatcggaa gagcgtcgtg tagggaaaga      60
gt                                                                    62

<210> SEQ ID NO 249
<211> LENGTH: 63
<212> TYPE: DNA
<213> ORGANISM: artificial sequence
<220> FEATURE:
<223> OTHER INFORMATION: locus probe

<400> SEQUENCE: 249
gaatcccata tagaagaggg gaagagagag caagatcgga agagcgtcgt gtagggaaag      60
agt                                                                   63

<210> SEQ ID NO 250
<211> LENGTH: 62
<212> TYPE: DNA
<213> ORGANISM: artificial sequence
<220> FEATURE:
<223> OTHER INFORMATION: locus probe

<400> SEQUENCE: 250
cgacacatgc cttgctgcaa atgagtacgc aagatcggaa gagcgtcgtg tagggaaaga      60
gt                                                                    62

<210> SEQ ID NO 251
<211> LENGTH: 61
<212> TYPE: DNA
<213> ORGANISM: artificial sequence
<220> FEATURE:
<223> OTHER INFORMATION: locus probe

<400> SEQUENCE: 251
gacgacgagt caactctgga agagcgacgt agatcggaag agcgtcgtgt agggaaagag      60
t                                                                     61

<210> SEQ ID NO 252
<211> LENGTH: 61
<212> TYPE: DNA
<213> ORGANISM: artificial sequence
<220> FEATURE:
<223> OTHER INFORMATION: locus probe

<400> SEQUENCE: 252
```

-continued

```
aggctgacca ggtagtaggt ctagctctct agatcggaag agcgtcgtgt agggaaagag      60
t                                                                     61

<210> SEQ ID NO 253
<211> LENGTH: 62
<212> TYPE: DNA
<213> ORGANISM: artificial sequence
<220> FEATURE:
<223> OTHER INFORMATION: locus probe

<400> SEQUENCE: 253
gggatttcct aacactatcg ctgagtgtga tagatcggaa gagcgtcgtg tagggaaaga      60
gt                                                                    62

<210> SEQ ID NO 254
<211> LENGTH: 62
<212> TYPE: DNA
<213> ORGANISM: artificial sequence
<220> FEATURE:
<223> OTHER INFORMATION: locus probe

<400> SEQUENCE: 254
agaaattaca gcaaggccct ccgactcaca tagatcggaa gagcgtcgtg tagggaaaga      60
gt                                                                    62

<210> SEQ ID NO 255
<211> LENGTH: 63
<212> TYPE: DNA
<213> ORGANISM: artificial sequence
<220> FEATURE:
<223> OTHER INFORMATION: locus probe

<400> SEQUENCE: 255
cttctctgga aatggttagc gaacgtgtca tgagatcgga agagcgtcgt gtagggaaag      60
agt                                                                   63

<210> SEQ ID NO 256
<211> LENGTH: 61
<212> TYPE: DNA
<213> ORGANISM: artificial sequence
<220> FEATURE:
<223> OTHER INFORMATION: locus probe

<400> SEQUENCE: 256
caacagccat ccggcaaagg tgtctcgtcg agatcggaag agcgtcgtgt agggaaagag      60
t                                                                     61

<210> SEQ ID NO 257
<211> LENGTH: 62
<212> TYPE: DNA
<213> ORGANISM: artificial sequence
<220> FEATURE:
<223> OTHER INFORMATION: locus probe

<400> SEQUENCE: 257
agccatatac agtctcttct ggctagagcg tagatcggaa gagcgtcgtg tagggaaaga      60
gt                                                                    62

<210> SEQ ID NO 258
<211> LENGTH: 60
<212> TYPE: DNA
```

<213> ORGANISM: artificial sequence
<220> FEATURE:
<223> OTHER INFORMATION: locus probe

<400> SEQUENCE: 258
caccacacgc tagctgcctc tctcacataa gatcggaaga gcgtcgtgta gggaaagagt      60

<210> SEQ ID NO 259
<211> LENGTH: 63
<212> TYPE: DNA
<213> ORGANISM: artificial sequence
<220> FEATURE:
<223> OTHER INFORMATION: locus probe

<400> SEQUENCE: 259
tctggaagat actcgagaca ttgatagcgt gcagatcgga agagcgtcgt gtagggaaag      60
agt                                                                    63

<210> SEQ ID NO 260
<211> LENGTH: 62
<212> TYPE: DNA
<213> ORGANISM: artificial sequence
<220> FEATURE:
<223> OTHER INFORMATION: locus probe

<400> SEQUENCE: 260
gctatctcta atgggcagag tgcagtactc gagatcggaa gagcgtcgtg tagggaaaga      60
gt                                                                     62

<210> SEQ ID NO 261
<211> LENGTH: 64
<212> TYPE: DNA
<213> ORGANISM: artificial sequence
<220> FEATURE:
<223> OTHER INFORMATION: locus probe

<400> SEQUENCE: 261
cccaaacaaa aagtgaaaaa gactgcgtat gatagatcgg aagagcgtcg tgtagggaaa      60
gagt                                                                   64

<210> SEQ ID NO 262
<211> LENGTH: 63
<212> TYPE: DNA
<213> ORGANISM: artificial sequence
<220> FEATURE:
<223> OTHER INFORMATION: locus probe

<400> SEQUENCE: 262
tgtcaaagca agcacagatt catgactcta taagatcgga agagcgtcgt gtagggaaag      60
agt                                                                    63

<210> SEQ ID NO 263
<211> LENGTH: 60
<212> TYPE: DNA
<213> ORGANISM: artificial sequence
<220> FEATURE:
<223> OTHER INFORMATION: locus probe

<400> SEQUENCE: 263
acctcttcgg gtgctgcagc acacgctcta gatcggaaga gcgtcgtgta gggaaagagt      60

<210> SEQ ID NO 264
<211> LENGTH: 64

```
<212> TYPE: DNA
<213> ORGANISM: artificial sequence
<220> FEATURE:
<223> OTHER INFORMATION: locus probe

<400> SEQUENCE: 264
gatgagggat aattatgaga aacggtcaga cgcagatcgg aagagcgtcg tgtagggaaa      60
gagt                                                                   64

<210> SEQ ID NO 265
<211> LENGTH: 65
<212> TYPE: DNA
<213> ORGANISM: artificial sequence
<220> FEATURE:
<223> OTHER INFORMATION: locus probe

<400> SEQUENCE: 265
aaggagtttg attatcttga tgaaagtgag cgctagatcg gaagagcgtc gtgtagggaa      60
agagt                                                                  65

<210> SEQ ID NO 266
<211> LENGTH: 63
<212> TYPE: DNA
<213> ORGANISM: artificial sequence
<220> FEATURE:
<223> OTHER INFORMATION: locus probe

<400> SEQUENCE: 266
atgaccttgg aagttgtaac gctgatacga cgagatcgga agagcgtcgt gtagggaaag      60
agt                                                                    63

<210> SEQ ID NO 267
<211> LENGTH: 65
<212> TYPE: DNA
<213> ORGANISM: artificial sequence
<220> FEATURE:
<223> OTHER INFORMATION: locus probe

<400> SEQUENCE: 267
catttatcgc agggaataat agttttcgta cgctagatcg gaagagcgtc gtgtagggaa      60
agagt                                                                  65

<210> SEQ ID NO 268
<211> LENGTH: 64
<212> TYPE: DNA
<213> ORGANISM: artificial sequence
<220> FEATURE:
<223> OTHER INFORMATION: locus probe

<400> SEQUENCE: 268
agttcagtga ttttgtattg atcccgacta gcaagatcgg aagagcgtcg tgtagggaaa      60
gagt                                                                   64

<210> SEQ ID NO 269
<211> LENGTH: 60
<212> TYPE: DNA
<213> ORGANISM: artificial sequence
<220> FEATURE:
<223> OTHER INFORMATION: locus probe

<400> SEQUENCE: 269
accatggcga ctgcggagaa ctatacgcaa gatcggaaga gcgtcgtgta gggaaagagt      60
```

-continued

<210> SEQ ID NO 270
<211> LENGTH: 62
<212> TYPE: DNA
<213> ORGANISM: artificial sequence
<220> FEATURE:
<223> OTHER INFORMATION: locus probe

<400> SEQUENCE: 270
ctattccggt gacgtagttc tgaactcaga gagatcggaa gagcgtcgtg tagggaaaga      60
gt                                                                     62

<210> SEQ ID NO 271
<211> LENGTH: 64
<212> TYPE: DNA
<213> ORGANISM: artificial sequence
<220> FEATURE:
<223> OTHER INFORMATION: locus probe

<400> SEQUENCE: 271
ggaaagaaat cacatgtatt gccagctgta tctagatcgg aagagcgtcg tgtagggaaa      60
gagt                                                                   64

<210> SEQ ID NO 272
<211> LENGTH: 63
<212> TYPE: DNA
<213> ORGANISM: artificial sequence
<220> FEATURE:
<223> OTHER INFORMATION: locus probe

<400> SEQUENCE: 272
gattctactt cctttgacca tccaatgtgt cgagatcgga agagcgtcgt gtagggaaag      60
agt                                                                    63

<210> SEQ ID NO 273
<211> LENGTH: 64
<212> TYPE: DNA
<213> ORGANISM: artificial sequence
<220> FEATURE:
<223> OTHER INFORMATION: locus probe

<400> SEQUENCE: 273
ccttttgcta attcagcagc aatacgtcgt catagatcgg aagagcgtcg tgtagggaaa      60
gagt                                                                   64

<210> SEQ ID NO 274
<211> LENGTH: 62
<212> TYPE: DNA
<213> ORGANISM: artificial sequence
<220> FEATURE:
<223> OTHER INFORMATION: locus probe

<400> SEQUENCE: 274
tcaagctctg catatgtagg ctcgctgcga tagatcggaa gagcgtcgtg tagggaaaga      60
gt                                                                     62

<210> SEQ ID NO 275
<211> LENGTH: 61
<212> TYPE: DNA
<213> ORGANISM: artificial sequence
<220> FEATURE:
<223> OTHER INFORMATION: locus probe

<400> SEQUENCE: 275

-continued

```
gaggaggaaa tagaggaagg cgtcgacgta agatcggaag agcgtcgtgt agggaaagag      60
t                                                                       61

<210> SEQ ID NO 276
<211> LENGTH: 63
<212> TYPE: DNA
<213> ORGANISM: artificial sequence
<220> FEATURE:
<223> OTHER INFORMATION: locus probe

<400> SEQUENCE: 276
ctgagaaatg cactacatca gcatcagctg ctagatcgga agagcgtcgt gtagggaaag      60
agt                                                                     63

<210> SEQ ID NO 277
<211> LENGTH: 63
<212> TYPE: DNA
<213> ORGANISM: artificial sequence
<220> FEATURE:
<223> OTHER INFORMATION: locus probe

<400> SEQUENCE: 277
gttgttaggt tgaccaacca gaactgtagt atagatcgga agagcgtcgt gtagggaaag      60
agt                                                                     63

<210> SEQ ID NO 278
<211> LENGTH: 64
<212> TYPE: DNA
<213> ORGANISM: artificial sequence
<220> FEATURE:
<223> OTHER INFORMATION: locus probe

<400> SEQUENCE: 278
agtgagagat gcagagctta ataaggatat atgagatcgg aagagcgtcg tgtagggaaa      60
gagt                                                                    64

<210> SEQ ID NO 279
<211> LENGTH: 63
<212> TYPE: DNA
<213> ORGANISM: artificial sequence
<220> FEATURE:
<223> OTHER INFORMATION: locus probe

<400> SEQUENCE: 279
gagaagccca tgtcttgctt tatatagtca gaagatcgga agagcgtcgt gtagggaaag      60
agt                                                                     63

<210> SEQ ID NO 280
<211> LENGTH: 61
<212> TYPE: DNA
<213> ORGANISM: artificial sequence
<220> FEATURE:
<223> OTHER INFORMATION: locus probe

<400> SEQUENCE: 280
tcacgcagca ggtcgtatga cttagacaca agatcggaag agcgtcgtgt agggaaagag      60
t                                                                       61

<210> SEQ ID NO 281
<211> LENGTH: 62
<212> TYPE: DNA
```

-continued

```
<213> ORGANISM: artificial sequence
<220> FEATURE:
<223> OTHER INFORMATION: locus probe

<400> SEQUENCE: 281
gaagctacta agtcgtcagc caacactatg aagatcggaa gagcgtcgtg tagggaaaga      60
gt                                                                     62

<210> SEQ ID NO 282
<211> LENGTH: 65
<212> TYPE: DNA
<213> ORGANISM: artificial sequence
<220> FEATURE:
<223> OTHER INFORMATION: locus probe

<400> SEQUENCE: 282
caacctatca atgtttaaca agtaacgtcg agatagatcg gaagagcgtc gtgtagggaa      60
agagt                                                                  65

<210> SEQ ID NO 283
<211> LENGTH: 65
<212> TYPE: DNA
<213> ORGANISM: artificial sequence
<220> FEATURE:
<223> OTHER INFORMATION: locus probe

<400> SEQUENCE: 283
gatgcgattt gcaaaaaatt agattgcgtg acgtagatcg gaagagcgtc gtgtagggaa      60
agagt                                                                  65

<210> SEQ ID NO 284
<211> LENGTH: 62
<212> TYPE: DNA
<213> ORGANISM: artificial sequence
<220> FEATURE:
<223> OTHER INFORMATION: locus probe

<400> SEQUENCE: 284
aagtgcagct ctcaaagagt cagtgcgagt cagatcggaa gagcgtcgtg tagggaaaga      60
gt                                                                     62

<210> SEQ ID NO 285
<211> LENGTH: 62
<212> TYPE: DNA
<213> ORGANISM: artificial sequence
<220> FEATURE:
<223> OTHER INFORMATION: locus probe

<400> SEQUENCE: 285
tgatgtgtta ccagctggga agtctgtgag cagatcggaa gagcgtcgtg tagggaaaga      60
gt                                                                     62

<210> SEQ ID NO 286
<211> LENGTH: 64
<212> TYPE: DNA
<213> ORGANISM: artificial sequence
<220> FEATURE:
<223> OTHER INFORMATION: locus probe

<400> SEQUENCE: 286
aaattgtttc ctgtgaagca agtgccacat cgcagatcgg aagagcgtcg tgtagggaaa      60
gagt                                                                   64
```

-continued

```
<210> SEQ ID NO 287
<211> LENGTH: 63
<212> TYPE: DNA
<213> ORGANISM: artificial sequence
<220> FEATURE:
<223> OTHER INFORMATION: locus probe

<400> SEQUENCE: 287
aaggagtaca ggtaacagcg aatctgcgcg cgagatcgga agagcgtcgt gtagggaaag        60
agt                                                                     63

<210> SEQ ID NO 288
<211> LENGTH: 64
<212> TYPE: DNA
<213> ORGANISM: artificial sequence
<220> FEATURE:
<223> OTHER INFORMATION: locus probe

<400> SEQUENCE: 288
aatatatacc ggaatgtcac ccttctacat agcagatcgg aagagcgtcg tgtagggaaa        60
gagt                                                                    64

<210> SEQ ID NO 289
<211> LENGTH: 61
<212> TYPE: DNA
<213> ORGANISM: artificial sequence
<220> FEATURE:
<223> OTHER INFORMATION: locus probe

<400> SEQUENCE: 289
tcaccttctc tgccatgctg cttgatcgac agatcggaag agcgtcgtgt agggaaagag        60
t                                                                       61

<210> SEQ ID NO 290
<211> LENGTH: 63
<212> TYPE: DNA
<213> ORGANISM: artificial sequence
<220> FEATURE:
<223> OTHER INFORMATION: locus probe

<400> SEQUENCE: 290
gcttacgtat caatgtgcag atagtgagct caagatcgga agagcgtcgt gtagggaaag        60
agt                                                                     63

<210> SEQ ID NO 291
<211> LENGTH: 64
<212> TYPE: DNA
<213> ORGANISM: artificial sequence
<220> FEATURE:
<223> OTHER INFORMATION: locus probe

<400> SEQUENCE: 291
aaagagaaca atcatcgtca tgttcgatag tgaagatcgg aagagcgtcg tgtagggaaa        60
gagt                                                                    64

<210> SEQ ID NO 292
<211> LENGTH: 62
<212> TYPE: DNA
<213> ORGANISM: artificial sequence
<220> FEATURE:
<223> OTHER INFORMATION: locus probe
```

<400> SEQUENCE: 292
ctgttctgtc gtaacttccg gtgtagacga tagatcggaa gagcgtcgtg tagggaaaga        60
gt                                                                       62

<210> SEQ ID NO 293
<211> LENGTH: 61
<212> TYPE: DNA
<213> ORGANISM: artificial sequence
<220> FEATURE:
<223> OTHER INFORMATION: locus probe

<400> SEQUENCE: 293
ggaaagtgcc ggccattgtt ggtatcgtga agatcggaag agcgtcgtgt agggaaagag        60
t                                                                        61

<210> SEQ ID NO 294
<211> LENGTH: 63
<212> TYPE: DNA
<213> ORGANISM: artificial sequence
<220> FEATURE:
<223> OTHER INFORMATION: locus probe

<400> SEQUENCE: 294
tgcagaatga agtgctgttg caaactcacg tcagatcgga agagcgtcgt gtagggaaag        60
agt                                                                      63

<210> SEQ ID NO 295
<211> LENGTH: 62
<212> TYPE: DNA
<213> ORGANISM: artificial sequence
<220> FEATURE:
<223> OTHER INFORMATION: locus probe

<400> SEQUENCE: 295
gttacttact tccaggggtc gtctacgtat cagatcggaa gagcgtcgtg tagggaaaga        60
gt                                                                       62

<210> SEQ ID NO 296
<211> LENGTH: 64
<212> TYPE: DNA
<213> ORGANISM: artificial sequence
<220> FEATURE:
<223> OTHER INFORMATION: locus probe

<400> SEQUENCE: 296
gtaatgttat gctgcctgct ttaaagcgta gtaagatcgg aagagcgtcg tgtagggaaa        60
gagt                                                                     64

<210> SEQ ID NO 297
<211> LENGTH: 63
<212> TYPE: DNA
<213> ORGANISM: artificial sequence
<220> FEATURE:
<223> OTHER INFORMATION: locus probe

<400> SEQUENCE: 297
gaggaaatag attgtctgtc cagcgagcga gcagatcgga agagcgtcgt gtagggaaag        60
agt                                                                      63

<210> SEQ ID NO 298
<211> LENGTH: 63

-continued

```
<212> TYPE: DNA
<213> ORGANISM: artificial sequence
<220> FEATURE:
<223> OTHER INFORMATION: locus probe

<400> SEQUENCE: 298
atggataaaa ctgcagcatc tgcatcatct caagatcgga agagcgtcgt gtagggaaag      60
agt                                                                     63

<210> SEQ ID NO 299
<211> LENGTH: 63
<212> TYPE: DNA
<213> ORGANISM: artificial sequence
<220> FEATURE:
<223> OTHER INFORMATION: locus probe

<400> SEQUENCE: 299
ggttgaccaa gttgcaattc actcgcatca tgagatcgga agagcgtcgt gtagggaaag      60
agt                                                                     63

<210> SEQ ID NO 300
<211> LENGTH: 63
<212> TYPE: DNA
<213> ORGANISM: artificial sequence
<220> FEATURE:
<223> OTHER INFORMATION: locus probe

<400> SEQUENCE: 300
gagaatctga ctcaaccatg atacatcgtg atagatcgga agagcgtcgt gtagggaaag      60
agt                                                                     63

<210> SEQ ID NO 301
<211> LENGTH: 65
<212> TYPE: DNA
<213> ORGANISM: artificial sequence
<220> FEATURE:
<223> OTHER INFORMATION: locus probe

<400> SEQUENCE: 301
atctttgtca aaatacgaaa atgctgatac gagcagatcg gaagagcgtc gtgtagggaa      60
agagt                                                                   65

<210> SEQ ID NO 302
<211> LENGTH: 61
<212> TYPE: DNA
<213> ORGANISM: artificial sequence
<220> FEATURE:
<223> OTHER INFORMATION: locus probe

<400> SEQUENCE: 302
gacaagctca gtatcgtcca cggctgcgta agatcggaag agcgtcgtgt agggaaagag      60
t                                                                       61

<210> SEQ ID NO 303
<211> LENGTH: 63
<212> TYPE: DNA
<213> ORGANISM: artificial sequence
<220> FEATURE:
<223> OTHER INFORMATION: locus probe

<400> SEQUENCE: 303
taacctgcat ccttgctagt tttgagtgag agagatcgga agagcgtcgt gtagggaaag      60
```

-continued agt                                                                  63

<210> SEQ ID NO 304
<211> LENGTH: 64
<212> TYPE: DNA
<213> ORGANISM: artificial sequence
<220> FEATURE:
<223> OTHER INFORMATION: locus probe

<400> SEQUENCE: 304
agaaaaataa cccccgaaaa tctgtacact atcagatcgg aagagcgtcg tgtagggaaa      60
gagt                                                                 64

<210> SEQ ID NO 305
<211> LENGTH: 62
<212> TYPE: DNA
<213> ORGANISM: artificial sequence
<220> FEATURE:
<223> OTHER INFORMATION: locus probe

<400> SEQUENCE: 305
tatgctaacc cattctccgg tctcacgtac gagatcggaa gagcgtcgtg tagggaaaga      60
gt                                                                   62

<210> SEQ ID NO 306
<211> LENGTH: 62
<212> TYPE: DNA
<213> ORGANISM: artificial sequence
<220> FEATURE:
<223> OTHER INFORMATION: locus probe

<400> SEQUENCE: 306
tgcgagaggt gaatgtgagt gaggcacact aagatcggaa gagcgtcgtg tagggaaaga      60
gt                                                                   62

<210> SEQ ID NO 307
<211> LENGTH: 62
<212> TYPE: DNA
<213> ORGANISM: artificial sequence
<220> FEATURE:
<223> OTHER INFORMATION: locus probe

<400> SEQUENCE: 307
ggcacaaatg cagacactgt taggagatcg cagatcggaa gagcgtcgtg tagggaaaga      60
gt                                                                   62

<210> SEQ ID NO 308
<211> LENGTH: 61
<212> TYPE: DNA
<213> ORGANISM: artificial sequence
<220> FEATURE:
<223> OTHER INFORMATION: locus probe

<400> SEQUENCE: 308
ctgaagctgc acgacatgtc gctactatat agatcggaag agcgtcgtgt agggaaagag      60
t                                                                    61

<210> SEQ ID NO 309
<211> LENGTH: 64
<212> TYPE: DNA
<213> ORGANISM: artificial sequence
<220> FEATURE:
<223> OTHER INFORMATION: locus probe -continued

```
<400> SEQUENCE: 309
gagaaggtaa gaccacctta aaattgtcac acaagatcgg aagagcgtcg tgtagggaaa      60
gagt                                                                    64

<210> SEQ ID NO 310
<211> LENGTH: 63
<212> TYPE: DNA
<213> ORGANISM: artificial sequence
<220> FEATURE:
<223> OTHER INFORMATION: locus probe

<400> SEQUENCE: 310
ttcgctaggt taagacatgg agacgctcgt gaagatcgga agagcgtcgt gtagggaaag      60
agt                                                                     63

<210> SEQ ID NO 311
<211> LENGTH: 61
<212> TYPE: DNA
<213> ORGANISM: artificial sequence
<220> FEATURE:
<223> OTHER INFORMATION: locus probe

<400> SEQUENCE: 311
aggttgtggt cacttgctcg tctctagatg agatcggaag agcgtcgtgt agggaaagag      60
t                                                                       61

<210> SEQ ID NO 312
<211> LENGTH: 66
<212> TYPE: DNA
<213> ORGANISM: artificial sequence
<220> FEATURE:
<223> OTHER INFORMATION: locus probe

<400> SEQUENCE: 312
atgttaattt ctagagtttt tcctgttaga tgacgagatc ggaagagcgt cgtgtaggga      60
aagagt                                                                  66

<210> SEQ ID NO 313
<211> LENGTH: 63
<212> TYPE: DNA
<213> ORGANISM: artificial sequence
<220> FEATURE:
<223> OTHER INFORMATION: locus probe

<400> SEQUENCE: 313
gagtttggta tgcagtggtt gttggtacag tgagatcgga agagcgtcgt gtagggaaag      60
agt                                                                     63

<210> SEQ ID NO 314
<211> LENGTH: 61
<212> TYPE: DNA
<213> ORGANISM: artificial sequence
<220> FEATURE:
<223> OTHER INFORMATION: locus probe

<400> SEQUENCE: 314
gcaatcgaag ctctgcagtg gctctatcag agatcggaag agcgtcgtgt agggaaagag      60
t                                                                       61

<210> SEQ ID NO 315
```

-continued

```
<211> LENGTH: 62
<212> TYPE: DNA
<213> ORGANISM: artificial sequence
<220> FEATURE:
<223> OTHER INFORMATION: locus probe

<400> SEQUENCE: 315
cctgcatatg catatgccat gggtgtgacg cagatcggaa gagcgtcgtg tagggaaaga        60
gt                                                                       62

<210> SEQ ID NO 316
<211> LENGTH: 64
<212> TYPE: DNA
<213> ORGANISM: artificial sequence
<220> FEATURE:
<223> OTHER INFORMATION: locus probe

<400> SEQUENCE: 316
taaatgttct gcaaaaggtc cgtttactgt atcagatcgg aagagcgtcg tgtagggaaa        60
gagt                                                                     64

<210> SEQ ID NO 317
<211> LENGTH: 62
<212> TYPE: DNA
<213> ORGANISM: artificial sequence
<220> FEATURE:
<223> OTHER INFORMATION: locus probe

<400> SEQUENCE: 317
gagcttgaca tgctaacacc ttcatcatat aagatcggaa gagcgtcgtg tagggaaaga        60
gt                                                                       62

<210> SEQ ID NO 318
<211> LENGTH: 61
<212> TYPE: DNA
<213> ORGANISM: artificial sequence
<220> FEATURE:
<223> OTHER INFORMATION: locus probe

<400> SEQUENCE: 318
aagccaggga ctcggatgaa ctgctatgat agatcggaag agcgtcgtgt agggaaagag        60
t                                                                        61

<210> SEQ ID NO 319
<211> LENGTH: 64
<212> TYPE: DNA
<213> ORGANISM: artificial sequence
<220> FEATURE:
<223> OTHER INFORMATION: locus probe

<400> SEQUENCE: 319
tttgtcaact tgtcaacatc agagctcgag tcgagatcgg aagagcgtcg tgtagggaaa        60
gagt                                                                     64

<210> SEQ ID NO 320
<211> LENGTH: 61
<212> TYPE: DNA
<213> ORGANISM: artificial sequence
<220> FEATURE:
<223> OTHER INFORMATION: locus probe

<400> SEQUENCE: 320
gtatccgtgt cgcttgtaga gctatatcga agatcggaag agcgtcgtgt agggaaagag        60
``` t                                                                                                61

<210> SEQ ID NO 321
<211> LENGTH: 64
<212> TYPE: DNA
<213> ORGANISM: artificial sequence
<220> FEATURE:
<223> OTHER INFORMATION: locus probe

<400> SEQUENCE: 321
gatcacatca acgaacttgt aaaccgctcg cgcagatcgg aagagcgtcg tgtagggaaa      60
gagt                                                                                             64

<210> SEQ ID NO 322
<211> LENGTH: 61
<212> TYPE: DNA
<213> ORGANISM: artificial sequence
<220> FEATURE:
<223> OTHER INFORMATION: locus probe

<400> SEQUENCE: 322
gaagcatggg cctctctcga tccgtgctgt agatcggaag agcgtcgtgt agggaaagag      60
t                                                                                                61

<210> SEQ ID NO 323
<211> LENGTH: 62
<212> TYPE: DNA
<213> ORGANISM: artificial sequence
<220> FEATURE:
<223> OTHER INFORMATION: locus probe

<400> SEQUENCE: 323
taacatctcg tcggcataga ggcgcacgct gagatcggaa gagcgtcgtg tagggaaaga      60
gt                                                                                               62

<210> SEQ ID NO 324
<211> LENGTH: 65
<212> TYPE: DNA
<213> ORGANISM: artificial sequence
<220> FEATURE:
<223> OTHER INFORMATION: locus probe

<400> SEQUENCE: 324
taatatgcag ctaacatctc atatcctcag atagagatcg gaagagcgtc gtgtagggaa      60
agagt                                                                                            65

<210> SEQ ID NO 325
<211> LENGTH: 62
<212> TYPE: DNA
<213> ORGANISM: artificial sequence
<220> FEATURE:
<223> OTHER INFORMATION: locus probe

<400> SEQUENCE: 325
ccggcaatta ggtggatgtc ataactcgct cagatcggaa gagcgtcgtg taggaaaga       60 gt                                                                                               62

<210> SEQ ID NO 326
<211> LENGTH: 62
<212> TYPE: DNA
<213> ORGANISM: artificial sequence
<220> FEATURE:

<223> OTHER INFORMATION: locus probe

<400> SEQUENCE: 326
acaacgttag tttctcgagc aggtgagtag aagatcggaa gagcgtcgtg tagggaaaga    60
gt                                                                    62

<210> SEQ ID NO 327
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 327
tggagttcag acgtgtgctc ttccgatctn nnnnncacaa tttcagtcgt ttcttctttg    60
gagt                                                                  64

<210> SEQ ID NO 328
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 328
tggagttcag acgtgtgctc ttccgatctn nnnnnctatt caaccgggtc tgagacaagt    60
tt                                                                    62

<210> SEQ ID NO 329
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 329
tggagttcag acgtgtgctc ttccgatctn nnnnnagcta cattcagcag cattcttttt    60
gtct                                                                  64

<210> SEQ ID NO 330
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 330
tggagttcag acgtgtgctc ttccgatctn nnnnngacgg ctcaaaacca agagatcgac    60
ct                                                                    62

```
<210> SEQ ID NO 331
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 331
tggagttcag acgtgtgctc ttccgatctn nnnncgtgc acatggcaga ggcagaccac      60
a                                                                     61

<210> SEQ ID NO 332
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 332
tggagttcag acgtgtgctc ttccgatctn nnnnacact cctaaagacc gataccaact      60
tttt                                                                  64

<210> SEQ ID NO 333
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 333
tggagttcag acgtgtgctc ttccgatctn nnnngagtg aggtggaaga ggaagcccaa      60
a                                                                     61

<210> SEQ ID NO 334
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 334
tggagttcag acgtgtgctc ttccgatctn nnnntactg cttgagtagg agcgtcacat      60
tt                                                                    62

<210> SEQ ID NO 335
<211> LENGTH: 65
<212> TYPE: DNA
<213> ORGANISM: artificial sequence
<220> FEATURE:
```

-continued

<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 335
tggagttcag acgtgtgctc ttccgatctn nnnnncgtga attcatgcaa tcaagcactt      60
tagat                                                                  65

<210> SEQ ID NO 336
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 336
tggagttcag acgtgtgctc ttccgatctn nnnnngagtt gaagaaaaat cctgagaacg      60
cct                                                                    63

<210> SEQ ID NO 337
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 337
tggagttcag acgtgtgctc ttccgatctn nnnnnctatc acttattatc gttggaccac      60
gac                                                                    63

<210> SEQ ID NO 338
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 338
tggagttcag acgtgtgctc ttccgatctn nnnnnatgca cctggatcaa aaagggtctt      60
caa                                                                    63

<210> SEQ ID NO 339
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 339

-continued

```
tggagttcag acgtgtgctc ttccgatctn nnnnnctcgg tgaattgttg caggtaaaaa       60
attgt                                                                    65

<210> SEQ ID NO 340
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 340
tggagttcag acgtgtgctc ttccgatctn nnnnctcga aactgcaatg aaaaatggat        60
tggtt                                                                    65

<210> SEQ ID NO 341
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 341
tggagttcag acgtgtgctc ttccgatctn nnnntactg gcgaactagt ccacaaattc        60
att                                                                      63

<210> SEQ ID NO 342
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 342
tggagttcag acgtgtgctc ttccgatctn nnnngagtg acgtgacgtg aacaaaccaa        60
ga                                                                       62

<210> SEQ ID NO 343
<211> LENGTH: 60
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 343
tggagttcag acgtgtgctc ttccgatctn nnnnagctc gtgtggcgtc ccctgattt         60

<210> SEQ ID NO 344
<211> LENGTH: 60
<212> TYPE: DNA
```

<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 344
tggagttcag acgtgtgctc ttccgatctn nnnnngagtt tccgggcagc taggagggtt        60

<210> SEQ ID NO 345
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 345
tggagttcag acgtgtgctc ttccgatctn nnnnnagtct acttgattga tctaataaag        60
cagca                                                                    65

<210> SEQ ID NO 346
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 346
tggagttcag acgtgtgctc ttccgatctn nnnncgtgg caccgtacca atatctctgg         60
at                                                                       62

<210> SEQ ID NO 347
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 347
tggagttcag acgtgtgctc ttccgatctn nnnncgtgg tgtgtggtac aaacaaatga         60
acata                                                                    65

<210> SEQ ID NO 348
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 348

-continued

```
tggagttcag acgtgtgctc ttccgatctn nnnnnatgca ctgctgcggc tgagtgttga    60
a                                                                    61

<210> SEQ ID NO 349
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 349
tggagttcag acgtgtgctc ttccgatctn nnnncgtgc atagctatgc tatggttcgc     60
ata                                                                  63

<210> SEQ ID NO 350
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 350
tggagttcag acgtgtgctc ttccgatctn nnnnnatcag ctatcatcat cagagaaacc    60
attt                                                                 64

<210> SEQ ID NO 351
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 351
tggagttcag acgtgtgctc ttccgatctn nnnnnatgcc tgcatggctg catcgctttc    60
aa                                                                   62

<210> SEQ ID NO 352
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 352
tggagttcag acgtgtgctc ttccgatctn nnnnngcata ccttgcactt ttaatcttaa    60
ctaca                                                                65

<210> SEQ ID NO 353
```

```
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 353
tggagttcag acgtgtgctc ttccgatctn nnnnnactac tggtttggca gacgatcaca      60
ca                                                                     62

<210> SEQ ID NO 354
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 354
tggagttcag acgtgtgctc ttccgatctn nnnnnctata ctgtactcac acacagggca      60
at                                                                     62

<210> SEQ ID NO 355
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 355
tggagttcag acgtgtgctc ttccgatctn nnnnnagctg agatttctga aaacctaagc      60
ccat                                                                   64

<210> SEQ ID NO 356
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 356
tggagttcag acgtgtgctc ttccgatctn nnnnncgtga ccaaggataa tcttgttcca      60
tctt                                                                   64

<210> SEQ ID NO 357
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
```

```
<222> LOCATION: (30)..(35)
<223> OTHER INFORMATION: n is a, c, g, or t

<400> SEQUENCE: 357
tggagttcag acgtgtgctc ttccgatctn nnnnnatgcc agatgaaact tagtatggtg    60
tagt                                                                 64

<210> SEQ ID NO 358
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 358
tggagttcag acgtgtgctc ttccgatctn nnnntactc ggcaagtaca gtcatctctc    60
tt                                                                   62

<210> SEQ ID NO 359
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 359
tggagttcag acgtgtgctc ttccgatctn nnnnnatgct gcaacttgga gcatctctac    60
att                                                                  63

<210> SEQ ID NO 360
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 360
tggagttcag acgtgtgctc ttccgatctn nnnngcatg tagcagcaac cactttatct    60
gata                                                                 64

<210> SEQ ID NO 361
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 361
tggagttcag acgtgtgctc ttccgatctn nnnnactac acatccggcc caaacttctg    60
```

-continued

```
aa                                                                                       62

<210> SEQ ID NO 362
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 362
tggagttcag acgtgtgctc ttccgatctn nnnnncgtgg aagtctagct aactgtggat      60
ttc                                                                                      63

<210> SEQ ID NO 363
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 363
tggagttcag acgtgtgctc ttccgatctn nnnnngacgt acaagcgtca accaaagagc      60
ct                                                                                       62

<210> SEQ ID NO 364
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 364
tggagttcag acgtgtgctc ttccgatctn nnnnngagtc tacgcgtacc aggaaagata      60
gt                                                                                       62

<210> SEQ ID NO 365
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 365
tggagttcag acgtgtgctc ttccgatctn nnnnnactaa atctcagtcg ccagtttctc      60
ttt                                                                                      63

<210> SEQ ID NO 366
<211> LENGTH: 64
<212> TYPE: DNA
<213> ORGANISM: artificial sequence
```

-continued

<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 366
tggagttcag acgtgtgctc ttccgatctn nnnnnatgct cagttggcat aataacattg      60
acct                                                                  64

<210> SEQ ID NO 367
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 367
tggagttcag acgtgtgctc ttccgatctn nnnnntactg gctaatatgt ctgctattga      60
ccta                                                                  64

<210> SEQ ID NO 368
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 368
tggagttcag acgtgtgctc ttccgatctn nnnnnctgac cacgtcaacg gtgcgtagtg      60
t                                                                     61

<210> SEQ ID NO 369
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 369
tggagttcag acgtgtgctc ttccgatctn nnnnnactat ctcagggatc atgtgtgctc      60
at                                                                    62

<210> SEQ ID NO 370
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t -continued

```
<400> SEQUENCE: 370
tggagttcag acgtgtgctc ttccgatctn nnnngacgc tagcaaccac acagacacag       60
ga                                                                     62

<210> SEQ ID NO 371
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 371
tggagttcag acgtgtgctc ttccgatctn nnnncacaa tcagaaaaaa ctatgacagt       60
ctcta                                                                  65

<210> SEQ ID NO 372
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 372
tggagttcag acgtgtgctc ttccgatctn nnnnctatt atctgttgtg aaaaagaaac       60
ccaat                                                                  65

<210> SEQ ID NO 373
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 373
tggagttcag acgtgtgctc ttccgatctn nnnnctgag tagcccattg tgcctcttgt       60
ta                                                                     62

<210> SEQ ID NO 374
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 374
tggagttcag acgtgtgctc ttccgatctn nnnnatgca tcatccccac tccaactacc       60
aa                                                                     62
```

```
<210> SEQ ID NO 375
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 375
tggagttcag acgtgtgctc ttccgatctn nnnnnctcgc tagatcctat ggccaaagaa      60
gc                                                                     62

<210> SEQ ID NO 376
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 376
tggagttcag acgtgtgctc ttccgatctn nnnnngagtg gttgttacaa cggagaagaa      60
cga                                                                    63

<210> SEQ ID NO 377
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 377
tggagttcag acgtgtgctc ttccgatctn nnnnnatcag gccgggacag tagtatcagt      60
t                                                                      61

<210> SEQ ID NO 378
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 378
tggagttcag acgtgtgctc ttccgatctn nnnnngagtc ggccatttct ttcacacaat      60
cgt                                                                    63

<210> SEQ ID NO 379
<211> LENGTH: 62
<212> TYPE: DNA
<213> ORGANISM: artificial sequence
<220> FEATURE:
<223> OTHER INFORMATION: allele 1 probe
<220> FEATURE:
```

-continued

```
<221> NAME/KEY: misc_feature
<222> LOCATION: (30)..(35)
<223> OTHER INFORMATION: n is a, c, g, or t

<400> SEQUENCE: 379
tggagttcag acgtgtgctc ttccgatctn nnnnnagtcc agttcgcacc ctgtgtaata      60
ca                                                                     62

<210> SEQ ID NO 380
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 380
tggagttcag acgtgtgctc ttccgatctn nnnncgtgg tctagctgca ctggctactg      60
t                                                                      61

<210> SEQ ID NO 381
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 381
tggagttcag acgtgtgctc ttccgatctn nnnncacag gacacgataa tcctctttgg      60
gta                                                                    63

<210> SEQ ID NO 382
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 382
tggagttcag acgtgtgctc ttccgatctn nnnncgtgg ttacatgaaa aggaagcttg      60
tttca                                                                  65

<210> SEQ ID NO 383
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 383
tggagttcag acgtgtgctc ttccgatctn nnnnctcga tggttgctgc tcaagtctac      60
```

-continued

```
gt                                                            62

<210> SEQ ID NO 384
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 384
tggagttcag acgtgtgctc ttccgatctn nnnnntactc agtgagatga cagtgatatg    60
gttt                                                          64

<210> SEQ ID NO 385
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 385
tggagttcag acgtgtgctc ttccgatctn nnnnnagctt gcttaacatg gtttctgctg    60
agt                                                           63

<210> SEQ ID NO 386
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 386
tggagttcag acgtgtgctc ttccgatctn nnnnnctcgc tcaaactaac cgttggatga    60
ggt                                                           63

<210> SEQ ID NO 387
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 387
tggagttcag acgtgtgctc ttccgatctn nnnnnctata cgttatgaag ctgttgcaag    60
gaa                                                           63

<210> SEQ ID NO 388
<211> LENGTH: 61
<212> TYPE: DNA
```

-continued

```
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 388
tggagttcag acgtgtgctc ttccgatctn nnnnnatcac agcagccatt cgttccacag      60
t                                                                     61

<210> SEQ ID NO 389
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 389
tggagttcag acgtgtgctc ttccgatctn nnnnnagctt agatggagaa attgtaaccg      60
gca                                                                   63

<210> SEQ ID NO 390
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 390
tggagttcag acgtgtgctc ttccgatctn nnnnnctgag cacacaattg atctgcagtg      60
act                                                                   63

<210> SEQ ID NO 391
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 391
tggagttcag acgtgtgctc ttccgatctn nnnnntacta agtcccacgt ggtacataat      60
tct                                                                   63

<210> SEQ ID NO 392
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t
```

-continued

```
<400> SEQUENCE: 392
tggagttcag acgtgtgctc ttccgatctn nnnnncacat ggtcgttaat cacgagatca      60
aca                                                                    63

<210> SEQ ID NO 393
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 393
tggagttcag acgtgtgctc ttccgatctn nnnnnctatc tgaaaaacct ttggaataag      60
tgctt                                                                  65

<210> SEQ ID NO 394
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 394
tggagttcag acgtgtgctc ttccgatctn nnnnnctatt ttctgacgtc tcaactgttc      60
ctt                                                                    63

<210> SEQ ID NO 395
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 395
tggagttcag acgtgtgctc ttccgatctn nnnnnacacc gacttctcta gttcctcagt      60
ca                                                                     62

<210> SEQ ID NO 396
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 396
tggagttcag acgtgtgctc ttccgatctn nnnnntactt ggaatttctt ggagaagttc      60
cct                                                                    63
```

-continued

<210> SEQ ID NO 397
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 397
tggagttcag acgtgtgctc ttccgatctn nnnnnactat ggtatttata ctgtgagctg      60
agc                                                                    63

<210> SEQ ID NO 398
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 398
tggagttcag acgtgtgctc ttccgatctn nnnnnatcaa gctcaagagg aaaatcagca      60
tct                                                                    63

<210> SEQ ID NO 399
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 399
tggagttcag acgtgtgctc ttccgatctn nnnnnctcgt agtatgtgtt tgatcgcgct      60
agt                                                                    63

<210> SEQ ID NO 400
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 400
tggagttcag acgtgtgctc ttccgatctn nnnnnacact aggtaattta taggcggctg      60
atta                                                                   64

<210> SEQ ID NO 401
<211> LENGTH: 63
<212> TYPE: DNA
<213> ORGANISM: artificial sequence
<220> FEATURE:
<223> OTHER INFORMATION: allele 1 probe -continued

```
<220> FEATURE:
<221> NAME/KEY: misc_feature
<222> LOCATION: (30)..(35)
<223> OTHER INFORMATION: n is a, c, g, or t

<400> SEQUENCE: 401
tggagttcag acgtgtgctc ttccgatctn nnnnnagctg ccggctattg cagacaaaaa    60
gat                                                                  63

<210> SEQ ID NO 402
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 402
tggagttcag acgtgtgctc ttccgatctn nnnnnagtct ttgtgggaga ggaattctgg    60
ca                                                                   62

<210> SEQ ID NO 403
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 403
tggagttcag acgtgtgctc ttccgatctn nnnnctcgc ctcgtcttct ttcacctctc     60
ca                                                                   62

<210> SEQ ID NO 404
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 404
tggagttcag acgtgtgctc ttccgatctn nnnnnagtcc agtacaacct tgcagatttt    60
ggta                                                                 64

<210> SEQ ID NO 405
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 405
```

-continued

```
tggagttcag acgtgtgctc ttccgatctn nnnnncgtgt agttgtagat ctgggggtta      60
ctt                                                                    63

<210> SEQ ID NO 406
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 406
tggagttcag acgtgtgctc ttccgatctn nnnnngacgg ctctcactag agcccctaca      60
t                                                                      61

<210> SEQ ID NO 407
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 407
tggagttcag acgtgtgctc ttccgatctn nnnnnctcgg tacggtggtt ggaacagtaa      60
ct                                                                     62

<210> SEQ ID NO 408
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 408
tggagttcag acgtgtgctc ttccgatctn nnnnngagtc gtatacacgc acatgtgtgt      60
gt                                                                     62

<210> SEQ ID NO 409
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 409
tggagttcag acgtgtgctc ttccgatctn nnnnntacta tgagctgcag tttgcttctt      60
act                                                                    63

<210> SEQ ID NO 410
<211> LENGTH: 60
```

```
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 410
tggagttcag acgtgtgctc ttccgatctn nnnnngagtg gaccaacttg tcggcgccaa      60

<210> SEQ ID NO 411
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 411
tggagttcag acgtgtgctc ttccgatctn nnnnntactg catgcggaaa ataatggagt      60
act                                                                   63

<210> SEQ ID NO 412
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 412
tggagttcag acgtgtgctc ttccgatctn nnnnnacaca aaaacacatt ctgcaagcaa      60
aacat                                                                 65

<210> SEQ ID NO 413
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 413
tggagttcag acgtgtgctc ttccgatctn nnnnnctgat ttgaggaggg tgctgcaaga      60
tt                                                                    62

<210> SEQ ID NO 414
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t
```

<400> SEQUENCE: 414
tggagttcag acgtgtgctc ttccgatctn nnnnnactag ggtgtacatt ggtttgcttg      60
ct                                                                     62

<210> SEQ ID NO 415
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 415
tggagttcag acgtgtgctc ttccgatctn nnnnnatgct atcgtgcttc tccaggtaac      60
ga                                                                     62

<210> SEQ ID NO 416
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 416
tggagttcag acgtgtgctc ttccgatctn nnnnngcata tatggccgat ctgggtagtg      60
ta                                                                     62

<210> SEQ ID NO 417
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 417
tggagttcag acgtgtgctc ttccgatctn nnnnnagctg ggtgtctggt tcttcaaaca      60
gt                                                                     62

<210> SEQ ID NO 418
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 418
tggagttcag acgtgtgctc ttccgatctn nnnnnactat gatcgagctg attagtttct      60
agat                                                                   64

-continued

```
<210> SEQ ID NO 419
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 419
tggagttcag acgtgtgctc ttccgatctn nnnnnatgcc ggcttcatgt ttctcccaaa      60
aaat                                                                   64

<210> SEQ ID NO 420
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 420
tggagttcag acgtgtgctc ttccgatctn nnnnnctcgg aagccctcta agttcatcga      60
ctt                                                                    63

<210> SEQ ID NO 421
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 421
tggagttcag acgtgtgctc ttccgatctn nnnnngagtg ttgaaatgct ttctaatggt      60
ggga                                                                   64

<210> SEQ ID NO 422
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 422
tggagttcag acgtgtgctc ttccgatctn nnnnntacta tacagcaaca tcataacaca      60
tatga                                                                  65

<210> SEQ ID NO 423
<211> LENGTH: 62
<212> TYPE: DNA
<213> ORGANISM: artificial sequence
<220> FEATURE:
<223> OTHER INFORMATION: allele 1 probe
<220> FEATURE:
```

-continued

```
<221> NAME/KEY: misc_feature
<222> LOCATION: (30)..(35)
<223> OTHER INFORMATION: n is a, c, g, or t

<400> SEQUENCE: 423
tggagttcag acgtgtgctc ttccgatctn nnnnnctcgc taatcctttg ccgtgctcag      60
ct                                                                     62

<210> SEQ ID NO 424
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 424
tggagttcag acgtgtgctc ttccgatctn nnnnntactg ttttggatcc tcaaagagaa      60
ggt                                                                    63

<210> SEQ ID NO 425
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 425
tggagttcag acgtgtgctc ttccgatctn nnnnnacacg accctgttgt tggctataca      60
gat                                                                    63

<210> SEQ ID NO 426
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 426
tggagttcag acgtgtgctc ttccgatctn nnnnncacaa ttatcccggg caagtccatg      60
at                                                                     62

<210> SEQ ID NO 427
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 427
tggagttcag acgtgtgctc ttccgatctn nnnnnctatg gcaggtgcag acaacggcaa      60
```

-continued a                                                                                                    61

<210> SEQ ID NO 428
<211> LENGTH: 60
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 428
tggagttcag acgtgtgctc ttccgatctn nnnnnatcac cgatcgggcg gttgagatca      60

<210> SEQ ID NO 429
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 429
tggagttcag acgtgtgctc ttccgatctn nnnnntactg ttcggtcacg gcggttgaat      60
tt                                                                                                   62

<210> SEQ ID NO 430
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 430
tggagttcag acgtgtgctc ttccgatctn nnnnngcatt tgcagcagca acccacggtt      60
t                                                                                                    61

<210> SEQ ID NO 431
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 431
tggagttcag acgtgtgctc ttccgatctn nnnnnactag tctagaatga atttagcaga      60
cttga                                                                                                65

<210> SEQ ID NO 432
<211> LENGTH: 66
<212> TYPE: DNA
<213> ORGANISM: artificial sequence
<220> FEATURE:

<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 432
tggagttcag acgtgtgctc ttccgatctn nnnnnacact tctttctttt tacaacagac        60
ttacat                                                                    66

<210> SEQ ID NO 433
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 433
tggagttcag acgtgtgctc ttccgatctn nnnnngacgg tcctgctggt cagcgtttct        60
aa                                                                        62

<210> SEQ ID NO 434
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 434
tggagttcag acgtgtgctc ttccgatctn nnnnncacat taatagcgat gtgtttcagt        60
tgca                                                                      64

<210> SEQ ID NO 435
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 435
tggagttcag acgtgtgctc ttccgatctn nnnnnctcgt tgcagcctcc ggtcacacaa        60
a                                                                         61

<210> SEQ ID NO 436
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 436

```
tggagttcag acgtgtgctc ttccgatctn nnnnnatcac atcgtcacag tcagtagtag      60
ct                                                                     62

<210> SEQ ID NO 437
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 437
tggagttcag acgtgtgctc ttccgatctn nnnnnagtcg acacgatgat gtggagaaag      60
gt                                                                     62

<210> SEQ ID NO 438
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 438
tggagttcag acgtgtgctc ttccgatctn nnnnnacact gcattagatt cgccacttag      60
gat                                                                    63

<210> SEQ ID NO 439
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 439
tggagttcag acgtgtgctc ttccgatctn nnnnnagctc aggagacaga gttctgcaca      60
at                                                                     62

<210> SEQ ID NO 440
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 440
tggagttcag acgtgtgctc ttccgatctn nnnnnctatc attagctgag tcaattcagt      60
ccta                                                                   64

<210> SEQ ID NO 441
```

-continued

```
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 441
tggagttcag acgtgtgctc ttccgatctn nnnnnacacg acgactaacg tgtcttgctt      60
ca                                                                     62

<210> SEQ ID NO 442
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 442
tggagttcag acgtgtgctc ttccgatctn nnnnnagctc aaaacaccag tagcatgcac      60
tat                                                                    63

<210> SEQ ID NO 443
<211> LENGTH: 60
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 443
tggagttcag acgtgtgctc ttccgatctn nnnnnctgac caaccgatcg agcgagcatc      60

<210> SEQ ID NO 444
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 444
tggagttcag acgtgtgctc ttccgatctn nnnncacat tcacaaaagc atttggcgct      60
aca                                                                    63

<210> SEQ ID NO 445
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t
```

-continued

<400> SEQUENCE: 445
tggagttcag acgtgtgctc ttccgatctn nnnnatgcc agagctgaga gcagtggacg      60
t                                                                    61

<210> SEQ ID NO 446
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 446
tggagttcag acgtgtgctc ttccgatctn nnnnnctcgc tctgaagtcc ttgtccagta      60
aaat                                                                  64

<210> SEQ ID NO 447
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 447
tggagttcag acgtgtgctc ttccgatctn nnnngacgg tgacagttgt caaacagacc      60
aat                                                                  63

<210> SEQ ID NO 448
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 448
tggagttcag acgtgtgctc ttccgatctn nnnnctgat atattaagat tgtgtgctgc      60
aagtt                                                                65

<210> SEQ ID NO 449
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 449
tggagttcag acgtgtgctc ttccgatctn nnnnactaa agcggttgca ataaaccagc      60
ca                                                                   62

-continued

```
<210> SEQ ID NO 450
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 450
tggagttcag acgtgtgctc ttccgatctn nnnnnctcgc atcggatgtg cggtcaagaa      60
ct                                                                    62

<210> SEQ ID NO 451
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 451
tggagttcag acgtgtgctc ttccgatctn nnnnngagtc catactaagc tgccactcac      60
tt                                                                    62

<210> SEQ ID NO 452
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 452
tggagttcag acgtgtgctc ttccgatctn nnnnnctgag gtgtgtcctc atcctcatcg      60
a                                                                     61

<210> SEQ ID NO 453
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 453
tggagttcag acgtgtgctc ttccgatctn nnnnnctgat ttcagacttt cagctgcgat      60
gaa                                                                   63

<210> SEQ ID NO 454
<211> LENGTH: 61
<212> TYPE: DNA
<213> ORGANISM: artificial sequence
<220> FEATURE:
<223> OTHER INFORMATION: allele 1 probe
```

```
<220> FEATURE:
<221> NAME/KEY: misc_feature
<222> LOCATION: (30)..(35)
<223> OTHER INFORMATION: n is a, c, g, or t

<400> SEQUENCE: 454
tggagttcag acgtgtgctc ttccgatctn nnnnnagtcc tcatcttccc ggtccgaacg      60
a                                                                     61

<210> SEQ ID NO 455
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 455
tggagttcag acgtgtgctc ttccgatctn nnnnnactac ctcagtacca agacgacgaa      60
ga                                                                    62

<210> SEQ ID NO 456
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 456
tggagttcag acgtgtgctc ttccgatctn nnnngcatc cgctgcaaaa ggatgggggct     60 t                                                                     61

<210> SEQ ID NO 457
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 457
tggagttcag acgtgtgctc ttccgatctn nnnngacgc aaggtggacc agaagagaaa      60
ct                                                                    62

<210> SEQ ID NO 458
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 458
```

```
tggagttcag acgtgtgctc ttccgatctn nnnnnctatg caaagccttc atttgtgcct        60
ct                                                                       62
```

<210> SEQ ID NO 459
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 459

```
tggagttcag acgtgtgctc ttccgatctn nnnnnacacc aaaaccaacg cagggtgttt        60
ca                                                                       62
```

<210> SEQ ID NO 460
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 460

```
tggagttcag acgtgtgctc ttccgatctn nnnnngcatc tggctgctct ctggcaaaaa        60
at                                                                       62
```

<210> SEQ ID NO 461
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 461

```
tggagttcag acgtgtgctc ttccgatctn nnnnnatcac agagtactac cagttgctcg        60
taa                                                                      63
```

<210> SEQ ID NO 462
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 462

```
tggagttcag acgtgtgctc ttccgatctn nnnnnctatc attgccatgt gatgctgagg        60
aaa                                                                      63
```

<210> SEQ ID NO 463
<211> LENGTH: 62

-continued

```
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 463
tggagttcag acgtgtgctc ttccgatctn nnnnnacaca atgcatctgg gactgctctg     60
at                                                                     62

<210> SEQ ID NO 464
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 464
tggagttcag acgtgtgctc ttccgatctn nnnnngacgc gcagcgaaca gaattctcga     60
ta                                                                     62

<210> SEQ ID NO 465
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 465
tggagttcag acgtgtgctc ttccgatctn nnnnctcgc tagccgagct agggatcctc     60
a                                                                      61

<210> SEQ ID NO 466
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 466
tggagttcag acgtgtgctc ttccgatctn nnnnngcatc ctacatcggc atatctacca     60
tc                                                                     62

<210> SEQ ID NO 467
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
```

-continued

<223> OTHER INFORMATION: n is a, c, g, or t

<400> SEQUENCE: 467
tggagttcag acgtgtgctc ttccgatctn nnnngagtc aacacagctg caaaacatgc      60
att                                                                    63

<210> SEQ ID NO 468
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 468
tggagttcag acgtgtgctc ttccgatctn nnnnactaa cgtttgctgc atgttttcag      60
act                                                                    63

<210> SEQ ID NO 469
<211> LENGTH: 60
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 469
tggagttcag acgtgtgctc ttccgatctn nnnncacag tcctctggga tttcggcgct      60

<210> SEQ ID NO 470
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 470
tggagttcag acgtgtgctc ttccgatctn nnnnatgcc tgaccaatgg ttagctgaca      60
tga                                                                    63

<210> SEQ ID NO 471
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 471
tggagttcag acgtgtgctc ttccgatctn nnnnagtct gcccttcgtt gtcctgaaca      60
ta                                                                     62

-continued

<210> SEQ ID NO 472
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 472
tggagttcag acgtgtgctc ttccgatctn nnnnntactg aaagaagcta ctaatgacct     60
gca                                                                    63

<210> SEQ ID NO 473
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 473
tggagttcag acgtgtgctc ttccgatctn nnnnnactag aatcagagca tcctgaatac     60
aca                                                                    63

<210> SEQ ID NO 474
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 474
tggagttcag acgtgtgctc ttccgatctn nnnnnagctg agtcattatt ctccatcgcc     60
ca                                                                     62

<210> SEQ ID NO 475
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 475
tggagttcag acgtgtgctc ttccgatctn nnnnngacgt gccctctgac ctagctagtt     60
at                                                                     62

<210> SEQ ID NO 476
<211> LENGTH: 63
<212> TYPE: DNA
<213> ORGANISM: artificial sequence
<220> FEATURE:
<223> OTHER INFORMATION: allele 1 probe
<220> FEATURE:

```
<221> NAME/KEY: misc_feature
<222> LOCATION: (30)..(35)
<223> OTHER INFORMATION: n is a, c, g, or t

<400> SEQUENCE: 476
tggagttcag acgtgtgctc ttccgatctn nnnnnacaca ctattgagca gtcatccgtc     60
tat                                                                    63

<210> SEQ ID NO 477
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 477
tggagttcag acgtgtgctc ttccgatctn nnnnnctcgt tagtgctaca gctacacaag     60
tgt                                                                    63

<210> SEQ ID NO 478
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 478
tggagttcag acgtgtgctc ttccgatctn nnnnngcatg gtatgctggc cgcaggtaca     60
a                                                                      61

<210> SEQ ID NO 479
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 479
tggagttcag acgtgtgctc ttccgatctn nnnnnctgag tgtgcagaat cctaatatcg     60
gtta                                                                   64

<210> SEQ ID NO 480
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 480
tggagttcag acgtgtgctc ttccgatctn nnnnnagctc aatgttccac ctttgctcca     60
``` ca                                                                    62

<210> SEQ ID NO 481
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 481
tggagttcag acgtgtgctc ttccgatctn nnnnnctgag tctatccata tcttcacctg     60
gca                                                                   63

<210> SEQ ID NO 482
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 482
tggagttcag acgtgtgctc ttccgatctn nnnnngagtg ccatcgcatt gcaagagcta     60
ga                                                                    62

<210> SEQ ID NO 483
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 483
tggagttcag acgtgtgctc ttccgatctn nnnnnctgag gatccaactg tgcaatgtcc     60
aa                                                                    62

<210> SEQ ID NO 484
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 484
tggagttcag acgtgtgctc ttccgatctn nnnnncacag catggaaacc tagaaaccaa     60
cat                                                                   63

<210> SEQ ID NO 485
<211> LENGTH: 61
<212> TYPE: DNA

```
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 485
tggagttcag acgtgtgctc ttccgatctn nnnnnagtcg acacgagatg ccgagtctgc     60
a                                                                     61

<210> SEQ ID NO 486
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 486
tggagttcag acgtgtgctc ttccgatctn nnnnctatc ccggtctgcg ctaataaact      60
at                                                                    62

<210> SEQ ID NO 487
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 487
tggagttcag acgtgtgctc ttccgatctn nnnnatcag tgtaataaac ttgccttcat      60
ctgc                                                                  64

<210> SEQ ID NO 488
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 488
tggagttcag acgtgtgctc ttccgatctn nnnnatgcg ctgcgtccca catattagtg      60
ttt                                                                   63

<210> SEQ ID NO 489
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t
```

<400> SEQUENCE: 489
tggagttcag acgtgtgctc ttccgatctn nnnnnagtca tccggcatat gttaagtatt        60
ggc                                                                                            63

<210> SEQ ID NO 490
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 490
tggagttcag acgtgtgctc ttccgatctn nnnnnagctg ggggcagaaa tctaacaatc        60
aga                                                                                            63

<210> SEQ ID NO 491
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 491
tggagttcag acgtgtgctc ttccgatctn nnnnnctatt agtttacagt caaggggtag        60
agt                                                                                            63

<210> SEQ ID NO 492
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 492
tggagttcag acgtgtgctc ttccgatctn nnnnnagtcc cggataccgc gtatagagtg        60
a                                                                                              61

<210> SEQ ID NO 493
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 493
tggagttcag acgtgtgctc ttccgatctn nnnnnatcac ccttccccaa tatttttct        60 gct                                                                                            63

-continued

```
<210> SEQ ID NO 494
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 494
tggagttcag acgtgtgctc ttccgatctn nnnnngagtc agctagcttt tcagtccaca      60
gt                                                                    62

<210> SEQ ID NO 495
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 495
tggagttcag acgtgtgctc ttccgatctn nnnnngagtc ccgaaacttg gtcgtcgtag      60
t                                                                     61

<210> SEQ ID NO 496
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 496
tggagttcag acgtgtgctc ttccgatctn nnnnngcatc atcagcttca ctggtaccaa      60
cta                                                                   63

<210> SEQ ID NO 497
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 497
tggagttcag acgtgtgctc ttccgatctn nnnnnactag tctatggtgg ggagcgatcc      60
a                                                                     61

<210> SEQ ID NO 498
<211> LENGTH: 59
<212> TYPE: DNA
<213> ORGANISM: artificial sequence
<220> FEATURE:
<223> OTHER INFORMATION: allele 1 probe
```

-continued

```
<220> FEATURE:
<221> NAME/KEY: misc_feature
<222> LOCATION: (30)..(35)
<223> OTHER INFORMATION: n is a, c, g, or t

<400> SEQUENCE: 498
tggagttcag acgtgtgctc ttccgatctn nnnnnatcag cgagcagcgg tagggtgca          59

<210> SEQ ID NO 499
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 499
tggagttcag acgtgtgctc ttccgatctn nnnnnctgat gtgctttcta gagctggatg          60
ca                                                                          62

<210> SEQ ID NO 500
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 500
tggagttcag acgtgtgctc ttccgatctn nnnnnactag gatagctctg gagatgacat          60
ga                                                                          62

<210> SEQ ID NO 501
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 501
tggagttcag acgtgtgctc ttccgatctn nnnnncacat agcgaggtac ttaccacgta          60
att                                                                         63

<210> SEQ ID NO 502
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 502
tggagttcag acgtgtgctc ttccgatctn nnnnngcatt acgctgctgg atggaaagat          60
```

-continued

```
ga                                                              62

<210> SEQ ID NO 503
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 503
tggagttcag acgtgtgctc ttccgatctn nnnnnagtct tgggaacagt ggagtaacaa    60
aata                                                            64

<210> SEQ ID NO 504
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 504
tggagttcag acgtgtgctc ttccgatctn nnnnncgtgt tgtcagaacc cagatttact    60
caaa                                                            64

<210> SEQ ID NO 505
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 505
tggagttcag acgtgtgctc ttccgatctn nnnnnctatc cagctgaagt ttgtttgagg    60
ataa                                                            64

<210> SEQ ID NO 506
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 506
tggagttcag acgtgtgctc ttccgatctn nnnnngcatt agctgctctc ttcagtttca    60
gta                                                             63

<210> SEQ ID NO 507
<211> LENGTH: 64
<212> TYPE: DNA
<213> ORGANISM: artificial sequence
```

<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 507
tggagttcag acgtgtgctc ttccgatctn nnnnngcatg aaaatcttgc aaaacgttgg     60
actt                                                                 64

<210> SEQ ID NO 508
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 508
tggagttcag acgtgtgctc ttccgatctn nnnnnatcaa cggtatcctt tctgtcactg     60
ct                                                                   62

<210> SEQ ID NO 509
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 509
tggagttcag acgtgtgctc ttccgatctn nnnncacac tcatcaagat ctttcacagc      60
caa                                                                  63

<210> SEQ ID NO 510
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 510
tggagttcag acgtgtgctc ttccgatctn nnnntacta attggatggg taagctgctg      60
ga                                                                   62

<210> SEQ ID NO 511
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t -continued

<400> SEQUENCE: 511
tggagttcag acgtgtgctc ttccgatctn nnnncacag taactttgga cgataatcaa      60
gagat                                                                 65

<210> SEQ ID NO 512
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 512
tggagttcag acgtgtgctc ttccgatctn nnnnctgag ccaatcgagc atcccttgcg      60
t                                                                     61

<210> SEQ ID NO 513
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 513
tggagttcag acgtgtgctc ttccgatctn nnnnatcag gtagcagagg ttccacatga      60
at                                                                    62

<210> SEQ ID NO 514
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 514
tggagttcag acgtgtgctc ttccgatctn nnnnagtca tctaccacat cacaggaccg      60
aa                                                                    62

<210> SEQ ID NO 515
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 515
tggagttcag acgtgtgctc ttccgatctn nnnngagtc gttcgtcatg gttgacctag      60
ata                                                                   63

```
<210> SEQ ID NO 516
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 516
tggagttcag acgtgtgctc ttccgatctn nnnnngcatc gcaagagaca actccatgag      60
ct                                                                     62

<210> SEQ ID NO 517
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 517
tggagttcag acgtgtgctc ttccgatctn nnnnnacacc aggccggatt tcaaaagttt      60
agtt                                                                   64

<210> SEQ ID NO 518
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 518
tggagttcag acgtgtgctc ttccgatctn nnnnnacaca tctcagcacg gaaagttcta      60
caa                                                                    63

<210> SEQ ID NO 519
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 519
tggagttcag acgtgtgctc ttccgatctn nnnnngagtc tctgatttct tccggtttca      60
atat                                                                   64

<210> SEQ ID NO 520
<211> LENGTH: 64
<212> TYPE: DNA
<213> ORGANISM: artificial sequence
<220> FEATURE:
<223> OTHER INFORMATION: allele 1 probe
<220> FEATURE:
```

-continued

```
<221> NAME/KEY: misc_feature
<222> LOCATION: (30)..(35)
<223> OTHER INFORMATION: n is a, c, g, or t

<400> SEQUENCE: 520
tggagttcag acgtgtgctc ttccgatctn nnnncgtgt ctgatgtact gatacctttt      60
tcca                                                                  64

<210> SEQ ID NO 521
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 521
tggagttcag acgtgtgctc ttccgatctn nnnnctcga ttgtgctgaa aacgtgaatt      60
ctgt                                                                  64

<210> SEQ ID NO 522
<211> LENGTH: 60
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 522
tggagttcag acgtgtgctc ttccgatctn nnnnagctg gcccaatccc ggcgtctata      60

<210> SEQ ID NO 523
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 523
tggagttcag acgtgtgctc ttccgatctn nnnnctcgg gagtgttgtt tccattggta      60
cta                                                                   63

<210> SEQ ID NO 524
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 524
tggagttcag acgtgtgctc ttccgatctn nnnncacaa cctgctggat ctgctgaaga      60
c                                                                     61
```

```
<210> SEQ ID NO 525
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 525
tggagttcag acgtgtgctc ttccgatctn nnnnnactag ttgttacatc tcgtttctct        60
ttct                                                                     64

<210> SEQ ID NO 526
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 526
tggagttcag acgtgtgctc ttccgatctn nnnnngacgt tatccatgtc tccaggtgaa        60
gta                                                                      63

<210> SEQ ID NO 527
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 527
tggagttcag acgtgtgctc ttccgatctn nnnnnatgcg gttcaatgct ttacctcctc        60
tga                                                                      63

<210> SEQ ID NO 528
<211> LENGTH: 60
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 528
tggagttcag acgtgtgctc ttccgatctn nnnnnctcga tccagggcat cagcgcctct        60

<210> SEQ ID NO 529
<211> LENGTH: 63
<212> TYPE: DNA
<213> ORGANISM: artificial sequence
<220> FEATURE:
<223> OTHER INFORMATION: allele 1 probe
<220> FEATURE:
```

```
<221> NAME/KEY: misc_feature
<222> LOCATION: (30)..(35)
<223> OTHER INFORMATION: n is a, c, g, or t

<400> SEQUENCE: 529
tggagttcag acgtgtgctc ttccgatctn nnnnngcatg gcaaggtgaa gcttcactga      60
aat                                                                    63

<210> SEQ ID NO 530
<211> LENGTH: 60
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 530
tggagttcag acgtgtgctc ttccgatctn nnnnatcaa acgccagacg acgcgtctct       60

<210> SEQ ID NO 531
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 531
tggagttcag acgtgtgctc ttccgatctn nnnnctcga aaaacaccac caccatttca       60
ttttt                                                                  65

<210> SEQ ID NO 532
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 532
tggagttcag acgtgtgctc ttccgatctn nnnnactaa tggggaatct ctgcatgtaa       60
caa                                                                    63

<210> SEQ ID NO 533
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 533
tggagttcag acgtgtgctc ttccgatctn nnnnctcga gcagagccag ctaaaagatc       60
aat                                                                    63
```

<210> SEQ ID NO 534
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 534
tggagttcag acgtgtgctc ttccgatctn nnnnngcatg ctttagctgc acaactgcta        60
tga                                                                      63

<210> SEQ ID NO 535
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 535
tggagttcag acgtgtgctc ttccgatctn nnnnnatcag gtaagctctt gttttgttgc        60
tct                                                                      63

<210> SEQ ID NO 536
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 536
tggagttcag acgtgtgctc ttccgatctn nnnnnagctt gatgagatgc atacaaaatt        60
gcct                                                                     64

<210> SEQ ID NO 537
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 537
tggagttcag acgtgtgctc ttccgatctn nnnnnctcgt ccaggattgt tgttctgctt        60
tct                                                                      63

<210> SEQ ID NO 538
<211> LENGTH: 63
<212> TYPE: DNA
<213> ORGANISM: artificial sequence
<220> FEATURE:

```
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 538
tggagttcag acgtgtgctc ttccgatctn nnnnngacgt agcctgattg acaatgttgt      60
cct                                                                    63

<210> SEQ ID NO 539
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 539
tggagttcag acgtgtgctc ttccgatctn nnnnnctatg ggcactgatc taacaacctg      60
aa                                                                     62

<210> SEQ ID NO 540
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 540
tggagttcag acgtgtgctc ttccgatctn nnnnnatgcc cgctgctcgt gtctgaattc      60
tt                                                                     62

<210> SEQ ID NO 541
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 541
tggagttcag acgtgtgctc ttccgatctn nnnnncgtgc acgatgaagg cagcttcttc      60
aa                                                                     62

<210> SEQ ID NO 542
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 542
```

```
tggagttcag acgtgtgctc ttccgatctn nnnnnagtcg tctcataatt tcaaaatcgg      60
atgca                                                                  65

<210> SEQ ID NO 543
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 543
tggagttcag acgtgtgctc ttccgatctn nnnncgtga attaaggatg tctatcgacc      60
gga                                                                    63

<210> SEQ ID NO 544
<211> LENGTH: 66
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 544
tggagttcag acgtgtgctc ttccgatctn nnnnctcgg agtacaacaa gagaaaaaga      60
gaaata                                                                 66

<210> SEQ ID NO 545
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 545
tggagttcag acgtgtgctc ttccgatctn nnnnctgat gtatacattg tcttggggct      60
tatt                                                                   64

<210> SEQ ID NO 546
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 546
tggagttcag acgtgtgctc ttccgatctn nnnngagtc ctgcatcttt gtcctatcct      60
ata                                                                    63

<210> SEQ ID NO 547
```

-continued

```
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 547
tggagttcag acgtgtgctc ttccgatctn nnnnnctgag ctgctggaat ataattgggg      60
gt                                                                     62

<210> SEQ ID NO 548
<211> LENGTH: 60
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 548
tggagttcag acgtgtgctc ttccgatctn nnnnnagtcg aagacccgga ccggaaggaa      60

<210> SEQ ID NO 549
<211> LENGTH: 66
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 549
tggagttcag acgtgtgctc ttccgatctn nnnnnagtcc tctgatactt tctttcaaaa      60
cataaa                                                                 66

<210> SEQ ID NO 550
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 550
tggagttcag acgtgtgctc ttccgatctn nnnnacact cgccataaaa gttatgccac       60
cat                                                                    63

<210> SEQ ID NO 551
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t
```

<400> SEQUENCE: 551
tggagttcag acgtgtgctc ttccgatctn nnnnnatcag gcgagaaacc acaagttaaa      60
cga                                                                     63

<210> SEQ ID NO 552
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 552
tggagttcag acgtgtgctc ttccgatctn nnnnnctcga gtcagaacca atgccgtagt      60
aat                                                                     63

<210> SEQ ID NO 553
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 553
tggagttcag acgtgtgctc ttccgatctn nnnnncacat ctgctgctgt tgatagtgct      60
ac                                                                      62

<210> SEQ ID NO 554
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 554
tggagttcag acgtgtgctc ttccgatctn nnnnnctcgt agatcagacc aatgttatca      60
aacta                                                                   65

<210> SEQ ID NO 555
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 555
tggagttcag acgtgtgctc ttccgatctn nnnnnctatc gattaattaa tggcccctcc      60
tca                                                                     63

<210> SEQ ID NO 556
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 556
tggagttcag acgtgtgctc ttccgatctn nnnnnctgaa ctttgaacca ttggatggag      60
atc                                                                    63

<210> SEQ ID NO 557
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 557
tggagttcag acgtgtgctc ttccgatctn nnnncacaa cttaacaccg taaagtagag      60
ataaa                                                                  65

<210> SEQ ID NO 558
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 558
tggagttcag acgtgtgctc ttccgatctn nnnnnctgac atcaaatgtg aagtcgtcac      60
cat                                                                    63

<210> SEQ ID NO 559
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 559
tggagttcag acgtgtgctc ttccgatctn nnnnatgcc tacgagtaca tgcatataca      60
gtaa                                                                   64

<210> SEQ ID NO 560
<211> LENGTH: 63
<212> TYPE: DNA
<213> ORGANISM: artificial sequence
<220> FEATURE:
<223> OTHER INFORMATION: allele 1 probe -continued

```
<220> FEATURE:
<221> NAME/KEY: misc_feature
<222> LOCATION: (30)..(35)
<223> OTHER INFORMATION: n is a, c, g, or t

<400> SEQUENCE: 560
tggagttcag acgtgtgctc ttccgatctn nnnnngacgc atattccttg atgggcttct    60
gga                                                                  63

<210> SEQ ID NO 561
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 561
tggagttcag acgtgtgctc ttccgatctn nnnnncgtgt gcagccatct ctaccgacac    60
t                                                                    61

<210> SEQ ID NO 562
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 562
tggagttcag acgtgtgctc ttccgatctn nnnnnatgcc tttgtttttg gccgtgaaat    60
aaaaa                                                                65

<210> SEQ ID NO 563
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 563
tggagttcag acgtgtgctc ttccgatctn nnnnnctatc cggttagtac gccatagcga    60
at                                                                   62

<210> SEQ ID NO 564
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 564
```

-continued

```
tggagttcag acgtgtgctc ttccgatctn nnnnnatcag ctgtgctgcg catttctttg      60
ttt                                                                    63

<210> SEQ ID NO 565
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 565
tggagttcag acgtgtgctc ttccgatctn nnnnngacgc cttctgaaat cgaagtgcga      60
gaa                                                                    63

<210> SEQ ID NO 566
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 566
tggagttcag acgtgtgctc ttccgatctn nnnnngcatg ccgagccgat caagatagtg      60
t                                                                      61

<210> SEQ ID NO 567
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 567
tggagttcag acgtgtgctc ttccgatctn nnnnnctgag tcggtagatc acaagcatga      60
taa                                                                    63

<210> SEQ ID NO 568
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 568
tggagttcag acgtgtgctc ttccgatctn nnnnntacta agaatgtctt ccaaactgcc      60
tga                                                                    63

<210> SEQ ID NO 569
<211> LENGTH: 64
```

<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 569
tggagttcag acgtgtgctc ttccgatctn nnnnnacacc aaggtttttt tgtgaaagga        60
gtga                                                                     64

<210> SEQ ID NO 570
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 570
tggagttcag acgtgtgctc ttccgatctn nnnnnagctt ttgagggaaa tgatctagaa        60
tggt                                                                     64

<210> SEQ ID NO 571
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 571
tggagttcag acgtgtgctc ttccgatctn nnnngagtt ctaatttcag cagcaaactg         60
gct                                                                      63

<210> SEQ ID NO 572
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 572
tggagttcag acgtgtgctc ttccgatctn nnnnctcgc cgtcgtcgtt ctgacatgct         60
tt                                                                       62

<210> SEQ ID NO 573
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)

-continued

```
<223> OTHER INFORMATION: n is a, c, g, or t

<400> SEQUENCE: 573
tggagttcag acgtgtgctc ttccgatctn nnnnncacaa ctttagaaat ccgggtcatc     60
tttt                                                                  64

<210> SEQ ID NO 574
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 574
tggagttcag acgtgtgctc ttccgatctn nnnntactc gattgcttac actgttgcag     60
ct                                                                    62

<210> SEQ ID NO 575
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 575
tggagttcag acgtgtgctc ttccgatctn nnnnctcgc agcatataga agaggggaag     60
gat                                                                   63

<210> SEQ ID NO 576
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 576
tggagttcag acgtgtgctc ttccgatctn nnnncgtgg gagatggttg gtgagagtca     60
taa                                                                   63

<210> SEQ ID NO 577
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 577
tggagttcag acgtgtgctc ttccgatctn nnnnatgct gataagcatg tgcagcaact     60
tgt                                                                   63
```

```
<210> SEQ ID NO 578
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 578
tggagttcag acgtgtgctc ttccgatctn nnnnnctgac ctggacgtag tcgttgtcaa    60
ca                                                                    62

<210> SEQ ID NO 579
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 579
tggagttcag acgtgtgctc ttccgatctn nnnnnagtca catagagcgg gaaaaaaagt    60
ggt                                                                   63

<210> SEQ ID NO 580
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 580
tggagttcag acgtgtgctc ttccgatctn nnnnnactag ttgtaagtgc acaaaaataa    60
agcaa                                                                 65

<210> SEQ ID NO 581
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 581
tggagttcag acgtgtgctc ttccgatctn nnnnnatcaa ccaaattcaa gctgcaagtt    60
atct                                                                  64

<210> SEQ ID NO 582
<211> LENGTH: 63
<212> TYPE: DNA
<213> ORGANISM: artificial sequence
<220> FEATURE:
```

-continued

```
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 582
tggagttcag acgtgtgctc ttccgatctn nnnngcatc acatccgagt gaagagtaaa      60
caa                                                                    63

<210> SEQ ID NO 583
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 583
tggagttcag acgtgtgctc ttccgatctn nnnncacag gtaatccaca aagttaccag      60
cgt                                                                    63

<210> SEQ ID NO 584
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 584
tggagttcag acgtgtgctc ttccgatctn nnnntactc tagcatgcct ctgttatctg      60
caa                                                                    63

<210> SEQ ID NO 585
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 585
tggagttcag acgtgtgctc ttccgatctn nnnnacaca aatgtccaaa tcccgccgga      60
at                                                                     62

<210> SEQ ID NO 586
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 586
```

```
tggagttcag acgtgtgctc ttccgatctn nnnnnctgag ctggtagcag ccatgcatct    60
a                                                                     61

<210> SEQ ID NO 587
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 587
tggagttcag acgtgtgctc ttccgatctn nnnnnacact ggtatgacca aactaagtcg    60
aca                                                                   63

<210> SEQ ID NO 588
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 588
tggagttcag acgtgtgctc ttccgatctn nnnnntactg aaagcaccac aatcaggtca    60
aat                                                                   63

<210> SEQ ID NO 589
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 589
tggagttcag acgtgtgctc ttccgatctn nnnnnctgaa tgtgaactga agtagtttct    60
ttgtt                                                                 65

<210> SEQ ID NO 590
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 590
tggagttcag acgtgtgctc ttccgatctn nnnnnagctc tgaaaatgag gcagcacttt    60
catt                                                                  64

<210> SEQ ID NO 591
```

<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 591
tggagttcag acgtgtgctc ttccgatctn nnnnncacaa tcgtaaaagc tatggctgca      60
gaa      63

<210> SEQ ID NO 592
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 592
tggagttcag acgtgtgctc ttccgatctn nnnnnagtct tatggacggt gctcacaaaa      60
tga      63

<210> SEQ ID NO 593
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 593
tggagttcag acgtgtgctc ttccgatctn nnnnnagctt gccggcaagc tgagtaattt      60
ga      62

<210> SEQ ID NO 594
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 594
tggagttcag acgtgtgctc ttccgatctn nnnnncacac agtacagtct caagcaatcg      60
att      63

<210> SEQ ID NO 595
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 595
tggagttcag acgtgtgctc ttccgatctn nnnntactc ttaaacatcc tagatcggct        60
ctt                                                                     63

<210> SEQ ID NO 596
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 596
tggagttcag acgtgtgctc ttccgatctn nnnnacacg ttagttgtct tgcgctcatg        60
ca                                                                      62

<210> SEQ ID NO 597
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 597
tggagttcag acgtgtgctc ttccgatctn nnnngcatt gtctaggcct cctaagctta        60
ct                                                                      62

<210> SEQ ID NO 598
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 598
tggagttcag acgtgtgctc ttccgatctn nnnnactac agcaagctct attacatcaa        60
agaat                                                                   65

<210> SEQ ID NO 599
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 599
tggagttcag acgtgtgctc ttccgatctn nnnnatcag acagcatgca gcatcgttgc        60

-continued a                                                                                        61

<210> SEQ ID NO 600
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 600
tggagttcag acgtgtgctc ttccgatctn nnnnnatgca cacccccctta gatgctctat      60 ga                                                                                       62

<210> SEQ ID NO 601
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 601
tggagttcag acgtgtgctc ttccgatctn nnnntactc tgtagagggc agcaagtttc      60
aa                                                                                       62

<210> SEQ ID NO 602
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 602
tggagttcag acgtgtgctc ttccgatctn nnnnatgcg gacaaaagaa aaaggacaca      60
tgaat                                                                                    65

<210> SEQ ID NO 603
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 603
tggagttcag acgtgtgctc ttccgatctn nnnnctcgc cgtattagta cagtatttca      60
gagta                                                                                    65

<210> SEQ ID NO 604
<211> LENGTH: 60
<212> TYPE: DNA
<213> ORGANISM: artificial sequence -continued

```
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 604
tggagttcag acgtgtgctc ttccgatctn nnnnntactg cttgggctgc atcgcctgat        60

<210> SEQ ID NO 605
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 605
tggagttcag acgtgtgctc ttccgatctn nnnnngagtg attttcagct ttgcactaac        60
tgat                                                                     64

<210> SEQ ID NO 606
<211> LENGTH: 66
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 606
tggagttcag acgtgtgctc ttccgatctn nnnnnatgcg caaagttgat atcttttcca        60
atcttt                                                                   66

<210> SEQ ID NO 607
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 607
tggagttcag acgtgtgctc ttccgatctn nnnnctcgc ctgatgaagg caaaagggaa         60
aaa                                                                      63

<210> SEQ ID NO 608
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 608
```

```
tggagttcag acgtgtgctc ttccgatctn nnnnngcata gcaaacccgg atcagtaaca      60
att                                                                    63
```

<210> SEQ ID NO 609
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 609

```
tggagttcag acgtgtgctc ttccgatctn nnnnnctata tgattgcagt tggtttcatt      60
ttgat                                                                  65
```

<210> SEQ ID NO 610
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 610

```
tggagttcag acgtgtgctc ttccgatctn nnnnnagtca cgcaatacag cggtcacaac      60
at                                                                     62
```

<210> SEQ ID NO 611
<211> LENGTH: 66
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 611

```
tggagttcag acgtgtgctc ttccgatctn nnnnncgtgc aataagatta gcataaaata      60
gtcgtt                                                                 66
```

<210> SEQ ID NO 612
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 612

```
tggagttcag acgtgtgctc ttccgatctn nnnnntacta ttttcaccaa aattaagcag      60
gactt                                                                  65
```

<210> SEQ ID NO 613
<211> LENGTH: 62

<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 613
tggagttcag acgtgtgctc ttccgatctn nnnnngagtt ggtggttatt cgggcttttg    60
ca                                                                   62

<210> SEQ ID NO 614
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 614
tggagttcag acgtgtgctc ttccgatctn nnnnnatcaa agtggcattc agatcaacag    60
tca                                                                  63

<210> SEQ ID NO 615
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 615
tggagttcag acgtgtgctc ttccgatctn nnnncgtgg agagagagag agagagagat    60
ca                                                                   62

<210> SEQ ID NO 616
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 616
tggagttcag acgtgtgctc ttccgatctn nnnngacgg ccagtaactc tttcctccct    60
at                                                                   62

<210> SEQ ID NO 617
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)

<223> OTHER INFORMATION: n is a, c, g, or t

<400> SEQUENCE: 617
tggagttcag acgtgtgctc ttccgatctn nnnnnagtct caaaggagct agatcttctt        60
cga                                                                     63

<210> SEQ ID NO 618
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 618
tggagttcag acgtgtgctc ttccgatctn nnnnncgtgt gttgaactct ttgaacacat        60
catta                                                                   65

<210> SEQ ID NO 619
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 619
tggagttcag acgtgtgctc ttccgatctn nnnnnctcgg aagaacacaa ggcagattga        60
tgt                                                                     63

<210> SEQ ID NO 620
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 620
tggagttcag acgtgtgctc ttccgatctn nnnnngacgg caagtttgta tacttcaggg        60
gta                                                                     63

<210> SEQ ID NO 621
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 621
tggagttcag acgtgtgctc ttccgatctn nnnnngcatg gacgtccggc tgctactact        60
a                                                                       61

```
<210> SEQ ID NO 622
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 622
tggagttcag acgtgtgctc ttccgatctn nnnnnagctg actgtagttt tgtgcatctt      60
gaat                                                                  64

<210> SEQ ID NO 623
<211> LENGTH: 67
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 623
tggagttcag acgtgtgctc ttccgatctn nnnnnactac cagttgagtt cgtttattta      60
tttataa                                                               67

<210> SEQ ID NO 624
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 624
tggagttcag acgtgtgctc ttccgatctn nnnncacac aattggtagg gaaggggttc      60
ca                                                                    62

<210> SEQ ID NO 625
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 625
tggagttcag acgtgtgctc ttccgatctn nnnnagctc ccagcaccat gaaggttcat      60
ca                                                                    62

<210> SEQ ID NO 626
<211> LENGTH: 63
<212> TYPE: DNA
<213> ORGANISM: artificial sequence
<220> FEATURE:
```

<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 626
tggagttcag acgtgtgctc ttccgatctn nnnnnctgaa gaagcatggc cggttatata      60
ctt                                                                    63

<210> SEQ ID NO 627
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 627
tggagttcag acgtgtgctc ttccgatctn nnnnncacaa tccacagtaa tgtaaccact      60
gct                                                                    63

<210> SEQ ID NO 628
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 628
tggagttcag acgtgtgctc ttccgatctn nnnnnagctc ttcttgtcaa aaatgaggcc      60
agt                                                                    63

<210> SEQ ID NO 629
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 629
tggagttcag acgtgtgctc ttccgatctn nnnnnctgac gaaaataacc aaactgcact      60
tcta                                                                   64

<210> SEQ ID NO 630
<211> LENGTH: 66
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 630

```
tggagttcag acgtgtgctc ttccgatctn nnnnnctgac agaaaaattt aggcagcaca      60
aaaata                                                                 66
```

<210> SEQ ID NO 631
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 631

```
tggagttcag acgtgtgctc ttccgatctn nnnnncacat gttggaaaat cggtgtacca      60
tata                                                                   64
```

<210> SEQ ID NO 632
<211> LENGTH: 66
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 632

```
tggagttcag acgtgtgctc ttccgatctn nnnnnatcag gtttggttcg ttatattata      60
tatagt                                                                 66
```

<210> SEQ ID NO 633
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 633

```
tggagttcag acgtgtgctc ttccgatctn nnnnnctgat ggcagccatg tcagctacag      60
t                                                                      61
```

<210> SEQ ID NO 634
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 634

```
tggagttcag acgtgtgctc ttccgatctn nnnnnatcac cagctctaca ccaaggaatc      60
c                                                                      61
```

<210> SEQ ID NO 635

<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 635
tggagttcag acgtgtgctc ttccgatctn nnnnncgtgc aacctttgaa gagaacgtgc      60
atat                                                                    64

<210> SEQ ID NO 636
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 636
tggagttcag acgtgtgctc ttccgatctn nnnnnctgag gcaaggatta tctaagctgc      60
tat                                                                     63

<210> SEQ ID NO 637
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 637
tggagttcag acgtgtgctc ttccgatctn nnnnncgtgg gaccagacta ccagagacag      60
at                                                                      62

<210> SEQ ID NO 638
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 638
tggagttcag acgtgtgctc ttccgatctn nnnnntactc tgagttctgt ttattttggc      60
tgct                                                                    64

<210> SEQ ID NO 639
<211> LENGTH: 61
<212> TYPE: DNA
<213> ORGANISM: artificial sequence
<220> FEATURE:
<223> OTHER INFORMATION: allele 1 probe
<220> FEATURE:
<221> NAME/KEY: misc_feature -continued

```
<222> LOCATION: (30)..(35)
<223> OTHER INFORMATION: n is a, c, g, or t

<400> SEQUENCE: 639
tggagttcag acgtgtgctc ttccgatctn nnnnnacacc gactacgatg cccccattga     60
t                                                                     61

<210> SEQ ID NO 640
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 640
tggagttcag acgtgtgctc ttccgatctn nnnnngagtc atgaaacgac aacacattca     60
catt                                                                  64

<210> SEQ ID NO 641
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 641
tggagttcag acgtgtgctc ttccgatctn nnnnnctgag caattgtgtt tggaggcata     60
caa                                                                   63

<210> SEQ ID NO 642
<211> LENGTH: 66
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 642
tggagttcag acgtgtgctc ttccgatctn nnnnnagtca gaatgaagat gtgattatgc     60
tattaa                                                                66

<210> SEQ ID NO 643
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 643
tggagttcag acgtgtgctc ttccgatctn nnnnntactg ccatttttca catccagtga     60
```

-continued

```
tct                                                                                     63
```

```
<210> SEQ ID NO 644
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 644
tggagttcag acgtgtgctc ttccgatctn nnnnnagctg cgtaatgagt ccttgcagta      60
ca                                                                     62

<210> SEQ ID NO 645
<211> LENGTH: 64
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 645
tggagttcag acgtgtgctc ttccgatctn nnnnngcata acaaatgggt tatgcagaag      60
tagt                                                                   64

<210> SEQ ID NO 646
<211> LENGTH: 65
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 646
tggagttcag acgtgtgctc ttccgatctn nnnnnctgac tatatacgca tttgatgtgc      60
atgtt                                                                  65

<210> SEQ ID NO 647
<211> LENGTH: 60
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 647
tggagttcag acgtgtgctc ttccgatctn nnnnnactaa ccgggcttcc caccaaacga      60

<210> SEQ ID NO 648
<211> LENGTH: 63
<212> TYPE: DNA
<213> ORGANISM: artificial sequence
<220> FEATURE:
<223> OTHER INFORMATION: allele 1 probe
```

```
<220> FEATURE:
<221> NAME/KEY: misc_feature
<222> LOCATION: (30)..(35)
<223> OTHER INFORMATION: n is a, c, g, or t

<400> SEQUENCE: 648
tggagttcag acgtgtgctc ttccgatctn nnnncgtgt ttttaggaag gccagagtac        60
aca                                                                     63

<210> SEQ ID NO 649
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 649
tggagttcag acgtgtgctc ttccgatctn nnnntactc attgtttcca catcctcctt        60
aga                                                                     63

<210> SEQ ID NO 650
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 650
tggagttcag acgtgtgctc ttccgatctn nnnnatcac ccacacactc tcttgtcaat        60
att                                                                     63

<210> SEQ ID NO 651
<211> LENGTH: 63
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 651
tggagttcag acgtgtgctc ttccgatctn nnnnacacc caggttcttg gatgtttatg        60
gct                                                                     63

<210> SEQ ID NO 652
<211> LENGTH: 62
<212> TYPE: DNA
<213> ORGANISM: artificial sequence
<220> FEATURE:
<223> OTHER INFORMATION: allele 1 probe
<220> FEATURE:
<221> NAME/KEY: misc_feature
<222> LOCATION: (30)..(35)
<223> OTHER INFORMATION: n is a, c, g, or t

<400> SEQUENCE: 652
```

-continued

```
tggagttcag acgtgtgctc ttccgatctn nnnnnagctc agcaccgtgt ccctgtatgt      60
at                                                                     62
```

```
<210> SEQ ID NO 653
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 653
```

```
tggagttcag acgtgtgctc ttccgatctn nnnnntatgt ttcagtcgtt tcttctttgg      60
agc                                                                    63
```

```
<210> SEQ ID NO 654
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 654
```

```
tggagttcag acgtgtgctc ttccgatctn nnnnncgacc aaccgggtct gagacaagtt      60
c                                                                      61
```

```
<210> SEQ ID NO 655
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 655
```

```
tggagttcag acgtgtgctc ttccgatctn nnnnngtctc attcagcagc attctttttg      60
tcc                                                                    63
```

```
<210> SEQ ID NO 656
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 656
```

```
tggagttcag acgtgtgctc ttccgatctn nnnnntcagg ctcaaaacca agagatcgac      60
cc                                                                     62
```

```
<210> SEQ ID NO 657
<211> LENGTH: 60
```

```
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 657
tggagttcag acgtgtgctc ttccgatctn nnnngcgca catggcagag gcagaccacc     60

<210> SEQ ID NO 658
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 658
tggagttcag acgtgtgctc ttccgatctn nnnnagagc ctaaagaccg ataccaactt     60
ttg                                                                  63

<210> SEQ ID NO 659
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 659
tggagttcag acgtgtgctc ttccgatctn nnnngtacg aggtggaaga ggaagcccaa     60
g                                                                    61

<210> SEQ ID NO 660
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 660
tggagttcag acgtgtgctc ttccgatctn nnnntgtag cttgagtagg agcgtcacat     60
tc                                                                   62

<210> SEQ ID NO 661
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t
```

```
<400> SEQUENCE: 661
tggagttcag acgtgtgctc ttccgatctn nnnnngcgca ttcatgcaat caagcacttt      60
agag                                                                    64

<210> SEQ ID NO 662
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 662
tggagttcag acgtgtgctc ttccgatctn nnnnngtacg aagaaaaatc ctgagaacgc      60
cg                                                                      62

<210> SEQ ID NO 663
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 663
tggagttcag acgtgtgctc ttccgatctn nnnncgacc acttattatc gttggaccac       60
gag                                                                     63

<210> SEQ ID NO 664
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 664
tggagttcag acgtgtgctc ttccgatctn nnnncagcc ctggatcaaa aagggtcttc       60
ag                                                                      62

<210> SEQ ID NO 665
<211> LENGTH: 65
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 665
tggagttcag acgtgtgctc ttccgatctn nnnntctcg tgaattgttg caggtaaaaa       60
attgc                                                                   65
```

-continued

```
<210> SEQ ID NO 666
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 666
tggagttcag acgtgtgctc ttccgatctn nnnnntctca actgcaatga aaaatggatt      60
ggtg                                                                   64

<210> SEQ ID NO 667
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 667
tggagttcag acgtgtgctc ttccgatctn nnnnntgtag gcgaactagt ccacaaattc      60
atc                                                                    63

<210> SEQ ID NO 668
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 668
tggagttcag acgtgtgctc ttccgatctn nnnnngtacg acgtgacgtg aacaaaccaa      60
gg                                                                     62

<210> SEQ ID NO 669
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 669
tggagttcag acgtgtgctc ttccgatctn nnnnngtctc gtgtggcgtc ccctgattg      60

<210> SEQ ID NO 670
<211> LENGTH: 59
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
```

-continued

```
<223> OTHER INFORMATION: n is a, c, g, or t

<400> SEQUENCE: 670
tggagttcag acgtgtgctc ttccgatctn nnnnngtact ccgggcagct aggagggtg        59

<210> SEQ ID NO 671
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 671
tggagttcag acgtgtgctc ttccgatctn nnnnngctga cttgattgat ctaataaagc        60
agcg        64

<210> SEQ ID NO 672
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 672
tggagttcag acgtgtgctc ttccgatctn nnnnngcgcg caccgtacca atatctctgg        60
ac        62

<210> SEQ ID NO 673
<211> LENGTH: 65
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 673
tggagttcag acgtgtgctc ttccgatctn nnnnngcgcg tgtgtggtac aaacaaatga        60
acatt        65

<210> SEQ ID NO 674
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 674
tggagttcag acgtgtgctc ttccgatctn nnnncagcc tgctgcggct gagtgttgac        60

<210> SEQ ID NO 675
<211> LENGTH: 63
```

```
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 675
tggagttcag acgtgtgctc ttccgatctn nnnngcgcc atagctatgc tatggttcgc      60
atg                                                                    63

<210> SEQ ID NO 676
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 676
tggagttcag acgtgtgctc ttccgatctn nnnntgcgg ctatcatcat cagagaaacc      60
attc                                                                   64

<210> SEQ ID NO 677
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 677
tggagttcag acgtgtgctc ttccgatctn nnnncagct gcatggctgc atcgctttca      60
g                                                                      61

<210> SEQ ID NO 678
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 678
tggagttcag acgtgtgctc ttccgatctn nnnnacgtc cttgcacttt taatcttaac      60
tacc                                                                   64

<210> SEQ ID NO 679
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
```

<223> OTHER INFORMATION: n is a, c, g, or t

<400> SEQUENCE: 679
tggagttcag acgtgtgctc ttccgatctn nnnnntgatt ggtttggcag acgatcacac      60
g                                                                     61

<210> SEQ ID NO 680
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 680
tggagttcag acgtgtgctc ttccgatctn nnnnncgacc tgtactcaca cacagggcaa      60
c                                                                     61

<210> SEQ ID NO 681
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 681
tggagttcag acgtgtgctc ttccgatctn nnnnngtcta gatttctgaa aacctaagcc      60
cag                                                                   63

<210> SEQ ID NO 682
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 682
tggagttcag acgtgtgctc ttccgatctn nnnnngcgcc caaggataat cttgttccat      60
ctg                                                                   63

<210> SEQ ID NO 683
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 683
tggagttcag acgtgtgctc ttccgatctn nnnnncagcc agatgaaact tagtatggtg      60
tagc                                                                  64

```
<210> SEQ ID NO 684
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 684
tggagttcag acgtgtgctc ttccgatctn nnnntgtac ggcaagtaca gtcatctctc      60
tc                                                                    62

<210> SEQ ID NO 685
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 685
tggagttcag acgtgtgctc ttccgatctn nnnncagcg caacttggag catctctaca      60
tg                                                                    62

<210> SEQ ID NO 686
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 686
tggagttcag acgtgtgctc ttccgatctn nnnnacgtt agcagcaacc actttatctg      60
atg                                                                   63

<210> SEQ ID NO 687
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 687
tggagttcag acgtgtgctc ttccgatctn nnnntgata catccggccc aaacttctga      60
g                                                                     61

<210> SEQ ID NO 688
<211> LENGTH: 63
<212> TYPE: DNA
<213> ORGANISM: artificial sequence
<220> FEATURE:
```

<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 688
tggagttcag acgtgtgctc ttccgatctn nnnngcgcg aagtctagct aactgtggat      60
ttg                                                                     63

<210> SEQ ID NO 689
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 689
tggagttcag acgtgtgctc ttccgatctn nnnntcaga caagcgtcaa ccaaagagcc      60
c                                                                       61

<210> SEQ ID NO 690
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 690
tggagttcag acgtgtgctc ttccgatctn nnnngtacc tacgcgtacc aggaaagata      60
gc                                                                      62

<210> SEQ ID NO 691
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 691
tggagttcag acgtgtgctc ttccgatctn nnnntgata tctcagtcgc cagtttctct      60
tc                                                                      62

<210> SEQ ID NO 692
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 692

```
tggagttcag acgtgtgctc ttccgatctn nnnnncagcc agttggcata ataacattga     60
ccc                                                                    63
```

```
<210> SEQ ID NO 693
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 693
```

```
tggagttcag acgtgtgctc ttccgatctn nnnnntgtag ctaatatgtc tgctattgac     60
ctg                                                                    63
```

```
<210> SEQ ID NO 694
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 694
```

```
tggagttcag acgtgtgctc ttccgatctn nnnnntagac acgtcaacgg tgcgtagtgc     60
```

```
<210> SEQ ID NO 695
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 695
```

```
tggagttcag acgtgtgctc ttccgatctn nnnnntgatc tcagggatca tgtgtgctca     60
c                                                                      61
```

```
<210> SEQ ID NO 696
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 696
```

```
tggagttcag acgtgtgctc ttccgatctn nnnnntcagt agcaaccaca cagacacagg     60
c                                                                      61
```

```
<210> SEQ ID NO 697
<211> LENGTH: 64
<212> TYPE: DNA
```

-continued

<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 697
tggagttcag acgtgtgctc ttccgatctn nnnnntatgt cagaaaaaac tatgacagtc      60
tctc                                                                     64

<210> SEQ ID NO 698
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 698
tggagttcag acgtgtgctc ttccgatctn nnnncgaca tctgttgtga aaagaaacc      60 caac                                                                     64

<210> SEQ ID NO 699
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 699
tggagttcag acgtgtgctc ttccgatctn nnnntagag tagcccattg tgcctcttgt      60
tg                                                                       62

<210> SEQ ID NO 700
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 700
tggagttcag acgtgtgctc ttccgatctn nnnncagct catccccact ccaactacca      60
c                                                                        61

<210> SEQ ID NO 701
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t -continued

<400> SEQUENCE: 701
tggagttcag acgtgtgctc ttccgatctn nnnntctcc tagatcctat ggccaaagaa      60
gg                                                                     62

<210> SEQ ID NO 702
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 702
tggagttcag acgtgtgctc ttccgatctn nnnnngtacg ttgttacaac ggagaagaac      60
gg                                                                     62

<210> SEQ ID NO 703
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 703
tggagttcag acgtgtgctc ttccgatctn nnnntgcgg gccgggacag tagtatcagt      60
c                                                                      61

<210> SEQ ID NO 704
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 704
tggagttcag acgtgtgctc ttccgatctn nnnnngtacg gccatttctt tcacacaatc      60
gc                                                                     62

<210> SEQ ID NO 705
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 705
tggagttcag acgtgtgctc ttccgatctn nnnngctgc agttcgcacc ctgtgtaata      60
cg                                                                     62

-continued

```
<210> SEQ ID NO 706
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 706
tggagttcag acgtgtgctc ttccgatctn nnnnngcgcg tctagctgca ctggctactg     60
c                                                                     61

<210> SEQ ID NO 707
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 707
tggagttcag acgtgtgctc ttccgatctn nnnnntatgg acacgataat cctctttggg     60
tc                                                                    62

<210> SEQ ID NO 708
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 708
tggagttcag acgtgtgctc ttccgatctn nnnnngcgct tacatgaaaa ggaagcttgt     60
ttcg                                                                  64

<210> SEQ ID NO 709
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 709
tggagttcag acgtgtgctc ttccgatctn nnnntctct ggttgctgct caagtctacg      60
c                                                                     61

<210> SEQ ID NO 710
<211> LENGTH: 63
<212> TYPE: DNA
<213> ORGANISM: artificial sequence
<220> FEATURE:
<223> OTHER INFORMATION: allele 2 probe
```

<220> FEATURE:
<221> NAME/KEY: misc_feature
<222> LOCATION: (30)..(35)
<223> OTHER INFORMATION: n is a, c, g, or t

<400> SEQUENCE: 710
tggagttcag acgtgtgctc ttccgatctn nnnnntgtaa gtgagatgac agtgatatgg      60
ttc                                                                    63

<210> SEQ ID NO 711
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 711
tggagttcag acgtgtgctc ttccgatctn nnnnngtctg cttaacatgg tttctgctga      60
gg                                                                     62

<210> SEQ ID NO 712
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 712
tggagttcag acgtgtgctc ttccgatctn nnnnntctct caaactaacc gttggatgag      60
gc                                                                     62

<210> SEQ ID NO 713
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 713
tggagttcag acgtgtgctc ttccgatctn nnnnncgacc gttatgaagc tgttgcaagg      60
ag                                                                     62

<210> SEQ ID NO 714
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 714
tggagttcag acgtgtgctc ttccgatctn nnnnntgcgc agcagccatt cgttccacag        60
c                                                                        61

<210> SEQ ID NO 715
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 715
tggagttcag acgtgtgctc ttccgatctn nnnnngtcta gatggagaaa ttgtaaccgg        60
cg                                                                       62

<210> SEQ ID NO 716
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 716
tggagttcag acgtgtgctc ttccgatctn nnnnntagac acacaattga tctgcagtga        60
cg                                                                       62

<210> SEQ ID NO 717
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 717
tggagttcag acgtgtgctc ttccgatctn nnnnntgtaa gtcccacgtg gtacataatt        60
cg                                                                       62

<210> SEQ ID NO 718
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 718
tggagttcag acgtgtgctc ttccgatctn nnnnntatgg gtcgttaatc acgagatcaa        60
cg                                                                       62

<210> SEQ ID NO 719
<211> LENGTH: 64

```
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 719
tggagttcag acgtgtgctc ttccgatctn nnnnncgact gaaaaacctt tggaataagt      60
gctc                                                                   64

<210> SEQ ID NO 720
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 720
tggagttcag acgtgtgctc ttccgatctn nnnnncgact tctgacgtct caactgttcc      60
tg                                                                     62

<210> SEQ ID NO 721
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 721
tggagttcag acgtgtgctc ttccgatctn nnnnagagc gacttctcta gttcctcagt       60
cc                                                                     62

<210> SEQ ID NO 722
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 722
tggagttcag acgtgtgctc ttccgatctn nnnntgtag gaatttcttg gagaagttcc       60
cc                                                                     62

<210> SEQ ID NO 723
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
```

-continued

```
<223> OTHER INFORMATION: n is a, c, g, or t

<400> SEQUENCE: 723
tggagttcag acgtgtgctc ttccgatctn nnnnntgatt ggtatttata ctgtgagctg      60
agg                                                                    63

<210> SEQ ID NO 724
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 724
tggagttcag acgtgtgctc ttccgatctn nnnnntgcgg ctcaagagga aaatcagcat      60
cc                                                                     62

<210> SEQ ID NO 725
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 725
tggagttcag acgtgtgctc ttccgatctn nnnntctca gtatgtgttt gatcgcgcta      60
gc                                                                     62

<210> SEQ ID NO 726
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 726
tggagttcag acgtgtgctc ttccgatctn nnnnagaga ggtaatttat aggcggctga      60
ttg                                                                    63

<210> SEQ ID NO 727
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 727
tggagttcag acgtgtgctc ttccgatctn nnnngtctc cggctattgc agacaaaaag      60
ag                                                                     62
```

```
<210> SEQ ID NO 728
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 728
tggagttcag acgtgtgctc ttccgatctn nnnnngctgt tgtgggagag gaattctggc      60
g                                                                       61

<210> SEQ ID NO 729
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 729
tggagttcag acgtgtgctc ttccgatctn nnnntctcc tcgtcttctt tcacctctcc       60
g                                                                       61

<210> SEQ ID NO 730
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 730
tggagttcag acgtgtgctc ttccgatctn nnnngctga gtacaacctt gcagattttg       60
gtg                                                                     63

<210> SEQ ID NO 731
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 731
tggagttcag acgtgtgctc ttccgatctn nnnngcgca gttgtagatc tgggggttac       60
tc                                                                      62

<210> SEQ ID NO 732
<211> LENGTH: 61
<212> TYPE: DNA
<213> ORGANISM: artificial sequence
<220> FEATURE:
```

<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 732
tggagttcag acgtgtgctc ttccgatctn nnnnntcagg ctctcactag agcccctaca      60
c                                                                     61

<210> SEQ ID NO 733
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 733
tggagttcag acgtgtgctc ttccgatctn nnnnntctcg tacggtggtt ggaacagtaa      60
cc                                                                    62

<210> SEQ ID NO 734
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 734
tggagttcag acgtgtgctc ttccgatctn nnnnngtacc gtatacacgc acatgtgtgt      60
gc                                                                    62

<210> SEQ ID NO 735
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 735
tggagttcag acgtgtgctc ttccgatctn nnnnntgtat gagctgcagt ttgcttctta      60
cg                                                                    62

<210> SEQ ID NO 736
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 736

-continued

```
tggagttcag acgtgtgctc ttccgatctn nnnnngtacg gaccaacttg tcggcgccag       60

<210> SEQ ID NO 737
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 737
tggagttcag acgtgtgctc ttccgatctn nnnnntgtag catgcggaaa ataatggagt       60
acc                                                                     63

<210> SEQ ID NO 738
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 738
tggagttcag acgtgtgctc ttccgatctn nnnnnagaga aaacacattc tgcaagcaaa       60
acac                                                                    64

<210> SEQ ID NO 739
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 739
tggagttcag acgtgtgctc ttccgatctn nnnnntagat tgaggagggt gctgcaagat       60
c                                                                       61

<210> SEQ ID NO 740
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 740
tggagttcag acgtgtgctc ttccgatctn nnnnntgatg ggtgtacatt ggtttgcttg       60
cc                                                                      62

<210> SEQ ID NO 741
<211> LENGTH: 61
<212> TYPE: DNA
```

```
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 741
tggagttcag acgtgtgctc ttccgatctn nnnncagca tcgtgcttct ccaggtaacg     60
g                                                                    61

<210> SEQ ID NO 742
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 742
tggagttcag acgtgtgctc ttccgatctn nnnnacgtt atggccgatc tgggtagtgt     60
g                                                                    61

<210> SEQ ID NO 743
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 743
tggagttcag acgtgtgctc ttccgatctn nnnngtctg ggtgtctggt tcttcaaaca     60
gc                                                                   62

<210> SEQ ID NO 744
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 744
tggagttcag acgtgtgctc ttccgatctn nnnntgatg atcgagctga ttagtttcta     60
gag                                                                  63

<210> SEQ ID NO 745
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t
```

-continued

<400> SEQUENCE: 745
tggagttcag acgtgtgctc ttccgatctn nnnncagcg gcttcatgtt tctcccaaaa    60
aag                                                                63

<210> SEQ ID NO 746
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 746
tggagttcag acgtgtgctc ttccgatctn nnnntctca agccctctaa gttcatcgac    60
tc                                                                 62

<210> SEQ ID NO 747
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 747
tggagttcag acgtgtgctc ttccgatctn nnnngtact tgaaatgctt tctaatggtg    60
ggg                                                                63

<210> SEQ ID NO 748
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 748
tggagttcag acgtgtgctc ttccgatctn nnnntgtat acagcaacat cataacacat    60
atgc                                                               64

<210> SEQ ID NO 749
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 749
tggagttcag acgtgtgctc ttccgatctn nnnntctct aatcctttgc cgtgctcagc    60
c                                                                  61

```
<210> SEQ ID NO 750
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 750
tggagttcag acgtgtgctc ttccgatctn nnnnntgtag ttttggatcc tcaaagagaa        60
ggc                                                                       63

<210> SEQ ID NO 751
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 751
tggagttcag acgtgtgctc ttccgatctn nnnnnagaga ccctgttgtt ggctatacag        60
ac                                                                        62

<210> SEQ ID NO 752
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 752
tggagttcag acgtgtgctc ttccgatctn nnnnntatgt tatcccgggc aagtccatga        60
c                                                                         61

<210> SEQ ID NO 753
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 753
tggagttcag acgtgtgctc ttccgatctn nnnncgacg caggtgcaga caacggcaag        60

<210> SEQ ID NO 754
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
```

-continued

```
<222> LOCATION: (30)..(35)
<223> OTHER INFORMATION: n is a, c, g, or t

<400> SEQUENCE: 754
tggagttcag acgtgtgctc ttccgatctn nnnnntgcgc cgatcgggcg gttgagatcc      60

<210> SEQ ID NO 755
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 755
tggagttcag acgtgtgctc ttccgatctn nnnnntgtat cggtcacgg cggttgaatt      60 g                                                                     61

<210> SEQ ID NO 756
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 756
tggagttcag acgtgtgctc ttccgatctn nnnnnacgtt gcagcagcaa cccacggttc      60

<210> SEQ ID NO 757
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 757
tggagttcag acgtgtgctc ttccgatctn nnnnntgatt ctagaatgaa tttagcagac      60
ttgg                                                                  64

<210> SEQ ID NO 758
<211> LENGTH: 65
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 758
tggagttcag acgtgtgctc ttccgatctn nnnnnagagt cttttctttt acaacagact      60
tacag                                                                 65

<210> SEQ ID NO 759
```

<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 759
tggagttcag acgtgtgctc ttccgatctn nnnnntcagt cctgctggtc agcgtttcta      60
c                                                                     61

<210> SEQ ID NO 760
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 760
tggagttcag acgtgtgctc ttccgatctn nnnnntatgt aatagcgatg tgtttcagtt      60
gcg                                                                   63

<210> SEQ ID NO 761
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 761
tggagttcag acgtgtgctc ttccgatctn nnnntctct gcagcctccg gtcacacaag       60

<210> SEQ ID NO 762
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 762
tggagttcag acgtgtgctc ttccgatctn nnnntgcgc atcgtcacag tcagtagtag       60
cc                                                                    62

<210> SEQ ID NO 763
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 763
tggagttcag acgtgtgctc ttccgatctn nnnnngctgg acacgatgat gtggagaaag        60
gg                                                                       62

<210> SEQ ID NO 764
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 764
tggagttcag acgtgtgctc ttccgatctn nnnnnagagg cattagattc gccacttagg        60
ac                                                                       62

<210> SEQ ID NO 765
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 765
tggagttcag acgtgtgctc ttccgatctn nnnnngtctc aggagacaga gttctgcaca        60
ac                                                                       62

<210> SEQ ID NO 766
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 766
tggagttcag acgtgtgctc ttccgatctn nnnnncgaca ttagctgagt caattcagtc        60
ctg                                                                      63

<210> SEQ ID NO 767
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 767
tggagttcag acgtgtgctc ttccgatctn nnnnnagagg acgactaacg tgtcttgctt        60
cc                                                                       62

<210> SEQ ID NO 768
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 768
tggagttcag acgtgtgctc ttccgatctn nnnnngtctc aaaacaccag tagcatgcac      60
tac                                                                    63

<210> SEQ ID NO 769
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 769
tggagttcag acgtgtgctc ttccgatctn nnnntagac caaccgatcg agcgagcatg      60

<210> SEQ ID NO 770
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 770
tggagttcag acgtgtgctc ttccgatctn nnnntatgt cacaaaagca tttggcgcta      60
cc                                                                     62

<210> SEQ ID NO 771
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 771
tggagttcag acgtgtgctc ttccgatctn nnnncagca gagctgagag cagtggacgc      60

<210> SEQ ID NO 772
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t -continued

<400> SEQUENCE: 772
tggagttcag acgtgtgctc ttccgatctn nnnnntctct ctgaagtcct tgtccagtaa      60
aac                                                                    63

<210> SEQ ID NO 773
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 773
tggagttcag acgtgtgctc ttccgatctn nnnnntcagg tgacagttgt caaacagacc      60
aac                                                                    63

<210> SEQ ID NO 774
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 774
tggagttcag acgtgtgctc ttccgatctn nnnnntagaa tattaagatt gtgtgctgca      60
agtc                                                                   64

<210> SEQ ID NO 775
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 775
tggagttcag acgtgtgctc ttccgatctn nnnnntgata gcggttgcaa taaaccagcc      60
g                                                                      61

<210> SEQ ID NO 776
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 776
tggagttcag acgtgtgctc ttccgatctn nnnnntctca tcggatgtgc ggtcaagaac      60
c                                                                      61

<210> SEQ ID NO 777
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 777
tggagttcag acgtgtgctc ttccgatctn nnnnngtacc catactaagc tgccactcac      60
tc                                                                     62

<210> SEQ ID NO 778
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 778
tggagttcag acgtgtgctc ttccgatctn nnnnntagag gtgtgtcctc atcctcatcg      60
g                                                                      61

<210> SEQ ID NO 779
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 779
tggagttcag acgtgtgctc ttccgatctn nnnnntagat tcagactttc agctgcgatg      60
ag                                                                     62

<210> SEQ ID NO 780
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 780
tggagttcag acgtgtgctc ttccgatctn nnnngctgt catcttcccg gtccgaacgg       60

<210> SEQ ID NO 781
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature -continued
<222> LOCATION: (30)..(35)
<223> OTHER INFORMATION: n is a, c, g, or t

<400> SEQUENCE: 781
tggagttcag acgtgtgctc ttccgatctn nnnnntgatc ctcagtacca agacgacgaa      60
gt                                                                    62

<210> SEQ ID NO 782
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 782
tggagttcag acgtgtgctc ttccgatctn nnnnnacgtc gctgcaaaag gatggggctc      60

<210> SEQ ID NO 783
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 783
tggagttcag acgtgtgctc ttccgatctn nnnnntcagc aaggtggacc agaagagaaa      60
cc                                                                    62

<210> SEQ ID NO 784
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 784
tggagttcag acgtgtgctc ttccgatctn nnnnncgacg caaagccttc atttgtgcct      60
cc                                                                    62

<210> SEQ ID NO 785
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 785
tggagttcag acgtgtgctc ttccgatctn nnnnnagagc aaaaccaacg cagggtgttt      60
cg                                                                    62

<210> SEQ ID NO 786
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 786
tggagttcag acgtgtgctc ttccgatctn nnnnnacgtc tggctgctct ctggcaaaaa    60
ac                                                                   62

<210> SEQ ID NO 787
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 787
tggagttcag acgtgtgctc ttccgatctn nnnnntgcgc agagtactac cagttgctcg    60
tat                                                                  63

<210> SEQ ID NO 788
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 788
tggagttcag acgtgtgctc ttccgatctn nnnnncgaca ttgccatgtg atgctgagga    60
ag                                                                   62

<210> SEQ ID NO 789
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 789
tggagttcag acgtgtgctc ttccgatctn nnnnnagaga tgcatctggg actgctctga    60
c                                                                    61

<210> SEQ ID NO 790
<211> LENGTH: 62
<212> TYPE: DNA
<213> ORGANISM: artificial sequence
<220> FEATURE:
<223> OTHER INFORMATION: allele 2 probe -continued

```
<220> FEATURE:
<221> NAME/KEY: misc_feature
<222> LOCATION: (30)..(35)
<223> OTHER INFORMATION: n is a, c, g, or t

<400> SEQUENCE: 790
tggagttcag acgtgtgctc ttccgatctn nnnnntcagc gcagcgaaca gaattctcga      60
tc                                                                     62

<210> SEQ ID NO 791
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 791
tggagttcag acgtgtgctc ttccgatctn nnnntctct agccgagcta gggatcctcg       60

<210> SEQ ID NO 792
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 792
tggagttcag acgtgtgctc ttccgatctn nnnnacgtc ctacatcggc atatctacca       60
tg                                                                     62

<210> SEQ ID NO 793
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 793
tggagttcag acgtgtgctc ttccgatctn nnnngtacc aacacagctg caaaacatgc       60
atc                                                                    63

<210> SEQ ID NO 794
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 794
tggagttcag acgtgtgctc ttccgatctn nnnntgatc gtttgctgca tgttttcaga       60
```

-continued

```
cg                                                                        62

<210> SEQ ID NO 795
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 795
tggagttcag acgtgtgctc ttccgatctn nnnnntatgg tcctctggga tttcggcgcc      60

<210> SEQ ID NO 796
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 796
tggagttcag acgtgtgctc ttccgatctn nnnncagct gaccaatggt tagctgacat        60
gg                                                                        62

<210> SEQ ID NO 797
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 797
tggagttcag acgtgtgctc ttccgatctn nnnngctgg cccttcgttg tcctgaacat        60
g                                                                         61

<210> SEQ ID NO 798
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 798
tggagttcag acgtgtgctc ttccgatctn nnnntgtag aaagaagcta ctaatgacct        60
gcg                                                                       63

<210> SEQ ID NO 799
<211> LENGTH: 63
<212> TYPE: DNA
<213> ORGANISM: artificial sequence
<220> FEATURE:
<223> OTHER INFORMATION: allele 2 probe
```

-continued

```
<220> FEATURE:
<221> NAME/KEY: misc_feature
<222> LOCATION: (30)..(35)
<223> OTHER INFORMATION: n is a, c, g, or t

<400> SEQUENCE: 799
tggagttcag acgtgtgctc ttccgatctn nnnnntgatg aatcagagca tcctgaatac      60
acg                                                                    63

<210> SEQ ID NO 800
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 800
tggagttcag acgtgtgctc ttccgatctn nnnnngtctg agtcattatt ctccatcgcc      60
cc                                                                     62

<210> SEQ ID NO 801
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 801
tggagttcag acgtgtgctc ttccgatctn nnnnntcagg ccctctgacc tagctagtta      60
c                                                                      61

<210> SEQ ID NO 802
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 802
tggagttcag acgtgtgctc ttccgatctn nnnnagagc tattgagcag tcatccgtct       60
ac                                                                     62

<210> SEQ ID NO 803
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 803
```

-continued

```
tggagttcag acgtgtgctc ttccgatctn nnnntctct agtgctacag ctacacaagt     60
gg                                                                    62

<210> SEQ ID NO 804
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 804
tggagttcag acgtgtgctc ttccgatctn nnnnacgtg tatgctggcc gcaggtacag      60

<210> SEQ ID NO 805
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 805
tggagttcag acgtgtgctc ttccgatctn nnnntagat gtgcagaatc ctaatatcgg      60
ttg                                                                   63

<210> SEQ ID NO 806
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 806
tggagttcag acgtgtgctc ttccgatctn nnnngtctc aatgttccac ctttgctcca      60
cc                                                                    62

<210> SEQ ID NO 807
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 807
tggagttcag acgtgtgctc ttccgatctn nnnntagat ctatccatat cttcacctgg      60
cg                                                                    62

<210> SEQ ID NO 808
<211> LENGTH: 61
<212> TYPE: DNA
<213> ORGANISM: artificial sequence
```

```
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 808
tggagttcag acgtgtgctc ttccgatctn nnnnngtacc catcgcattg caagagctag      60
g                                                                       61

<210> SEQ ID NO 809
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 809
tggagttcag acgtgtgctc ttccgatctn nnnnntagag gatccaactg tgcaatgtcc      60
ag                                                                      62

<210> SEQ ID NO 810
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 810
tggagttcag acgtgtgctc ttccgatctn nnnnntatgg catggaaacc tagaaaccaa      60
cac                                                                     63

<210> SEQ ID NO 811
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 811
tggagttcag acgtgtgctc ttccgatctn nnnnngctga cacgagatgc cgagtctgcg      60

<210> SEQ ID NO 812
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 812
```

-continued

```
tggagttcag acgtgtgctc ttccgatctn nnnnncgacc ccggtctgcg ctaataaact      60
ac                                                                     62

<210> SEQ ID NO 813
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 813
tggagttcag acgtgtgctc ttccgatctn nnnnntgcgg tgtaataaac ttgccttcat      60
ctgg                                                                   64

<210> SEQ ID NO 814
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 814
tggagttcag acgtgtgctc ttccgatctn nnnnncagcc tgcgtcccac atattagtgt      60
tg                                                                     62

<210> SEQ ID NO 815
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 815
tggagttcag acgtgtgctc ttccgatctn nnnnngctga tccggcatat gttaagtatt      60
ggg                                                                    63

<210> SEQ ID NO 816
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 816
tggagttcag acgtgtgctc ttccgatctn nnnnngtctg gggcagaaat ctaacaatca      60
gc                                                                     62

<210> SEQ ID NO 817
<211> LENGTH: 62
```

```
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 817
tggagttcag acgtgtgctc ttccgatctn nnnncgaca gtttacagtc aaggggtaga    60
gc                                                                  62

<210> SEQ ID NO 818
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 818
tggagttcag acgtgtgctc ttccgatctn nnnngctgc cggataccgc gtatagagtg    60
g                                                                   61

<210> SEQ ID NO 819
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 819
tggagttcag acgtgtgctc ttccgatctn nnnntgcgc ccttccccaa tatttttct    60 gcc                                                                 63

<210> SEQ ID NO 820
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 820
tggagttcag acgtgtgctc ttccgatctn nnnngtacc agctagcttt tcagtccaca    60
gc                                                                  62

<210> SEQ ID NO 821
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
```

-continued

<223> OTHER INFORMATION: n is a, c, g, or t

<400> SEQUENCE: 821
tggagttcag acgtgtgctc ttccgatctn nnnnngtacc ccgaaacttg gtcgtcgtag        60
g                                                                                                             61

<210> SEQ ID NO 822
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 822
tggagttcag acgtgtgctc ttccgatctn nnnnnacgta tcagcttcac tggtaccaac        60
tc                                                                                                            62

<210> SEQ ID NO 823
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 823
tggagttcag acgtgtgctc ttccgatctn nnnnntgatt ctatggtggg gagcgatccg        60

<210> SEQ ID NO 824
<211> LENGTH: 59
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 824
tggagttcag acgtgtgctc ttccgatctn nnnntgcgg cgagcagcgg tagggtgcg          59

<210> SEQ ID NO 825
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 825
tggagttcag acgtgtgctc ttccgatctn nnnnntagag tgctttctag agctggatgc        60
g                                                                                                             61

<210> SEQ ID NO 826
<211> LENGTH: 62

-continued

```
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 826
tggagttcag acgtgtgctc ttccgatctn nnnnntgatg gatagctctg gagatgacat      60
gg                                                                    62

<210> SEQ ID NO 827
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 827
tggagttcag acgtgtgctc ttccgatctn nnnnntatga gcgaggtact taccacgtaa      60
tc                                                                    62

<210> SEQ ID NO 828
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 828
tggagttcag acgtgtgctc ttccgatctn nnnnacgta cgctgctgga tggaaagatg       60
g                                                                     61

<210> SEQ ID NO 829
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 829
tggagttcag acgtgtgctc ttccgatctn nnnngctgt gggaacagtg gagtaacaaa       60
atg                                                                   63

<210> SEQ ID NO 830
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
```

-continued

```
<223> OTHER INFORMATION: n is a, c, g, or t

<400> SEQUENCE: 830
tggagttcag acgtgtgctc ttccgatctn nnnnngcgct gtcagaaccc agatttactc      60
aag                                                                     63

<210> SEQ ID NO 831
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 831
tggagttcag acgtgtgctc ttccgatctn nnnnncgacc agctgaagtt tgtttgagga      60
tag                                                                     63

<210> SEQ ID NO 832
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 832
tggagttcag acgtgtgctc ttccgatctn nnnnnacgta gctgctctct tcagtttcag      60
tc                                                                      62

<210> SEQ ID NO 833
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 833
tggagttcag acgtgtgctc ttccgatctn nnnnnacgtg aaaatcttgc aaaacgttgg      60
actc                                                                    64

<210> SEQ ID NO 834
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 834
tggagttcag acgtgtgctc ttccgatctn nnnnntgcgc ggtatccttt ctgtcactgc      60
c                                                                       61
```

<210> SEQ ID NO 835
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 835
tggagttcag acgtgtgctc ttccgatctn nnnnntatgc tcatcaagat ctttcacagc      60
cag                                                                    63

<210> SEQ ID NO 836
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 836
tggagttcag acgtgtgctc ttccgatctn nnnnntgtaa ttggatgggt aagctgctgg      60
g                                                                      61

<210> SEQ ID NO 837
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 837
tggagttcag acgtgtgctc ttccgatctn nnnnntatgt aactttggac gataatcaag      60
agac                                                                   64

<210> SEQ ID NO 838
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 838
tggagttcag acgtgtgctc ttccgatctn nnnntagac caatcgagca tcccttgcgc       60

<210> SEQ ID NO 839
<211> LENGTH: 62
<212> TYPE: DNA
<213> ORGANISM: artificial sequence
<220> FEATURE:
<223> OTHER INFORMATION: allele 2 probe
<220> FEATURE:

-continued

<220> NAME/KEY: misc_feature
<222> LOCATION: (30)..(35)
<223> OTHER INFORMATION: n is a, c, g, or t

<400> SEQUENCE: 839
tggagttcag acgtgtgctc ttccgatctn nnnnntgcgg gtagcagagg ttccacatga    60
ag                                                                    62

<210> SEQ ID NO 840
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 840
tggagttcag acgtgtgctc ttccgatctn nnnnngctgt ctaccacatc acaggaccga    60
g                                                                     61

<210> SEQ ID NO 841
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 841
tggagttcag acgtgtgctc ttccgatctn nnnnngtacg ttcgtcatgg ttgacctaga    60
tg                                                                    62

<210> SEQ ID NO 842
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 842
tggagttcag acgtgtgctc ttccgatctn nnnnnacgtg caagagacaa ctccatgagc    60
c                                                                     61

<210> SEQ ID NO 843
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 843
tggagttcag acgtgtgctc ttccgatctn nnnnnagaga ggccggattt caaaagttta    60

-continued

```
gtc                                                            63

<210> SEQ ID NO 844
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 844
tggagttcag acgtgtgctc ttccgatctn nnnnnagagt ctcagcacgg aaagttctac    60
ac                                                            62

<210> SEQ ID NO 845
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 845
tggagttcag acgtgtgctc ttccgatctn nnnnngtacc tctgatttct tccggtttca    60
atag                                                          64

<210> SEQ ID NO 846
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 846
tggagttcag acgtgtgctc ttccgatctn nnnnngcgcc tgatgtactg atacctttt     60 ccg                                                           63

<210> SEQ ID NO 847
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 847
tggagttcag acgtgtgctc ttccgatctn nnnntctct tgtgctgaaa acgtgaattc     60
tgc                                                           63

<210> SEQ ID NO 848
<211> LENGTH: 60
<212> TYPE: DNA
```

<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 848
tggagttcag acgtgtgctc ttccgatctn nnnnngtctg gcccaatccc ggcgtctatc      60

<210> SEQ ID NO 849
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 849
tggagttcag acgtgtgctc ttccgatctn nnnntctcg gagtgttgtt tccattggta      60
ctg                                                                    63

<210> SEQ ID NO 850
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 850
tggagttcag acgtgtgctc ttccgatctn nnnnntatga cctgctggat ctgctgaaga      60
g                                                                      61

<210> SEQ ID NO 851
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 851
tggagttcag acgtgtgctc ttccgatctn nnnnntgatg ttgttacatc tcgtttctct      60
ttcc                                                                   64

<210> SEQ ID NO 852
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 852

-continued

```
tggagttcag acgtgtgctc ttccgatctn nnnnntcagt atccatgtct ccaggtgaag      60
tg                                                                       62

<210> SEQ ID NO 853
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 853
tggagttcag acgtgtgctc ttccgatctn nnnncagcg ttcaatgctt tacctcctct       60
gg                                                                       62

<210> SEQ ID NO 854
<211> LENGTH: 59
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 854
tggagttcag acgtgtgctc ttccgatctn nnnntctct ccagggcatc agcgcctcc        59

<210> SEQ ID NO 855
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 855
tggagttcag acgtgtgctc ttccgatctn nnnnacgtg caaggtgaag cttcactgaa       60
ac                                                                       62

<210> SEQ ID NO 856
<211> LENGTH: 59
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 856
tggagttcag acgtgtgctc ttccgatctn nnnntgcga cgccagacga cgcgtctcc        59

<210> SEQ ID NO 857
<211> LENGTH: 64
<212> TYPE: DNA
<213> ORGANISM: artificial sequence
<220> FEATURE:
```

<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 857
tggagttcag acgtgtgctc ttccgatctn nnnnntctca aaacaccacc accatttcat        60
tttg                                                                     64

<210> SEQ ID NO 858
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 858
tggagttcag acgtgtgctc ttccgatctn nnnnntgata tggggaatct ctgcatgtaa        60
cat                                                                      63

<210> SEQ ID NO 859
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 859
tggagttcag acgtgtgctc ttccgatctn nnnntctcg cagagccagc taaaagatca         60
ac                                                                       62

<210> SEQ ID NO 860
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 860
tggagttcag acgtgtgctc ttccgatctn nnnnacgtc tttagctgca caactgctat         60
gg                                                                       62

<210> SEQ ID NO 861
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 861
tggagttcag acgtgtgctc ttccgatctn nnnnntgcgg gtaagctctt gttttgttgc      60
tcc                                                                    63

<210> SEQ ID NO 862
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 862
tggagttcag acgtgtgctc ttccgatctn nnnnngtctg atgagatgca tacaaaattg      60
ccg                                                                    63

<210> SEQ ID NO 863
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 863
tggagttcag acgtgtgctc ttccgatctn nnnnntctcc caggattgtt gttctgcttt      60
cg                                                                     62

<210> SEQ ID NO 864
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 864
tggagttcag acgtgtgctc ttccgatctn nnnnntcaga gcctgattga caatgttgtc      60
cc                                                                     62

<210> SEQ ID NO 865
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 865
tggagttcag acgtgtgctc ttccgatctn nnnncgacg ggcactgatc taacaacctg      60
ac                                                                     62

<210> SEQ ID NO 866

-continued

```
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 866
tggagttcag acgtgtgctc ttccgatctn nnnnncagcc gctgctcgtg tctgaattct      60
c                                                                       61

<210> SEQ ID NO 867
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 867
tggagttcag acgtgtgctc ttccgatctn nnnnngcgcc acgatgaagg cagcttcttc      60
ac                                                                      62

<210> SEQ ID NO 868
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 868
tggagttcag acgtgtgctc ttccgatctn nnnnngctgt ctcataattt caaaatcgga      60
tgcg                                                                    64

<210> SEQ ID NO 869
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 869
tggagttcag acgtgtgctc ttccgatctn nnnnngcgca ttaaggatgt ctatcgaccg      60
gg                                                                      62

<210> SEQ ID NO 870
<211> LENGTH: 65
<212> TYPE: DNA
<213> ORGANISM: artificial sequence
<220> FEATURE:
<223> OTHER INFORMATION: allele 2 probe
<220> FEATURE:
<221> NAME/KEY: misc_feature
```

-continued

```
<222> LOCATION: (30)..(35)
<223> OTHER INFORMATION: n is a, c, g, or t

<400> SEQUENCE: 870
tggagttcag acgtgtgctc ttccgatctn nnnnntctca gtacaacaag agaaaaagag      60
aaatg                                                                  65

<210> SEQ ID NO 871
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 871
tggagttcag acgtgtgctc ttccgatctn nnnnntagag tatacattgt cttggggctt      60
atc                                                                    63

<210> SEQ ID NO 872
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 872
tggagttcag acgtgtgctc ttccgatctn nnnnngtacc ctgcatcttt gtcctatcct      60
atg                                                                    63

<210> SEQ ID NO 873
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 873
tggagttcag acgtgtgctc ttccgatctn nnnnntagag ctgctggaat ataattggggg     60 gc                                                                     62

<210> SEQ ID NO 874
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 874
tggagttcag acgtgtgctc ttccgatctn nnnnngctgg aagacccgga ccggaaggag      60
```

-continued

```
<210> SEQ ID NO 875
<211> LENGTH: 66
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 875
tggagttcag acgtgtgctc ttccgatctn nnnnngctgc tctgatactt tctttcaaaa    60
cataag                                                              66

<210> SEQ ID NO 876
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 876
tggagttcag acgtgtgctc ttccgatctn nnnnagagc gccataaaag ttatgccacc     60
ac                                                                  62

<210> SEQ ID NO 877
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 877
tggagttcag acgtgtgctc ttccgatctn nnnntgcgg cgagaaacca caagttaaac     60
gg                                                                  62

<210> SEQ ID NO 878
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 878
tggagttcag acgtgtgctc ttccgatctn nnnntctcg tcagaaccaa tgccgtagta     60
ac                                                                  62

<210> SEQ ID NO 879
<211> LENGTH: 62
<212> TYPE: DNA
<213> ORGANISM: artificial sequence
<220> FEATURE:
<223> OTHER INFORMATION: allele 2 probe
```

-continued

```
<220> FEATURE:
<221> NAME/KEY: misc_feature
<222> LOCATION: (30)..(35)
<223> OTHER INFORMATION: n is a, c, g, or t

<400> SEQUENCE: 879
tggagttcag acgtgtgctc ttccgatctn nnnnntatgt ctgctgctgt tgatagtgct     60
ag                                                                    62

<210> SEQ ID NO 880
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 880
tggagttcag acgtgtgctc ttccgatctn nnnnntctca gatcagacca atgttatcaa     60
actg                                                                  64

<210> SEQ ID NO 881
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 881
tggagttcag acgtgtgctc ttccgatctn nnnncgacg attaattaat ggcccctcct     60
cc                                                                    62

<210> SEQ ID NO 882
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 882
tggagttcag acgtgtgctc ttccgatctn nnnntagaa ctttgaacca ttggatggag     60
atg                                                                   63

<210> SEQ ID NO 883
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 883
```

-continued

```
tggagttcag acgtgtgctc ttccgatctn nnnnntatgc ttaacaccgt aaagtagaga        60
taac                                                                     64

<210> SEQ ID NO 884
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 884
tggagttcag acgtgtgctc ttccgatctn nnnnntagac atcaaatgtg aagtcgtcac        60
cac                                                                      63

<210> SEQ ID NO 885
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 885
tggagttcag acgtgtgctc ttccgatctn nnnncagcc tacgagtaca tgcatataca        60
gtac                                                                     64

<210> SEQ ID NO 886
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 886
tggagttcag acgtgtgctc ttccgatctn nnnnntcaga tattccttga tgggcttctg        60
gg                                                                       62

<210> SEQ ID NO 887
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 887
tggagttcag acgtgtgctc ttccgatctn nnnngcgcg cagccatctc taccgacacc        60

<210> SEQ ID NO 888
<211> LENGTH: 65
<212> TYPE: DNA
<213> ORGANISM: artificial sequence
```

-continued

```
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 888
tggagttcag acgtgtgctc ttccgatctn nnnnncagcc tttgtttttg gccgtgaaat      60
aaaat                                                                  65

<210> SEQ ID NO 889
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 889
tggagttcag acgtgtgctc ttccgatctn nnnncgacc ggttagtacg ccatagcgaa       60
c                                                                      61

<210> SEQ ID NO 890
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 890
tggagttcag acgtgtgctc ttccgatctn nnnntgcgc tgtgctgcgc atttctttgt       60
tc                                                                     62

<210> SEQ ID NO 891
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 891
tggagttcag acgtgtgctc ttccgatctn nnnntcagc ttctgaaatc gaagtgcgag       60
ag                                                                     62

<210> SEQ ID NO 892
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t
```

-continued

```
<400> SEQUENCE: 892
tggagttcag acgtgtgctc ttccgatctn nnnnnacgtg ccgagccgat caagatagtg     60
g                                                                    61

<210> SEQ ID NO 893
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 893
tggagttcag acgtgtgctc ttccgatctn nnnnntagag tcggtagatc acaagcatga     60
tag                                                                  63

<210> SEQ ID NO 894
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 894
tggagttcag acgtgtgctc ttccgatctn nnnnntgtaa gaatgtcttc caaactgcct     60
gg                                                                   62

<210> SEQ ID NO 895
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 895
tggagttcag acgtgtgctc ttccgatctn nnnnagagc aaggtttttt tgtgaaagga     60
gtgg                                                                 64

<210> SEQ ID NO 896
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 896
tggagttcag acgtgtgctc ttccgatctn nnnngtctt tgagggaaat gatctagaat     60
ggc                                                                  63
```

```
<210> SEQ ID NO 897
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 897
tggagttcag acgtgtgctc ttccgatctn nnnnngtacc taatttcagc agcaaactgg      60
cc                                                                     62

<210> SEQ ID NO 898
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 898
tggagttcag acgtgtgctc ttccgatctn nnnntctcc gtcgtcgttc tgacatgctt       60
c                                                                      61

<210> SEQ ID NO 899
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 899
tggagttcag acgtgtgctc ttccgatctn nnnntatgc tttagaaatc cgggtcatct       60
ttc                                                                    63

<210> SEQ ID NO 900
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 900
tggagttcag acgtgtgctc ttccgatctn nnnntgtac gattgcttac actgttgcag       60
cc                                                                     62

<210> SEQ ID NO 901
<211> LENGTH: 62
<212> TYPE: DNA
<213> ORGANISM: artificial sequence
<220> FEATURE:
<223> OTHER INFORMATION: allele 2 probe
<220> FEATURE:
```

<221> NAME/KEY: misc_feature
<222> LOCATION: (30)..(35)
<223> OTHER INFORMATION: n is a, c, g, or t

<400> SEQUENCE: 901
tggagttcag acgtgtgctc ttccgatctn nnnntctca gcatatagaa gaggggaagg      60
ag                                                                    62

<210> SEQ ID NO 902
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 902
tggagttcag acgtgtgctc ttccgatctn nnnngcgcg agatggttgg tgagagtcat      60
ag                                                                    62

<210> SEQ ID NO 903
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 903
tggagttcag acgtgtgctc ttccgatctn nnnncagcg ataagcatgt gcagcaactt      60
gc                                                                    62

<210> SEQ ID NO 904
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 904
tggagttcag acgtgtgctc ttccgatctn nnnntagac tggacgtagt cgttgtcaac      60
g                                                                     61

<210> SEQ ID NO 905
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 905
tggagttcag acgtgtgctc ttccgatctn nnnngctgc atagagcggg aaaaaaagtg      60

```
gg                                                                          62

<210> SEQ ID NO 906
<211> LENGTH: 65
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 906
tggagttcag acgtgtgctc ttccgatctn nnnnntgatg ttgtaagtgc acaaaaataa      60
agcag                                                                       65

<210> SEQ ID NO 907
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 907
tggagttcag acgtgtgctc ttccgatctn nnnnntgcgc caaattcaag ctgcaagtta      60
tcc                                                                         63

<210> SEQ ID NO 908
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 908
tggagttcag acgtgtgctc ttccgatctn nnnnacgtc acatccgagt gaagagtaaa       60
cag                                                                         63

<210> SEQ ID NO 909
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 909
tggagttcag acgtgtgctc ttccgatctn nnnnntatgg taatccacaa agttaccagc      60
gc                                                                          62

<210> SEQ ID NO 910
<211> LENGTH: 62
<212> TYPE: DNA
```

<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 910
tggagttcag acgtgtgctc ttccgatctn nnnnntgtat agcatgcctc tgttatctgc      60
ag                                                                     62

<210> SEQ ID NO 911
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 911
tggagttcag acgtgtgctc ttccgatctn nnnnnagaga atgtccaaat cccgccggaa      60
c                                                                      61

<210> SEQ ID NO 912
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 912
tggagttcag acgtgtgctc ttccgatctn nnnnntagag ctggtagcag ccatgcatct      60
g                                                                      61

<210> SEQ ID NO 913
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 913
tggagttcag acgtgtgctc ttccgatctn nnnnnagagg gtatgaccaa actaagtcga      60
cg                                                                     62

<210> SEQ ID NO 914
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t -continued

<400> SEQUENCE: 914
tggagttcag acgtgtgctc ttccgatctn nnnnntgtag aaagcaccac aatcaggtca      60
aac                                                                                                      63

<210> SEQ ID NO 915
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 915
tggagttcag acgtgtgctc ttccgatctn nnnnntagat gtgaactgaa gtagtttctt      60
tgtc                                                                                                     64

<210> SEQ ID NO 916
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 916
tggagttcag acgtgtgctc ttccgatctn nnnnngtctt gaaaatgagg cagcactttc      60
atc                                                                                                      63

<210> SEQ ID NO 917
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 917
tggagttcag acgtgtgctc ttccgatctn nnnnntatgt cgtaaaagct atggctgcag      60
ag                                                                                                       62

<210> SEQ ID NO 918
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 918
tggagttcag acgtgtgctc ttccgatctn nnnnngctgt atggacggtg ctcacaaaat      60
gg                                                                                                       62

<210> SEQ ID NO 919
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 919
tggagttcag acgtgtgctc ttccgatctn nnnnngtctg ccggcaagct gagtaatttg      60
g                                                                     61

<210> SEQ ID NO 920
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 920
tggagttcag acgtgtgctc ttccgatctn nnnnntatgc agtacagtct caagcaatcg      60
atc                                                                   63

<210> SEQ ID NO 921
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 921
tggagttcag acgtgtgctc ttccgatctn nnnnntgtac ttaaacatcc tagatcggct      60
ctg                                                                   63

<210> SEQ ID NO 922
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 922
tggagttcag acgtgtgctc ttccgatctn nnnnnagagg ttagttgtct tgcgctcatg      60
cc                                                                    62

<210> SEQ ID NO 923
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 923
tggagttcag acgtgtgctc ttccgatctn nnnnnacgtg tctaggcctc ctaagcttac      60
c                                                                     61

<210> SEQ ID NO 924
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 924
tggagttcag acgtgtgctc ttccgatctn nnnnntgata gcaagctcta ttacatcaaa      60
gaac                                                                  64

<210> SEQ ID NO 925
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 925
tggagttcag acgtgtgctc ttccgatctn nnnntgcgg acagcatgca gcatcgttgc       60
g                                                                     61

<210> SEQ ID NO 926
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 926
tggagttcag acgtgtgctc ttccgatctn nnnncagcc accccttag atgctctatg        60 c                                                                     61

<210> SEQ ID NO 927
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 927
tggagttcag acgtgtgctc ttccgatctn nnnnntgtac tgtagagggc agcaagtttc      60
at                                                                    62

<210> SEQ ID NO 928
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 928
tggagttcag acgtgtgctc ttccgatctn nnnnncagcg acaaaagaaa aaggacacat      60
gaag                                                                  64

<210> SEQ ID NO 929
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 929
tggagttcag acgtgtgctc ttccgatctn nnnnntctcc gtattagtac agtatttcag      60
agtg                                                                  64

<210> SEQ ID NO 930
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 930
tggagttcag acgtgtgctc ttccgatctn nnnnntgtag cttgggctgc atcgcctgag      60

<210> SEQ ID NO 931
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 931
tggagttcag acgtgtgctc ttccgatctn nnnnngtacg attttcagct ttgcactaac      60
tgac                                                                  64

<210> SEQ ID NO 932
<211> LENGTH: 65
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 932
tggagttcag acgtgtgctc ttccgatctn nnnnncagcc aaagttgata tcttttccaa      60
tcttc                                                                  65

<210> SEQ ID NO 933
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 933
tggagttcag acgtgtgctc ttccgatctn nnnntctcc ctgatgaagg caaaagggaa      60
aag                                                                    63

<210> SEQ ID NO 934
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 934
tggagttcag acgtgtgctc ttccgatctn nnnnnacgtg caaacccgga tcagtaacaa      60
tc                                                                     62

<210> SEQ ID NO 935
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 935
tggagttcag acgtgtgctc ttccgatctn nnnncgact gattgcagtt ggtttcattt      60
tgac                                                                   64

<210> SEQ ID NO 936
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t -continued

<400> SEQUENCE: 936

```
tggagttcag acgtgtgctc ttccgatctn nnnnngctgc gcaatacagc ggtcacaaca      60
c                                                                        61
```

<210> SEQ ID NO 937
<211> LENGTH: 66
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 937

```
tggagttcag acgtgtgctc ttccgatctn nnnnngcgcc aataagatta gcataaaata      60
gtcgtg                                                                   66
```

<210> SEQ ID NO 938
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 938

```
tggagttcag acgtgtgctc ttccgatctn nnnnntgtat tttcaccaaa attaagcagg      60
actg                                                                     64
```

<210> SEQ ID NO 939
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 939

```
tggagttcag acgtgtgctc ttccgatctn nnnnngtacg gtggttattc gggcttttgc      60
g                                                                        61
```

<210> SEQ ID NO 940
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 940

```
tggagttcag acgtgtgctc ttccgatctn nnnntgcga gtggcattca gatcaacagt      60
cc                                                                       62
```

-continued

```
<210> SEQ ID NO 941
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 941
tggagttcag acgtgtgctc ttccgatctn nnnnngcgcg agagagagag agagagagat      60
cg                                                                    62

<210> SEQ ID NO 942
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 942
tggagttcag acgtgtgctc ttccgatctn nnnnntcagg ccagtaactc tttcctccct      60
ac                                                                    62

<210> SEQ ID NO 943
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 943
tggagttcag acgtgtgctc ttccgatctn nnnnngctgc aaaggagcta gatcttcttc      60
gg                                                                    62

<210> SEQ ID NO 944
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 944
tggagttcag acgtgtgctc ttccgatctn nnnnngcgcg ttgaactctt tgaacacatc      60
attg                                                                  64

<210> SEQ ID NO 945
<211> LENGTH: 63
<212> TYPE: DNA
<213> ORGANISM: artificial sequence
<220> FEATURE:
<223> OTHER INFORMATION: allele 2 probe
<220> FEATURE:
```

```
<221> NAME/KEY: misc_feature
<222> LOCATION: (30)..(35)
<223> OTHER INFORMATION: n is a, c, g, or t

<400> SEQUENCE: 945
tggagttcag acgtgtgctc ttccgatctn nnnnntctcg aagaacacaa ggcagattga      60
tgc                                                                    63

<210> SEQ ID NO 946
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 946
tggagttcag acgtgtgctc ttccgatctn nnnnntcagg caagtttgta tacttcaggg      60
gtg                                                                    63

<210> SEQ ID NO 947
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 947
tggagttcag acgtgtgctc ttccgatctn nnnnnacgtg acgtccggct gctactactc      60

<210> SEQ ID NO 948
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 948
tggagttcag acgtgtgctc ttccgatctn nnnnngtctg actgtagttt tgtgcatctt      60
gaac                                                                   64

<210> SEQ ID NO 949
<211> LENGTH: 66
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 949
tggagttcag acgtgtgctc ttccgatctn nnnnntgatc agttgagttc gtttatttat      60
ttatag                                                                 66
```

<210> SEQ ID NO 950
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 950
tggagttcag acgtgtgctc ttccgatctn nnnnntatga attggtaggg aaggggttcc      60
g                                                                     61

<210> SEQ ID NO 951
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 951
tggagttcag acgtgtgctc ttccgatctn nnnnngtctc cagcaccatg aaggttcatc      60
c                                                                     61

<210> SEQ ID NO 952
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 952
tggagttcag acgtgtgctc ttccgatctn nnnnntagag aagcatggcc ggttatatac      60
tc                                                                    62

<210> SEQ ID NO 953
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 953
tggagttcag acgtgtgctc ttccgatctn nnnnntatgt ccacagtaat gtaaccactg      60
cc                                                                    62

<210> SEQ ID NO 954
<211> LENGTH: 63
<212> TYPE: DNA
<213> ORGANISM: artificial sequence
<220> FEATURE:

-continued

```
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 954
tggagttcag acgtgtgctc ttccgatctn nnnngtctc ttcttgtcaa aaatgaggcc      60
agg                                                                    63

<210> SEQ ID NO 955
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 955
tggagttcag acgtgtgctc ttccgatctn nnnntagac gaaaataacc aaactgcact      60
tctg                                                                   64

<210> SEQ ID NO 956
<211> LENGTH: 65
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 956
tggagttcag acgtgtgctc ttccgatctn nnnntagaa gaaaaattta ggcagcacaa      60
aaatg                                                                  65

<210> SEQ ID NO 957
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 957
tggagttcag acgtgtgctc ttccgatctn nnnntatgg ttggaaaatc ggtgtaccat      60
atg                                                                    63

<210> SEQ ID NO 958
<211> LENGTH: 66
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 958
```

```
tggagttcag acgtgtgctc ttccgatctn nnnnntgcgg gtttggttcg ttatattata      60
tatagc                                                                  66

<210> SEQ ID NO 959
<211> LENGTH: 60
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 959
tggagttcag acgtgtgctc ttccgatctn nnnnntagag gcagccatgt cagctacagc      60

<210> SEQ ID NO 960
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 960
tggagttcag acgtgtgctc ttccgatctn nnnnntgcgc cagctctaca ccaaggaatc      60
g                                                                       61

<210> SEQ ID NO 961
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 961
tggagttcag acgtgtgctc ttccgatctn nnnngcgca acctttgaag agaacgtgca       60
tac                                                                     63

<210> SEQ ID NO 962
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 962
tggagttcag acgtgtgctc ttccgatctn nnnnntagag gcaaggatta tctaagctgc      60
tac                                                                     63

<210> SEQ ID NO 963
<211> LENGTH: 61
<212> TYPE: DNA
```

```
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 963
tggagttcag acgtgtgctc ttccgatctn nnnngcgcg accagactac cagagacaga      60
c                                                                     61

<210> SEQ ID NO 964
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 964
tggagttcag acgtgtgctc ttccgatctn nnnntgtat gagttctgtt tattttggct      60
gcg                                                                   63

<210> SEQ ID NO 965
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 965
tggagttcag acgtgtgctc ttccgatctn nnnnagagc gactacgatg cccccattga      60
c                                                                     61

<210> SEQ ID NO 966
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 966
tggagttcag acgtgtgctc ttccgatctn nnnngtacc atgaaacgac aacacattca      60
catc                                                                  64

<210> SEQ ID NO 967
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t
```

<400> SEQUENCE: 967
tggagttcag acgtgtgctc ttccgatctn nnnnntagag caattgtgtt tggaggcata      60
cag                                                                    63

<210> SEQ ID NO 968
<211> LENGTH: 65
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 968
tggagttcag acgtgtgctc ttccgatctn nnnnngctgg aatgaagatg tgattatgct      60
attac                                                                  65

<210> SEQ ID NO 969
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 969
tggagttcag acgtgtgctc ttccgatctn nnnnntgtag ccatttttca catccagtga      60
tcg                                                                    63

<210> SEQ ID NO 970
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 970
tggagttcag acgtgtgctc ttccgatctn nnnnngtctg cgtaatgagt ccttgcagta      60
cc                                                                     62

<210> SEQ ID NO 971
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 971
tggagttcag acgtgtgctc ttccgatctn nnnnnacgta caaatgggtt atgcagaagt      60
agc                                                                    63

-continued

```
<210> SEQ ID NO 972
<211> LENGTH: 64
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 972
tggagttcag acgtgtgctc ttccgatctn nnnnntagat atatacgcat ttgatgtgca      60
tgtc                                                                   64

<210> SEQ ID NO 973
<211> LENGTH: 59
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 973
tggagttcag acgtgtgctc ttccgatctn nnnnntgatc cgggcttccc accaaacgc       59

<210> SEQ ID NO 974
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 974
tggagttcag acgtgtgctc ttccgatctn nnnnngcgct tttaggaagg ccagagtaca      60
cg                                                                     62

<210> SEQ ID NO 975
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 975
tggagttcag acgtgtgctc ttccgatctn nnnnntgtac attgtttcca catcctcctt      60
agg                                                                    63

<210> SEQ ID NO 976
<211> LENGTH: 63
<212> TYPE: DNA
<213> ORGANISM: artificial sequence
<220> FEATURE:
<223> OTHER INFORMATION: allele 2 probe
<220> FEATURE:
<221> NAME/KEY: misc_feature
```

-continued

```
<222> LOCATION: (30)..(35)
<223> OTHER INFORMATION: n is a, c, g, or t

<400> SEQUENCE: 976
tggagttcag acgtgtgctc ttccgatctn nnnnntgcgc ccacacactc tcttgtcaat        60
atc                                                                       63

<210> SEQ ID NO 977
<211> LENGTH: 62
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 977
tggagttcag acgtgtgctc ttccgatctn nnnnnagagc aggttcttgg atgtttatgg        60
cc                                                                        62

<210> SEQ ID NO 978
<211> LENGTH: 61
<212> TYPE: DNA
<213> ORGANISM: artificial sequence
<220> FEATURE:
<223> OTHER INFORMATION: allele 2 probe
<220> FEATURE:
<221> NAME/KEY: misc_feature
<222> LOCATION: (30)..(35)
<223> OTHER INFORMATION: n is a, c, g, or t

<400> SEQUENCE: 978
tggagttcag acgtgtgctc ttccgatctn nnnnngtcta gcaccgtgtc cctgtatgta        60
g                                                                         61
```

GENOTYPING OF POLYPLOIDS

CROSS-REFERENCE TO RELATED APPLICATIONS

The present application is a Continuation of International Patent Application No. PCT/EP2020/054676, filed Feb. 21, 2020, which claims priority to Europe patent application Ser. No. 19/158,598.3 filed Feb. 21, 2019; the entire contents of all of which are hereby incorporated by reference.

SEQUENCE LISTING

The instant application contains a Sequence Listing which has been submitted electronically in ASCII format and is hereby incorporated by reference in its entirety. Said ASCII copy, created on Aug. 10, 2021, is named P6080424PCTSequencelisting.txt and is 299,000 bytes in size.

FIELD OF THE INVENTION

The present invention is in the field of molecular biology, more in particular in the field of genomics. The invention is further in the field of polyploid organisms and concerns their genomic analysis.

BACKGROUND ART

The analysis of genomic variation is considered an essential part of plant genetics and crop improvement programs. DNA polymorphisms can be directly related to phenotype differences, be genetically linked to their causative factors, or indicate relationships between individuals in populations. Over the last 30 years, the use of genotyping has enabled the characterization and mapping of genes and metabolic pathways in plants as well as the study of species diversity and evolution, marker-assisted selection (MAS), germplasm characterization and seed purity. Single Nucleotide Polymorphisms (SNPs) have emerged as the most widely used genotyping markers due to their abundance in the genome and the relative ease in determining their frequency in a cost-effective and parallel manner in a given panel of individuals (Deschamps S. et al, *Genotyping-by-Sequencing in Plants*, Biology (Basel) (2012); 1 (3): 460-483).

There are many different approaches for genotyping variants in DNA, based on a variety of allele-discrimination chemistries including primer extension assays, and ligation-based methods preferably using allele-specific probes and a wide range of detection platforms including capillary electrophoresis systems for fragment detection, microtiter plates for fluorescence signal detection, microarrays/DNA chips for probe hybridization and next-generation sequencing (NGS) instruments. Most genotyping methods are designed for the analysis of two alleles per locus, which may be exemplified as A and B. In the case of a diploid organism, the alleles carried on a pair of homologous chromosomes define three possible genotypes; AA, AB or BB. These genotypes can be determined in a straightforward manner using a qualitative assay capable of detecting the presence or absence of the respective A and B alleles.

However, the situation becomes more complicated in the case of polyploid organisms. Polyploidy is characterized as the state of a cell or organism having more than two paired (homologous) sets of chromosomes. For example, in tetraploid organisms, five distinct genotypes are possible for every bi-allelic polymorphism; AAAA, AAAB, AABB, ABBB, BBBB, and the number of genotypic classes is even larger for organisms with higher ploidy levels (such as hexaploid or octaploid organisms). It follows logically that accurate determination of the genotypes of samples from polyploid organisms requires a quantitative assessment of the presence of the respective alleles. This especially may be cumbersome when the genotyping assay involves an amplification step, e.g. PCR, as the alleles may amplify unevenly. This means that the ratio between the alleles after amplification may not accurately represent the ratio before amplification, which can result in an incorrect genotype assignment. Also, there may be additional reasons why detection methods may not be sensitive enough to accurately determine the ratio between alleles in a polyploid organism.

Polyploidy is especially common in plants. Due to this polyploidy, genotyping variants in plants is still challenging. There is therefore a strong need in the art to accurately genotype polyploid samples, such as polyploid plant samples.

SUMMARY OF THE INVENTION

The invention is summarized in the following numbered embodiments:

Embodiment 1. A method for determining the relative frequency of a sequence variant of interest in a nucleic acid sample derived from a at least one polyploid cell, wherein the method comprises the steps of:
- a) providing polynucleotides derived from said nucleic acid sample, wherein each polynucleotide comprises a unique molecular index (UMI),
- b) amplifying the polynucleotides provided in step a);
- c) determining the sequences of the amplified polynucleotides to obtain sequence reads;
- d) obtaining a consensus sequence of the sequence reads that are derived from a single polynucleotide of step a) using at least the UMI; and
- e) determining the relative frequency of the sequence variant of interest based on the frequency of consensus sequences comprising the sequence variant of interest and the frequency of a reference sequence.

Embodiment 2. The method according to embodiment 1, wherein the polynucleotides of step a) are at least one of:
- i) fragments of nucleic acids from the sample, wherein each fragment is attached to a UMI; and
- ii) ligation products of probes capable of hybridizing to the sequence variant of interest in a nucleic acid from the sample, wherein each ligation product comprise a UMI.

Embodiment 3. The method according to embodiment 1, wherein step d) comprises collapsing sequence reads obtained in step c).

Embodiment 4. The method according to any one of the preceding embodiments, wherein the reference sequence in step e) is derived from the same nucleic acid sample comprising the sequence variant of interest, wherein preferably the reference sequence is a variant of the sequence variant of interest, and/or wherein preferably the relative frequency of the sequence variant of interest is determined based on the frequency of consensus sequences comprising the sequence variant of interest and the frequency of consensus sequences comprising the reference sequence.

Embodiment 5. The method according to any one of the preceding embodiments, wherein the sequence variant of interest is, or is part of, an allele, wherein preferably the allele is present on a single locus, and wherein the determined relative frequency is used to obtain the genotype of the nucleic acid sample.

Embodiment 6. The method according to any one of the preceding embodiments, wherein the method is preceded by a step of determining the ploidy level of the at least one polyploid cell.

Embodiment 7. The method according to any one of the preceding embodiments, wherein the relative frequency of two or more sequences of interest is determined.

Embodiment 8. The method according to any one of the preceding embodiments, wherein the polynucleotides are ligation products of embodiment 2 sub ii) and wherein the UMI is present in an allele-specific oligonucleotide ligation probe.

Embodiment 9. The method according to any one of the preceding embodiments, wherein prior to sequencing in step c) the provided polynucleotides or amplified polynucleotides are enriched, preferably using a hybridization-based capture method.

Embodiment 10. The method according to any one of the preceding embodiments, wherein the polynucleotides and/or amplified polynucleotides comprise a sample identifier.

Embodiment 11. The method according to any one of the preceding claims, wherein the polynucleotides are fragments of claim 2 sub i), wherein at least a first adapter is ligated to the fragments and wherein the UMI is located in the first adapter, wherein optionally a second adapter is ligated to said fragment, and wherein preferably a sample identifier is present in the first or optional second adapter.

Embodiment 12. The method according to any one of embodiments 2-11, wherein the method is multiplexed.

Embodiment 13. Use of a UMI for determining the relative frequency of a sequence variant of interest in a nucleic acid sample derived from at least one polyploid cell, wherein preferably the UMI is comprised in at least one of:
   an oligonucleotide ligation probe, preferably an allele-specific oligonucleotide ligation probe; and
   an adapter Embodiment 14. An allele-specific oligonucleotide probe for use in an oligonucleotide ligation assay, wherein the oligonucleotide probe comprises a UMI.

Embodiment 15. A kit of parts for determining the relative frequency of a sequence variant of interest in a nucleic acid derived from at least one polyploid cell, comprising at least one of
   a vial comprising a mixture of oligonucleotide ligation probes, wherein at least part of the oligonucleotide ligation probes comprise a UMI and wherein preferably the mixture of oligonucleotides is specific for one or more alleles and/or for one or more loci;
   a vial comprising a mixture of adapter molecules, wherein the adapter molecules comprise a UMI and optionally a sample identifier; and
   a vial comprising one or more amplification primers, wherein preferably at least one primer comprises a sample identifier.

Definitions

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Green and Sambrook et al., Molecular Cloning. A Laboratory Manual, $4^{th}$ Edition, Cold Spring Harbor Laboratory Press, Cold Spring Harbor, N. Y., 2012; Ausubel et al. Current Protocols in Molecular Biology, John Wiley & Sons, New York, 1987 and periodic updates; and the series Methods in Enzymology, Academic Press, San Diego.

"A," "an," and "the": these singular form terms include plural referents unless the content clearly dictates otherwise. The indefinite article "a" or "an" thus usually means "at least one". Thus, for example, reference to "a cell" includes a combination of two or more cells, and the like.

"About" and "approximately": these terms, when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods. Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

"And/or": The term "and/or" refers to a situation wherein one or more of the stated cases may occur, alone or in combination with at least one of the stated cases, up to with all of the stated cases.

"Comprising": this term is construed as being inclusive and open ended, and not exclusive. Specifically, the term and variations thereof mean the specified features, steps or components are included. These terms are not to be interpreted to exclude the presence of other features, steps or components.

Exemplary": this terms means "serving as an example, instance, or illustration," and should not be construed as excluding other configurations disclosed herein.

"Plant": Refers to either the whole plant or to parts of a plant, such as cells, tissue cultures or organs (e.g. pollen, seeds, ovules, gametes, roots, leaves, flowers, flower buds, branches, anthers, fruit, kernels, ears, cobs, husks, stalks, root tips, grains, embryos, etc.) obtainable from the plant, as well as derivatives of any of these and progeny derived from such a plant by selfing or crossing. "Plant" further includes plant protoplasts, plant cell tissue cultures from which plants can be regenerated, plant calli, plant clumps, and plant cells that are intact in plants or parts of plants such as embryos, pollen, ovules, gametes, seeds, leaves, flowers, branches, fruit, kernels, ears, cobs, husks, stalks, roots, root tips, anthers, grains and the like. "Plant cell(s)" include protoplasts, gametes, suspension cultures, microspores, pollen grains, etc., either in isolation or within a tissue, organ or organism.

The terms "construct", "nucleic acid construct", "vector", and "expression vector" are used interchangeably herein and is herein defined as a man-made nucleic acid molecule resulting from the use of recombinant DNA technology. These constructs and vectors therefore do not consist of naturally occurring nucleic acid molecules although a vector may comprise (parts of) naturally occurring nucleic acid molecules. A vector can be used to deliver exogenous DNA into a host cell, often with the purpose of expression in the host cell of a DNA region comprised on the construct. The vector backbone of a construct may for example be a plasmid into which a (chimeric) gene is integrated or, if a suitable transcription regulatory sequence is already present (for example a (inducible) promoter), only a desired nucleotide sequence (e.g. a coding sequence, an antisense or an inverted repeat sequence) is integrated downstream of the transcription regulatory sequence. Vectors may comprise further genetic elements to facilitate their use in molecular cloning, such as e.g. selectable markers, multiple cloning sites and the like. The vector backbone may for example be a binary or superbinary vector (see e.g. U.S. Pat. No. 5,591,616, US 2002138879 and WO 95/06722), a co-integrate vector or a T-DNA vector, as known in the art.

Expression vectors are particularly suitable for introducing gene expression in a cell, preferably a plant cell. A preferred expression vector is a naked DNA, a DNA complex or a viral vector, wherein the DNA molecule can be a plasmid. A preferred naked DNA is a linear or circular nucleic acid molecule, e.g. a plasmid. A plasmid refers to a circular double stranded DNA loop into which additional DNA segments can be inserted, such as by standard molecular cloning techniques. A DNA complex can be a DNA molecule coupled to any carrier suitable for delivery of the DNA into the cell. A preferred carrier is selected from the group consisting of a lipoplex, a liposome, a polymersome, a polyplex, a dendrimer, an inorganic nanoparticle, a virosome and cell-penetrating peptides. In a preferred embodiment the expression vector is a viral vector, preferably a Tobacco Rattle Virus (TRV), a Bean yellow dwarf virus (BeYDV), a Cabbage leaf curl virus (CaLCuV), a tobravirus and a Wheat dwarf virus (WDV). Preferably, the viral vector is a Tobacco Rattle Virus as defined herein above The term "gene" means a DNA fragment comprising a region (transcribed region), which is transcribed into an RNA molecule (e.g. a pre-mRNA or ncRNA) in a cell. The transcribed region can be operably linked to suitable regulatory regions (e.g. a promoter), which form part of the gene as defined herein. A gene can comprise several operably linked fragments, such as a 5' leader sequence, a coding region and a 3' non-translated sequence (3' end) comprising a polyadenylation site.

"Expression of a gene" refers to the process wherein a DNA region which is operably linked to appropriate regulatory regions, particularly a promoter, is transcribed into an RNA, and, in case the RNA encodes for a biologically active protein or peptide, subsequently translated into a biologically active protein or peptide.

The term "operably linked" refers to a linkage of polynucleotide elements in a functional relationship. A nucleic acid is "operably linked" when it is placed into a functional relationship with another nucleotide sequence. For instance, a promoter, or rather a transcription regulatory sequence, is operably linked to a coding sequence if it affects the transcription of the coding sequence. Operably linked may mean that the DNA sequences being linked are contiguous.

"Promoter" refers to a nucleic acid fragment that functions to control the transcription of one or more nucleic acids. A promoter fragment is located upstream (5') with respect to the direction of transcription of the transcription initiation site of the gene, and is structurally identified by the presence of a binding site for DNA-dependent RNA polymerase, transcription initiation site(s) and can further comprise any other DNA sequences, including, but not limited to transcription factor binding sites, repressor and activator protein binding sites, and any other sequences of nucleotides known to one of skill in the art to act directly or indirectly to regulate the amount of transcription from the promoter. Optionally the term "promoter" may also include the 5' UTR region (5' Untranslated Region) (e.g. the promoter may herein include one or more parts upstream of the translation initiation codon of transcribed region, as this region may have a role in regulating transcription and/or translation). A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells.

The terms "protein" or "polypeptide" are used interchangeably herein and refer to molecules consisting of a chain of amino acids, without reference to a specific mode of action, size, 3 dimensional structure or origin. A "fragment" or "portion" of a protein may thus still be referred to as a "protein." A protein as defined herein and as used in any method as defined herein may be an isolated protein. An "isolated protein" is used to refer to a protein which is no longer in its natural environment, for example in vitro or in a recombinant bacterial or plant host cell.

"Sequence" or "Nucleotide sequence": This refers to the order of nucleotides of, or within a nucleic acid. In other words, any order of nucleotides in a nucleic acid may be referred to as a sequence or nucleotide sequence.

"Amino acid sequence": This refers to the order of amino acid residues of, or within a protein. In other words, any order of amino acids in a protein may be referred to as amino acid sequence.

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide.

The term "complementarity" is herein defined as the sequence identity of a sequence to a fully complementary strand (e.g. the second, or reverse, strand). For example, a sequence that is 100% complementary (or fully complementary) is herein understood as having 100% sequence identity with the complementary strand and e.g. a sequence that is 80% complementary is herein understood as having 80% sequence identity to the (fully) complementary strand.

"Identity" and "similarity" can be readily calculated by known methods. "Sequence identity" and "sequence similarity" can be determined by alignment of two peptide or two nucleotide sequences using global or local alignment algorithms, depending on the length of the two sequences. Sequences of similar lengths are preferably aligned using a global alignment algorithm (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BEST-FIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blosum62 for proteins and DNAFull for DNA). When sequences have a substantially different overall lengths, local alignments, such as those using the Smith Waterman algorithm, are preferred.

Alternatively percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25 (17): 3389-3402. When utilizing BLAST and Gapped BLAST programs, the default parameters of the respective programs (e.g., BLASTx and BLASTn) can be used. See the homepage of the National Center for Biotechnology Information at ncbi.nlm.nih.gov/.

The term "nucleotide" includes, but is not limited to, naturally-occurring nucleotides, including guanine, cytosine, adenine and thymine (G, C, A and T, respectively). The term "nucleotide" is further intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The terms "nucleic acid" and "nucleic acid molecule" and "polynucleotide" describe a polymer of any length, e.g., greater than about 2 bases, greater than about 10 bases, greater than about 100 bases, greater than about 500 bases, greater than about 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein). The nucleic acid may hybridize with naturally occurring nucleic acids in a sequence specific manner analogous to that of two naturally occurring nucleic acids, e.g., can participate in Watson-Crick base pairing interactions. In addition, nucleic acids may be isolated (and optionally subsequently fragmented) from cells, tissues and/or bodily fluids. The nucleic acid can be e.g. genomic DNA (gDNA), mitochondrial, cell free DNA (cfDNA), and/or DNA from a library.

The term "nucleic acid sample" or "sample comprising a nucleic acid" as used herein denotes any sample containing a nucleic acid, wherein a sample relates to a material or mixture of materials, typically, although not necessarily, in liquid form, containing one or more target nucleotide sequences of interest. The nucleic acid sample used as starting material in the method of the invention can be from any source, e.g., a whole genome, a collection of chromosomes, a single chromosome, or one or more regions from one or more chromosomes, and may be purified directly from the biological source or from a laboratory source, e.g., a nucleic acid library. The nucleic acid samples can be obtained from the same individual, which can be a plant or other species (e.g., animal, human, bacteria, fungi, algae, archaea, etc.), or from different individuals of the same species, or different individuals of different species. For example, the nucleic acid samples may be from a cell, tissue, biopsy, bodily fluid, genome DNA library, and/or a cDNA library.

The term "sequence variant of interest", includes, but is not limited to, any genetic sequence preferably present within a cell, such as, for example a gene, part of a gene, or a non-coding sequence within or adjacent to a gene. The sequence variant of interest may be present in a chromosome, an episome, an organellar genome such as mitochondrial or chloroplast genome or genetic material that can exist independently to the main body of genetic material such as an infecting viral genome, plasmids, episomes, transposons for example. A sequence variant of interest may be within the coding sequence of a gene, within transcribed non-coding sequence such as, for example, leader sequences, trailer sequence or introns. Said nucleic acid sequence variant of interest may be present in a double or a single strand nucleic acid.

A sequence variant of interest, or genetic variant of interest, is herein understood as a sequence of interest having more than one variant, preferably at least two variants, e.g. there may be 2, 3, 4, 5, 6, 7, 8, 9, 10 or more variants of a sequence of interest present in a population.

The sequence variant of interest can be, but is not limited to, a sequence having or suspected of having, a polymorphism, e.g. a SNP.

The term "oligonucleotide" as used herein denotes a single-stranded multimer of nucleotides, preferably of about 2 to 200 nucleotides, or up to 500 nucleotides in length. Oligonucleotides may be synthetic or may be made enzymatically, and, in some embodiments, are about 10 to 50 nucleotides in length. Oligonucleotides may contain ribonucleotide monomers (i.e., may be oligoribonucleotides) or deoxyribonucleotide monomers. An oligonucleotide may be about 10 to 20, 20 to 30, 30 to 40, 40 to 50, 50 to 60, 60 to 70, 70 to 80, 80 to 100, 100 to 150, 150 to 200, or about 200 to 250 nucleotides in length, for example.

"Reducing complexity" or "complexity reduction" is to be understood herein as the reduction of a complex nucleic acid sample, such as samples derived from genomic DNA, cfDNA derived from liquid biopsies and the like. Reduction of complexity results in the enrichment of one or more polynucleotides of interest (i.e. comprising a sequence variant of interest) comprised within the complex starting material and/or the generation of a subset of the sample, wherein the subset comprises or consists of one or more polynucleotides comprising the sequence variant of interest, which were comprised within the complex starting material, while non-target sequences or fragments are reduced in amount by at least 20%, 30%, 40%, 50%, 60%, 70%, 80%, 90%, 91%, 92%, 93%, 94%, 95%, 96%, 97%, 98% or 99% as compared to the amount of non-target sequences or fragments in the starting material, i.e. before complexity reduction. Reduction of complexity is in general performed prior to further analysis or method steps, such as amplification, barcoding, sequencing, determining epigenetic variation etc. Preferably complexity reduction is reproducible complexity reduction, which means that when the same sample is reduced in complexity using the same method, the same, or at least comparable, subset is obtained, as opposed to random complexity reduction. Preferably, reproducible complexity reduction means that the ratio of the sequence variant of interest and the reference sequence stays the same or essentially the same when tested under the same conditions. Examples of complexity reduction methods include for example AFLP® (Keygene N.V., the Netherlands; see e.g., EP 0 534 858), Arbitrarily Primed PCR amplification, capture-probe hybridization, the methods described by Dong (see e.g., WO 03/012118, WO 00/24939) and indexed linking (Unrau P. and Deugau K.V. (1994) Gene 145:163-169), the methods described in WO2006/137733; WO2007/037678; WO2007/073165; WO2007/073171, US 2005/260628, WO 03/010328, US 2004/10153, genome portioning (see e.g. WO 2004/022758), Serial Analysis of Gene Expression (SAGE; see e.g. Velculescu et al., 1995, see above, and Matsumura et al., 1999, The Plant Journal, vol. 20 (6): 719-726) and modifications of SAGE (see e.g. Powell, 1998, Nucleic Acids Research, vol. 26 (14): 3445-3446; and Kenzelmann and Mühlemann, 1999, Nucleic Acids Research, vol. 27 (3): 917-918), MicroSAGE (see e.g. Datson et al., 1999, Nucleic Acids Research, vol. 27 (5): 1300-1307), Massively Parallel Signature Sequencing (MPSS; see e.g. Brenner et al., 2000, Nature Biotechnology, vol. 18:630-634 and Brenner et al., 2000, PNAS, vol. 97 (4): 1665-1670), self-subtracted cDNA libraries (Laveder et al., 2002, Nucleic Acids Research, vol. 30 (9): e38), Real-Time Multiplex Ligation-dependent Probe Amplification (RT-MLPA; see e.g. Eldering et al., 2003, vol. 31 (23): e153), High Coverage Expression Profiling (HiCEP; see e.g. Fukumura et al., 2003, Nucleic Acids Research, vol. 31 (16):

e94), a universal micro-array system as disclosed in Roth et al. (Roth et al., 2004, Nature Biotechnology, vol. 22 (4): 418-426), a transcriptome subtraction method (see e.g. Li et al., Nucleic Acids Research, vol. 33 (16): e136), and fragment display (see e.g. Metsis et al., 2004, Nucleic Acids Research, vol. 32 (16): e127).

The term "sequencing," as used herein, refers to a method by which the identity of at least 10 consecutive nucleotides (e.g., the identity of at least 20, at least 50, at least 100 or at least 200 or more consecutive nucleotides) of a polynucleotide are obtained. The term "next-generation sequencing" refers to the so-called parallelized sequencing-by-synthesis or sequencing-by-ligation platforms, e.g., such as currently employed by Illumina, Life Technologies (part of ThermoFisher Scientific), Pacific Biosciences and Roche. Next-generation sequencing methods may also include nanopore sequencing methods, such as those commercialized by Oxford Nanopore Technologies, or electronic-detection based methods such as Ion Torrent technology commercialized by Life Technologies (part of ThermoFisher Scientific).

"Amplification" used in reference to a nucleic acid or nucleic acid reactions, refers to in vitro methods of making copies of a particular nucleic acid, such as a target nucleic acid, or a tagged nucleic acid. Numerous methods of amplifying nucleic acids are known in the art, and amplification reactions include polymerase chain reactions, ligase chain reactions, strand displacement amplification reactions, rolling circle amplification reactions, transcription-mediated amplification methods such as NASBA (e.g., U.S. Pat. No. 5,409,818), loop mediated amplification methods (e.g., "LAMP" amplification using loop-forming sequences, e.g., as described in U.S. Pat. No. 6,410,278) and isothermal amplification reactions. The nucleic acid that is amplified can be DNA comprising, consisting of, or derived from DNA or RNA or a mixture of DNA and RNA, including modified DNA and/or RNA. The products resulting from amplification of a nucleic acid molecule or molecules (i.e., "amplification products"), whether the starting nucleic acid is DNA, RNA or both, can be either DNA or RNA, or a mixture of both DNA and RNA nucleosides or nucleotides, or they can comprise modified DNA or RNA nucleosides or nucleotides.

As used herein, the term "adapter" is a single-stranded, double-stranded, partly double-stranded, Y-shaped or hairpin nucleic acid molecule that can be attached, preferably ligated, to the end of other nucleic acids, e.g., to one or both strands of a double-stranded DNA molecule, and preferably has a limited length, e.g., about 10 to about 200, or about 10 to about 100 bases, or about 10 to about 80, or about 10 to about 50, or about to about 30 base pairs in length, and is preferably chemically synthesized. The double-stranded structure of the adapter may be formed by two distinct oligonucleotide molecules that are base paired with one another, or by a hairpin structure of a single oligonucleotide strand. As would be apparent, the attachable end of an adapter may be designed to be compatible with, and optionally ligatable to, overhangs made by cleavage by an endonuclease, may be designed to be compatible with an overhang created after addition of a non-template elongation reaction (e.g., 3'-A addition), or may have blunt ends. Hence optionally, the fully or partially double-stranded adapter comprises an overhang, preferably a T-overhang, wherein preferably the T-overhang is a 3' overhang, preferably a 3' overhang of a single T (thymidine) nucleotide. Preferably, there is a phosphorothioate bond before this terminal T. Optionally, the strand opposite to the strand comprising the T-overhang, is 5'-phosphorylated.

An "endonuclease" is an enzyme that hydrolyses at least one strand of a duplex DNA upon binding to its recognition site. An endonuclease is to be understood herein as a site-specific endonuclease and the terms "endonuclease" and "nuclease" are used interchangeable herein. A "restriction endonuclease" or "restriction enzyme" is to be understood herein as an endonuclease that hydrolyses both strands of the duplex at the same time to introduce a double strand break in the DNA.

A "unique molecular index" or "UMI" is a substantially unique tag (e.g. barcode), preferably fully unique, that is specific for a nucleic acid molecule, e.g. unique for each single polynucleotide. The term "UMI" is used herein to refer to both the sequence information of a polynucleotide and the physical polynucleotide per se. A UMI can range in length from about 2 to 100 nucleotide bases or more, and preferably has a length between about 4-16 nucleotide bases. The UMI can be a consecutive sequence or may be split into several subunits. Each of these subunits may be present in separate adapters and/or probes. These subunits are preferably used together to generate a substantially unique tag, preferably a fully unique tag, for a single polynucleotide. For instance, if a polynucleotide is a fragment flanked by two adapters, each of these two adapters may comprise a subunit of the UMI. In case the polynucleotide is a ligation product of two probes, each of these two probes may comprise a subunit of the UMI. In order to obtain a consensus sequence, the sequence reads obtained in the method of the invention may be grouped based on the information of each of the two UMI subunits. Preferably a UMI does not contain two or more consecutive identical bases. Furthermore, there is preferably a difference between UMIs of at least two, preferably at least three bases. A UMI may have random, pseudo-random or partially random, or a non-random nucleotide sequence. As a UMI is used to uniquely identify the originating molecule from which the read is derived, reads of amplified polynucleotides can be collapsed into a single consensus sequence from each originating polynucleotide. A UMI may be fully or substantially unique. Fully unique is to be understood herein as that every polynucleotide provided in the method of the invention comprises a unique tag that differs from all the other tags comprised in further polynucleotides in the method of the invention. Substantially unique is to be understood herein in that each polynucleotide provided in the method, product, composition or kit of the invention comprises a random UMI, but a low percentage of these polynucleotides may comprise the same UMI. Preferably, substantially unique molecular identifiers are used in case the chances of tagging the exact same molecule comprising the sequence variant of interest with the same UMI is negligible. Preferably, a UMI is fully unique in relation to a specific sequence variant of interest. A UMI preferably has a sufficient length to ensure this uniqueness for each and every source DNA molecule. In some implementations, a less unique molecular identifier (i.e. a substantially unique identifier, as indicated above) can be used in conjunction with other identification techniques to ensure that each source DNA molecule is uniquely identified during the sequencing process. For instance, the UMI of the invention may be less unique such that different sequence variants of interest may be coupled to the same or similar UMI, e.g. a UMI coupled to a sequence variant of a first gene may have the same sequence as a UMI coupled to a sequence variant of a second gene. In the latter case, the combination of the sequence information of the UMI together with the sequence information of the sequence variant of interest allows for the identification of the originating polynucleotide, i.e. the source molecule or template. A UMI is preferably used to determine that all reads from a single cluster are identified as deriving from a single source molecule or template. In other words, a UMI is preferably used to determine which reads are derived from a single source molecule or template. A source DNA molecule or DNA template is understood herein as a DNA molecule that is copied by amplification or otherwise to produce multiple instances of the DNA molecule.

DETAILED DESCRIPTION

The current methods known in the art for determining the frequency of a certain sequence in a diploid genome cannot be used for determining the frequency in a polyploid genome. For example, the sensitivity of the method can be inadequate to determine the subtle differences in frequencies in polyploid genomes or the method may suffer from an amplification bias, giving inaccurate results.

The inventors now discovered that uniquely tagging a polynucleotide comprising a sequence variant of interest, can result in an accurate determination of the relative frequency of the sequence in a polyploid nucleic acid sample. Such method thus results in a more accurate genotyping of such polyploid nucleic acid samples.

Hence in a first aspect, the invention pertains to a method for determining the relative frequency of a sequence variant of interest in a nucleic acid sample derived from at least one polyploid cell. Preferably, the nucleic acid sample is the genomic DNA derived from at least one polyploid cell. Preferably, the method comprises the steps of:
- a) providing polynucleotides derived from said nucleic acid sample, wherein each polynucleotide comprises a unique molecular index (UMI),
- b) amplifying at least part of the polynucleotides provided in step a);
- c) determining the sequences of at least part of the amplified polynucleotides to obtain sequence reads;
- d) obtaining a consensus sequence of each subset of sequence reads derived from a single polynucleotide of step a) using at least the UMI; and
- e) determining the relative frequency of the sequence variant of interest based on the frequency of consensus sequences comprising the sequence variant of interest and the frequency of a reference sequence.

Preferably the relative frequency of the sequence variant of interest is determined in step e) based on the frequency of consensus sequences comprising the sequence variant of interest and the frequency of consensus sequences comprising the reference sequence.

Preferably, the polynucleotides of step a) are at least one of:
- i) fragments of nucleic acids from the sample, wherein each fragment is attached to a UMI; and
- ii) ligation products of at least one probe comprising a sequence that can hybridize to the sequence variant of interest in a nucleic acid from the sample, wherein each ligation product comprise a UMI.

Therefore, the invention pertains to a method for determining the relative frequency of a sequence variant of interest in a nucleic acid derived from at least one polyploid cell, wherein the method comprises the steps of:
- a) providing polynucleotides derived from said nucleic acid sample, wherein the polynucleotides are fragments of nucleic acids from the sample, and wherein each fragment is attached to a UMI, b) amplifying at least part of the polynucleotides provided in step a);

c) determining the sequences of at least part of the amplified polynucleotides to obtain sequence reads;

d) obtaining a consensus sequence of each subset of sequence reads derived from a single polynucleotide of step a) using at least the UMI; and e) determining the relative frequency of the sequence variant of interest based on the frequency of consensus sequences comprising the sequence variant of interest and the frequency of a reference sequence.

Further, the invention pertains to a method for determining the relative frequency of a sequence variant of interest in a nucleic acid derived from at least one polyploid cell, wherein the method comprises the steps of:

a) providing polynucleotides derived from said nucleic acid sample, wherein the polynucleotides are ligation products of at least one probe comprising a sequence that can hybridize to the sequence variant of interest in a nucleic acid from the sample, and wherein each ligation product comprises a UMI, b) amplifying at least part of the polynucleotides provided in step a);

c) determining the sequences of at least part of the amplified polynucleotides to obtain sequence reads;

d) obtaining a consensus sequence of each subset of sequence reads derived from a single polynucleotide of step a) using at least the UMI; and e) determining the relative frequency of the sequence variant of interest based on the frequency of consensus sequences comprising the sequence variant of interest and the frequency of a reference sequence.

Preferably, the sequence variant of interest is an allelic variant. The method as detailed herein may therefore also be a method for determining the genotype of the nucleic acid derived from at least one polyploid cell. Within said method, the relative frequency of the allelic variant provides information on the genotype of the sample as further detailed herein.

Preferably, the consensus sequence in step d) is obtained by using at least the UMI for allocating the sequence reads to a single polynucleotide, i.e. the source polynucleotide, of the polynucleotides of step a), which can also be named the template molecule of the method of the invention. Optionally, the subset of sequence reads obtained in step c) comprising the same UMI are grouped. Optionally, only the information of the UMI is used for grouping. Alternatively, both the sequence of the UMI and at least part of the internal sequence of the sequence read is used for grouping. Alternatively or in addition, in case the polynucleotides are ligation products of probes, the distance, i.e. the number of nucleotides, between a locus identifier and a sample identifier can be used for grouping. In an even further embodiment, all three of the UMI, at least part of the sequence of the internal sequence and the distance between the identifiers is used for grouping.

Optionally, one of the sequence reads within one group is taken as consensus sequence. Alternatively, the consensus sequence is obtained by collapsing at least part, preferably all, of the sequence reads within one group.

As indicated above, in addition to using the UMI for determining the consensus sequence, the length of the sequence reads may be taken into account. Hence, the consensus sequence may be obtained by collapsing sequence reads that comprise the same UMI and have the same, or a highly similar, read length.

Optionally, the method further comprises a step of producing a report indicating the determined relative frequencies of the sequence variant of interest or the determined genotype of the nucleic acid sample or any further conclusion derived therefrom. Any further conclusion can be e.g. the resulting phenotype.

Optionally, step a) is preceded by a step of providing a nucleic acid sample. The nucleic acid sample of the method of the invention is derived from at least one polyploid cell, optionally from two or more cells preferably originating from the same individual, preferably from the same tissue of the same individual.

The relative frequency in the method of the invention may be calculated as the number of times the sequence variant of interest occurs in a nucleic acid sample (i.e. the frequency) in relation to, or divided by, the number of times a reference sequence occurs in said sample or a comparable sample. In step e) of the method of the invention, the relative frequency of the sequence variant of interest is determined, which is based on the frequency of the sequence of interest and the frequency of a reference sequence. The frequency of the sequence variant of interest, i.e. the number of times a sequence variant of interest is present in the sample of the method, is based on the number of consensus sequences obtained in step d) that comprise the sequence variant of interest. Each consensus sequence comprising the sequence variant of interest is preferably counted as one in the assessment of the frequency of the sequence variant of interest in the sample. The number of consensus sequences comprising the sequence variant of interest preferably reflects the number of sequence variants of interest in the nucleic acid sample.

In case the sequence variant of interest is an allele, the relative frequency can be expressed as the number of times the allele occurs in a nucleic acid sample, divided by the total of the number of times the allele and any allelic variant thereof occurs in the nucleic acid sample.

Alternatively, the relative frequency can be expressed as the number of times the allele occurs in a nucleic acid sample, divided by the number of times the allelic variant(s) thereof occur(s) in the nucleic acid sample. Optionally, the frequency of all allelic variants can be established based on the frequency of the locus comprising said allelic variants. The frequency of all allelic variants can also be established based on the summation of frequencies of all allelic variants. In the latter case, the reference sequence may encompass multiple sequences, i.e. the sequences of all allelic variants. Preferably, the relative frequency in the method of the invention can be expressed as the number of times a sequence variant of interest at a specific locus occurs in a nucleic acid sample, divided by the total of the number of times the locus occurs in a nucleic acid sample. The method of determining the relative frequency of an allelic variant can also be considered a method for genotyping of a nucleic acid sample.

The reference sequence may be a further variant of the sequence of interest, e.g. a first, second, third, fourth, or further variant of the sequence of interest. Alternatively, the reference sequence may be an unrelated sequence. The frequency of the reference sequence in the sample may be known. Alternatively, the frequency of the reference sequence in the sample needs to be determined. Therefore, the method of the invention may further comprise determining the frequency of said reference sequence, preferably by performing the identical steps of the method of the invention as for assessing the frequency of the sequence variant of interest, preferably using the same sample, but for determining the frequency of said reference sequence. Said determination may be done in parallel or sequentially with determining the amount of sequence variant of interest in the sample, preferably in parallel, meaning that the determination is done on the same sample at the same time.

The skilled person is aware how to assess different variants and/or reference sequences together with a sequence variant of interest. For instance, in case an OLA assay is performed on a sample, multiple different probes can be used simultaneously, wherein each probe selectively hybridizes to a specific variant or reference sequence, and wherein preferably such probe comprises an allele or locus specific identifier, preferably next to the UMI. In case the method of the invention is performed on fragments of the nucleic acid of the sample, the skilled person is able to collect information of the amount of variants or unrelated reference sequence from the sample from the sequence information obtained from step c) of the method of the invention.

In a non-limiting example, if the first sequence variant of interest is present once in a tetraploid cell and a variant sequence thereof is present three times, the relative frequency of the first sequence variant of interest can be expressed in relation to the total number of times the locus occurs, i.e. 0.25 or 25%, or in relation to the variant sequences, i.e. 0.33 or 33%. The relative frequency is thus the fraction or proportion of times a sequence occurs and can be expressed as a percentage, e.g. between 0-100%, or a fraction, e.g. between 0 and 1.

The method as disclosed herein can be used to determine the relative frequency of an allele in a nucleic acid sample, i.e. in case the sequence variant of interest is the sequence of a specific allele, or a part thereof.

In a non-limiting example using a tetraploid organism and a bi-allelic polymorphism, the first sequence, e.g. the first allele, is annotated as "A" and the second sequence, e.g. the second allele, is annotated as "B". In case one chromosome comprises one copy of "A" and the other 3 chromosomes each comprise one copy of "B", the relative frequency of the allele "A" can be expressed as 0.25 and the relative frequency of the allele "B" as 0.75. It is understood herein that the relative frequency of the sequence variant of interest (e.g. "A" in this non-limiting example) can be determined by comparing the presence of one allelic variant (e.g. "A") with the presence of the other allele (e.g. "B" in this non-limiting example). The relative frequency of A in this non-limiting example can thus be calculated as (presence A)/(presence A+presence B).

Similarly, in a non-limiting example using a polyploid organism and a multi-allelic polymorphism, the first sequence, e.g. the first allele, may be annotated as "A" and all other variants may be annotated as "B". The relative frequency may be calculated as provided above, i.e. as (presence A)/(presence A+presence B).

Alternatively or in addition, the relative frequency of the sequence variant of interest (e.g. "A" in this non-limiting example) can be determined by comparing the presence of one allele (e.g. "A") with the presence of an unrelated reference sequence (e.g. "X"), which preferably is a sequence of a locus that is unrelated to the locus of the sequence variant of interest, wherein the unrelated reference sequence has a known copy number in the nucleic acid sample and has a relative frequency of 1. In the non-limiting example provided above, "A" is present once and the unrelated reference sequence ("X") is present 4 times (e.g. once per chromosome). The relative frequency of "A" in this non-limiting example can thus be calculated as (presence A)/(presence X*copy number A), e.g. being 0.25.

In an embodiment, the sequence variant of interest can be present twice or more often per chromosome, i.e. the copy number is 2 or more. In a non-limiting example, a tetraploid organism has e.g. two copies of the allele per chromosome, and e.g. one chromosome comprises "AB" and three chromosomes comprise "BB", the relative frequency expressed as in relation to the number of times the locus occurs is 0.125 as A=1 and B is 7 in the formula A/(A+B) above. Similarly A is 1, X is 4 and copy number of A is 2 in the formula A/(X*copy number A) above.

The skilled person understands straightforwardly how to adjust the formulas provided above to calculate the relative frequency of the sequence variant of interest. In addition, similar formulas can be used to determine the ratio between the sequence variant of interest and the variants thereof, including the ratio between an allele and an allelic variant thereof.

The method may further require a step of obtaining the information of the amount of the total number of variants of the sequence variant of interest (in the non-limiting examples above indicated as "A+B") in the sample, or the absolute amount of an unrelated reference sequence (in the non-limiting examples above indicated as "X") in the sample, which may be known or needs to be assessed.

Preferably, the relative frequency is determined by determining the ratio between the consensus sequence and a reference sequence. Preferably, the reference sequence is derived from, or obtained from, the same nucleic acid sample comprising the sequence variant of interest.

The nucleic acid sample may or may not comprise the sequence of interest. The nucleic acid sample may comprise the sequence of interest 1, 2, 3, 4, 5, 6, 7, 8, 9, 10 or more times, e.g. dependent of the polyploidy level of the cell, its allelic state, and the number genomes present in the sample. The nucleic acid sample may or may not comprise the reference sequence. The nucleic acid may comprise the reference sequence 1, 2, 3, 4, 5, 6, 7, 8, 9, 10 or more times, e.g. dependent of the polyploidy level of the cell, its allelic state, and the number genomes present in the sample.

The relative frequency is preferably determined by the number of consensus sequences and the number or reference sequences present in the nucleic acid sample.

The number of consensus sequences may be determined using the method of the invention. Preferably, the number of reference sequences may additionally be determined using the method of the invention. Preferably, the method step for providing the polynucleotide comprising the sequence variant of interest additionally provides for a polynucleotide comprising a reference sequence.

Preferably, the method of the invention comprises the steps of:

a1) providing a nucleic acid sample comprising a sequence of interest and a reference sequence;

a2) providing polynucleotides derived from said nucleic acid sample, wherein these polynucleotides are:

(i) fragments of nucleic acids from the sample, wherein each fragment is attached to a UMI; or (ii) ligation products of at least one probe comprising a sequence that can hybridize to the sequence variant of interest or reference sequence in a nucleic acid from the sample, wherein each ligation product comprise a UMI;

b) amplifying at least part of the polynucleotides provided in step a);

c) determining the sequences of at least part of the amplified polynucleotides to obtain sequence reads;

d) obtaining a consensus sequence of each subset of sequence reads derived from a single polynucleotide of step a) using at least the UMI; and e) determining the relative frequency of the sequence variant of interest based on the frequency of consensus sequences comprising the sequence variant of interest and the frequency of consensus sequences comprising the reference sequence.

Sequence Variant of Interest

The sequence variant of interest may be any sequence within a nucleic acid sample, e.g., a gene, gene complex, locus, pseudogene, regulatory region, highly repetitive region, polymorphic region, or portion thereof. The sequence variant of interest can be a naturally-occurring sequence or an artificially-introduced sequence. A non-limiting example of an artificially-introduced sequence is a sequence that is introduced in the nucleic acid sample by means of an expression vector and/or by means of CRISPR-technology. Similarly, an artificially introduced sequence may be obtained by e.g. random mutagenesis. The sequence variant of interest may also be a region comprising genetic or epigenetic variations indicative for a phenotype or disease. Preferably, there can be more than one variant of the sequence of interest present in the nucleic acid sample, wherein at least one variant is the sequence variant of interest.

In some embodiments, a nucleic acid sample comprises more than one sequence variant of interest that is determined using the method of the invention. Hence, a nucleic acid sample may comprise about 1, 2, 3, 4, 5, 6, 7, 8, 9, 10, 20, 30, 40, 50, 100, 150, 200, 250, 300, 350, 400, 450, 500, 550, 600, 650, 700, 750, 800, 850, 900, 950, 1000 or more sequences of interest, of which the relative frequency is determined using the method of the invention. Hence in an embodiment, the relative frequency of two or more sequences of interest is determined. Optionally, the one or more sequences of interest are structurally or functionally related.

It is understood herein that a plurality of sequence variants of interest may be two or more variants of the same gene. Alternatively or in addition, the plurality of sequence variants of interest may be sequence variants of different genes.

In an embodiment, the polynucleotide comprising a sequence variant of interest may comprise both natural and non-natural, artificial, or non-canonical nucleotides including, but not limited to, DNA, RNA, BNA (bridged nucleic acid), LNA (locked nucleic acid), PNA (peptide nucleic acid), morpholino nucleic acid, glycol nucleic acid, threose nucleic acid, epigenetically modified nucleotide such as methylated DNA, and mimetics and combinations thereof.

A sequence variant of interest can be, but is not limited to, an allele or a part thereof. An allele is defined herein as a variant form of a certain gene. The terms "allele" and "an allelic variant" can be used interchangeably herein. As a non-limiting example, there can be two allelic variants (bi-allelic, A or B). However, the method of the invention is not limited to two allelic variants. For example, there may be 3, 4, 5, 6, 7, 8, 9 or more allelic variants. The method of the invention can be used to determine the relative frequency of e.g. only one allelic variant (A), or e.g. the ratio between two or more allelic variants (e.g. the ratio between A or B).

The sequence variant of interest, e.g. the allelic variant of interest, may be a genetic marker.

It is understood herein that this allelic variation may occur in the coding region of a gene and/or in a non-coding region of a gene. In addition or alternatively, the variation may occur in a splice site and/or in a regulatory element of the gene, such as, but not limited to, a promoter region. The difference between two alleles may be the presence or absence of a SNP. Preferably, the SNP results in an amino acid change in the translated protein. Preferably, the SNP results in a single amino acid change.

Alternatively or in addition, the sequence variant of interest is, or is part of, an intergenic sequence, wherein preferably different variants exists in a population. Preferably, the sequence variant of interest comprises a SNP.

In a preferred embodiment, the sequence variant of interest is an allelic variant of a gene of interest (g.o.i.). Preferably, the allelic variant confers a phenotypic trait to an organism, preferably confers a phenotypic trait or characteristic to a plant. The term "plant characteristic" means any characteristic of a plant, plant cell or plant tissue.

In an embodiment, the allele confers a plant characteristic to a plant selected from the group consisting of plant development, plant growth, yield, biomass production, plant architecture, plant biochemistry, plant physiology, metabolism, survival capacity and stress tolerance. Alternatively or in addition, the plant characteristic is selected from the group consisting of DNA synthesis, DNA modification, endoreduplication, cell cycle, cell wall biogenesis, transcription regulation, signal transduction, storage lipid mobilization, and photosynthesis.

The term "confers a plant characteristic" as used herein encompasses any change in the plant characteristic such as increase, decrease or change in time or place.

It is understood herein that the allele can alter the plant characteristic by introducing, increasing, decreasing, or removing the expression of a certain gene product. Whether the plant characteristic is altered due to an introduced expression of a gene product, increased expression of a gene product, decreased expression of a gene product, or removed expression of a gene product is dependent on the type of allele and/or the type of plant characteristic.

Detailed herein below are, non-limiting, examples of plant characteristics influenced by, or due to, an allelic variant.

"Growth" refers to the capacity of the plant or of plant parts to expand and increase in biomass. Altered growth refers amongst others to altered growth rate, cycling time, the size, expansion or increase of the plant. Additionally and/or alternatively, growth characteristics may refer to cellular processes comprising, but not limited to, cell cycle (entry, progression, exit), cell division, cell wall biogenesis and/or DNA synthesis, DNA modification and/or endoreduplication.

"Yield" refers to the harvestable part of the plant. "Biomass" refers to any part of the plants. These terms also encompass an increase in seed yield, which includes an increase in the biomass of the seed (seed weight) and/or an increase in the number of (filled) seeds and/or in the size of the seeds and/or an increase in seed volume, each relative to corresponding wildtype plants. An increase in seed size and/or volume may also influence the composition of seeds. An increase in seed yield could be due to an increase in the number and/or size of flowers. An increase in yield may also increase the harvest index, which is expressed as a ratio of the total biomass over the yield of harvestable parts, such as seeds.

"Plant development" means any cellular process of a plant that is involved in determining the developmental fate of a plant cell, in particular the specific tissue or organ type into which a progenitor cell will develop. Typical plant characteristics according to the present invention are therefore characteristics relating to cellular processes relevant to plant development such as for example, morphogenesis, photomorphogenesis, shoot development, root development, vegetative development, reproductive development, stem elongation, flowering, regulatory mechanisms involved in determining cell fate, pattern formation, differentiation, senescence, time of flowering and/or time to flower.

Plant architecture", as used herein refers to the external appearance of a plant, including any one or more structural features or a combination of structural features thereof. Such structural features include the shape, size, number, position, colour, texture, arrangement, and patterning of any cell, tissue or organ or groups of cells, tissues or organs of a plant, including the root, stem, leaf, shoot, petiole, trichome, flower, petal, stigma, style, stamen, pollen, ovule, seed, embryo, endosperm, seed coat, aleurone, fibre, fruit, cambium, wood, heartwood, parenchyma, aerenchyma, sieve element, phloem or vascular tissue, amongst others.

The term "stress tolerance" is understood as the capability of better survival and/or better performing in stress conditions such as environmental stress, which can be biotic or abiotic. Salinity, drought, heat, chilling and freezing are all described as examples of conditions which induce osmotic stress. The term "environmental stress" as used in the present invention refers to any adverse effect on metabolism, growth or viability of the cell, tissue, seed, organ or whole plant which is produced by a non-living or non-biological environmental stressor.

More particularly, it can encompass environmental factors such as water stress (flooding, water logging, drought, dehydration), anaerobic (low level of oxygen, $CO_2$ etc.), aerobic stress, osmotic stress, salt stress, temperature stress (hot/heat, cold, freezing, frost) or nutrients deprivation, pollutants stress (heavy metals, toxic chemicals), ozone, high light, pathogen (including viruses, bacteria, fungi, insects and nematodes) and combinations of these.

Biotic stress is stress as a result of the impact of a living organism on the plant. Examples are stresses caused by pathogens (virus, bacteria, nematodes insects etc.). Another example is stress caused by an organism, which is not necessarily harmful to the plant, such as the stress caused by a symbiotic or an epiphyte. Accordingly, particular plant characteristics obtained by modification of the second gene, i.e. the gene of interest, can encompass early vigour, survival rate, stress tolerance.

Characteristics related to "plant physiology" can encompass characteristics of functional processes of a plant, including developmental processes such as growth, expansion and differentiation, sexual development, sexual reproduction, seed set, seed development, grain filling, asexual reproduction, cell division, dormancy, germination, light adaptation, photosynthesis, leaf expansion, fiber production, secondary growth or wood production, amongst others; responses of a plant to externally-applied factors such as metals, chemicals, hormones, growth factors, environment and environmental stress factors (e.g. anoxia, hypoxia, high temperature, low temperature, dehydration, light, day length, flooding, salt, heavy metals, amongst others), including adaptive responses of plants to said externally-applied factors. Particular plant physiology characteristics which are influenced by or are due to a particular allele can further encompass altered storage lipid mobilization, photosynthesis, transcription regulation and signal transduction.

Plant characteristics related to "plant biochemistry" are to be understood by those skilled in the art to preferably refer to the metabolic characteristics. "Metabolism" can be used interchangeable with biochemistry. Metabolism and/or biochemistry encompass catalytic or assimilation or other metabolic processes of a plant, including primary and secondary metabolism and the products thereof, including any element, small molecules, macromolecules or chemical compounds, such as but not limited to starches, sugars, proteins, peptides, enzymes, hormones, growth factors, nucleic acid molecules, celluloses, hemicelluloses, calloses, lectins, fibres, pigments such as anthocyanins, vitamins, minerals, micronutrients, or macronutrients, that are produced by plants.

In a preferred embodiment, the sequence variant of interest may be present once, or 2, 3, 4, 5, 6, 7, 8, 9, 10 or more times per chromosome, e.g. the copy number May 1 or 2, 3, 4, 5, 6, 7, 8, 9, 10 or more. In a preferred embodiment, there is no copy number variation of the sequence variant of interest. Hence in a preferred embodiment, there is no copy number variation of the allele or allelic variant in the polyploid genome. Put differently, in a preferred embodiment the sequence or interest, and in particular the allele, has a single locus in the polyploid genome.

The copy number can be determined using any conventional method known in the art. As a non-limiting example, the length of the (amplification) polynucleotides of the method of the invention may be determined and a variable length may indicate the presence of a copy number of 2 or more.

Nucleic Acid Sample

The nucleic acid sample comprising the sequence variant of interest is preferably obtainable from at least one polyploid cell from a polyploid organism. The nucleic acid sample can be at least one of genomic DNA (gDNA), mitochondrial, cell free DNA (cfDNA), and DNA from a library. Preferably, the nucleic acid sample is genomic DNA, i.e. polyploid genomic DNA.

Preferably, the relative frequency of the sequence variant of interest may be determined within a single nucleic acid sample, i.e. for determining the relative frequency, or ratio, it is not required to make a comparison between different nucleic acid samples. This is an essential difference with for example determining copy number variation, which indeed requires a comparison between a test sample and a reference sample.

Preferably, the nucleic acid sample is obtainable from at least one polyploid cell or tissue. A polyploid cell is defined herein as a cell having more than two paired (homologous) sets of chromosomes. Polyploidy is especially common in plants. In addition, polyploidy may occur in tissues of animals that are otherwise diploid, such as, but not limited to, human muscle tissue. Polyploidy may be a naturally occurring phenomenon, or can be induced, e.g. by chemicals, or cold or heat shock treatment. Non-limiting examples of polyploid-inducing chemicals are colchicine and oryzalin.

In an embodiment, the nucleic acid sample may be derived from at least one polyploid cell or tissue, wherein the at least one polyploid cell or tissue is selected from the group consisting of a triploid, tetraploid, pentaploid, hexaploid, heptaploid, octaploid, decaploid and dodecaploid cell or tissue.

The at least one polyploid cell can be a eukaryotic or prokaryotic cell, preferably a eukaryotic cell. Polyploidy may occur in highly differentiated tissues, such as but not limited to, the liver, heart muscle, bone marrow and placenta. Hence, the nucleic acid sample maybe derived from a differentiated polyploid cell, e.g. from an otherwise diploid organism.

The at least one polyploid cell may be an animal, bacterial, fungal or plant cell. The nucleic acid sample can be obtained from any polyploid cell. As a non-limiting example, the nucleic acid sample may be obtained from at least one polyploid animal cell, such as, but not limited to a cell derived from a flatworm, leech, brine shrimp, a salmonid, cyprinid, xenopus, lizard or mole salamander. Alternatively, the nucleic acid sample for use in the invention can be obtained from at least one polyploid plant cell. The polyploid plant cell may be derived from a polyploid plant or a ploidy chimera.

It has been suggested that up to 30%-80% of living plant species are polyploid. Polyploid plants can arise spontaneously in nature by several mechanisms, including meiotic or mitotic failures, and fusion of unreduced (2n) gametes. The at least one polyploid plant cell can be an allopolyploid plant cell or an autopolyploid plant cell. An allopolyploid plant cell is defined herein as a polyploid plant cell having chromosomes derived from different species, e.g. due to interspecific hybridization. An autopolyploid plant cell is defined herein as a plant cell having chromosomes derived from the same species, e.g. having more than two complete copies of a genome, e.g. due to genome doubling. Preferably, the at least one polyploid plant cell is an autopolyploid plant cell.

In an embodiment, the nucleic acid sample can be derived from at least one polyploid crop plant cell. In an embodiment, the nucleic acid sample can be derived from at least one polyploid plant cell selected from the group consisting of potato, alfalfa, wheat, tobacco, sugarcane, apple, and cotton.

In an embodiment, the method is preceded by a step of determining the polyploidy level of a cell. Any conventional method for determining the polyploidy level can be used in the method of the invention. Such methods for determining the polyploidy level include direct methods as well as indirect methods. A direct method includes, but is not limited to chromosome counting. An indirect method includes, but is not limited to, at least one of flow cytometry, stomatal size, stomatal density, cell size, chloroplast number of the guard cells and morphological observations.

Polynucleotide

The method of the invention preferably comprises a step of obtaining polynucleotides comprising the sequence of interest, and optionally the reference sequence. The sequence of interest may be the sequence variant of interest or a sequence suspected to be the sequence variant of interest. In addition or alternatively, the polynucleotides comprise the reverse complement of the sequence of interest, or optionally the reference sequence. It is therefore understood herein that the sequence variant of interest in a polynucleotide is identical, i.e. has 100% sequence identity, to the sequence variant of interest in the nucleic acid sample, i.e. the sequence of which the relative frequency is to be determined. Alternatively or in addition, the sequence variant of interest in a polynucleotide is fully complementary, i.e. has 100% sequence complementarity, to the sequence variant of interest in the nucleic acid sample. Likewise the optional reference sequence in a polynucleotide is identical, i.e. has 100% sequence identity, to the optional reference sequence in the nucleic acid sample. Alternatively or in addition, the optional reference sequence in a polynucleotide is fully complementary, i.e. has 100% sequence complementarity, to the optional reference sequence in the nucleic acid sample. The polynucleotides each comprise a unique molecular index (UMI) as defined herein.

The UMI may be applied to a DNA molecule, such as an oligonucleotide, using any conventional method known in the art. As a non-limiting example, the UMIs may be applied to the DNA molecules by methods that physically link or bond the UMIs to the DNA molecules, e.g., by ligation or transposition through polymerase, endonuclease, transposases, etc. In addition or alternatively, the UMI may be incorporated in the DNA molecule during synthesis using any mixture of nucleotides.

The polynucleotides can be linear or circular nucleic acid molecules. In addition, the polynucleotides can be a single-stranded or a double-stranded nucleic acid molecules.

In case the UMI for use in the invention is attached to a fragment of the nucleic acid sample as part of an adapter, the adapter may be single-stranded, double-stranded or Y-shaped. Using the UMI-comprising single-stranded or Y-shaped adapter, it is possible to distinctly label the top and the bottom strand of a nucleic acid fragment, taken that, in case of a Y-shaped adapter, the UMI is part of the non-duplex structure of the adapter. For example in case of sheared genomic DNA where the fragment size in combination with its sequence is unique, or substantially unique, for each fragment, reads of the top and its bottom strand may be grouped based on the sequence information obtained in step b of the method of the invention. Alternatively, using a double-stranded or Y-shaped adapter, it is possible label the top and bottom strand with a complementary UMI, taken that, in case of a Y-shaped adapter, the UMI is part of the duplex structure of the adapter. In this case, the top and its bottom strand may grouped based on the sequence information of the UMI obtained in step b of the method of the invention.

Oligonucleotide Ligation Assay

In an embodiment, the polynucleotide of the method of the invention may be a single-stranded nucleic acid molecule. In this embodiment, the polynucleotide may be obtainable by oligonucleotide ligation, preferably using the sequence variant of interest or its reverse complement in the nucleic acid sample as a template strand, i.e. a target sequence strand, in the OLA assay. Oligonucleotide ligation includes the ligation of two ends of a single oligonucleotide probe, thereby generating a single-stranded circular polynucleotide. Similarly, oligonucleotide ligation includes the ligation of two, or more, oligonucleotide probes to obtain a single-stranded linear polynucleotide comprising the sequence variant of interest, or its complement.

When used in the context of an oligonucleotide ligation assay, the term "oligonucleotide ligation (assay) probe", "OLA probe", "oligonucleotide probe" and "probe" can be used interchangeably herein.

It is understood herein that the ligation may be a direct ligation of the oligonucleotide ligation probes after hybridization of the oligonucleotide ligation probes to the template strand comprising the sequence variant of interest, or that the ligation follows after e.g. a step of filling a gap (gap filling) present in between the two hybridized oligonucleotide ligation probes. Gap filling can be performed using any conventional gap filling method known in the art.

Preferred is an oligonucleotide ligation assay (OLA) to detect the sequence variant of interest in the nucleic acid sample. OLA is well-known in the art and the skilled person knows how to perform an OLA assay. A typical OLA assay uses at least one or two oligonucleotide ligation probes that can only ligate when either (i) both the 5' end and 3' end of the same oligonucleotide ligation probe (when using a single oligonucleotide ligation probe) or (ii) the 5'-end of a first oligonucleotide ligation probe and the 3'-end of a second oligonucleotide ligation probe (when using at least two oligonucleotides), hybridize to the sequence variant of interest, or to its reverse complement, in the nucleic acid sample.

The first and second probe may be designed to hybridize to directly adjacent sequences of a template strand comprising the sequence variant of interest, or to sequences of the template strand that are separated by a sequence of the template strand, resulting in a gap that can be filled as indicated above. Probes may be designed such that the probe or probe part that hybridizes with its 3' end to the template strand comprising the sequence variant of interest, comprises the nucleotide that hybridizes to the variant of interest or the nucleotide that hybridizes to variants thereof at its 3'-end. Such probe is called herein an "allele-specific" probe or oligonucleotide. In case of a gap filling oligonucleotide ligation assay, the probes used may be agnostic to the variant of interest which may be within the gap that is filled after hybridization of the probes.

The circular or linear ligated product herein may be the polynucleotide of the method of the invention. In case two or more oligonucleotide ligation probes are used in the OLA assay, one of the oligonucleotide ligation probes is typically annotated as an "allele-specific" oligonucleotide or probe and one oligonucleotide as the "locus-specific" oligonucleotide or probe. As the name also implies, the "allele-specific" probe only hybridizes to a specific allele variant (i.e. the sequence variant of interest), while the locus-specific probe preferably hybridizes to a sequence common to all allelic variants. In case two oligonucleotide ligation probes are used in a gap filling oligonucleotide ligation assay, both oligonucleotides may be a "locus-specific" oligonucleotide or probe.

The OLA-principle is described among others in U.S. Pat. No. 4,988,617 (Landegren et al.), Nilsson et al. Human mutation, 2002, 19, 410-415; Science 1994, 265:2085-2088; U.S. Pat. No. 5,876,924; WO98/04745; WO98/04746; U.S. Pat. Nos. 6,221,603; 5,521,065; 5,962,223; EP185494B1; U.S. Pat. Nos. 6,027,889; 4,988,617; EP246864B1; U.S. Pat. No. 6,156,178; EP745140 B1; EP964704 B1; WO03/054511; US2003/0119004; US2003/190646; EP1313880; US2003/0032016; EP912761; EP956359; US2003/108913; EP1255871; EP1194770; EP1252334; WO96/15271; WO97/45559; US2003/0119004A1; U.S. Pat. No. 5,470,705; WO01/57269; WO03/006677; WO01/061033; WO2004/076692; WO2006/076017; WO2012/019187; WO2012/021749; WO2013/106807; WO2015/154028; WO2015/014962 and WO2013/009175, which are incorporated herein by reference. Further advancements in the OLA techniques have been reported by KeyGene, Wageningen, the Netherlands, which is incorporated herein by reference. In WO2004/111271, WO2005/021794, WO2005/118847 and WO03/052142, which are incorporated herein by reference, KeyGene has described several methods and probe designs that improved the reliability of oligonucleotide ligation assays. These applications further disclose the significant improvement in multiplex levels that can be achieved. Also "SNPWave: a flexible multiplexed SNP genotyping technology", van Eijk M J, et al., Nucleic Acids Res. 2004; 32 (4): e47) and "SNPSelect: A scalable and flexible targeted sequence-based genotyping solution", Hogers et al., PLOS ONE Oct. 12, 2018, describe the improvements made in this field, which are incorporated herein by reference. In WO2007100243, which is incorporated herein by reference, the application of next generation sequencing technology to the results of oligonucleotide ligation assays have been described.

Preferably in the method of the invention, at least one of the oligonucleotide ligation probes used in the ligation, preferably used in an OLA assay, comprises an unique molecular index (UMI). In a preferred embodiment, at least one of the allele-specific and locus-specific oligonucleotide ligation probes comprises a UMI. Preferably, at least the allele-specific oligonucleotide ligation probe comprises a UMI. Alternatively or in addition, at least the locus-specific oligonucleotide ligation probe comprises a UMI. Optionally, both the allele-specific oligonucleotide ligation probe and the locus-specific oligonucleotide ligation probe, that are capable of being ligated together upon hybridizing to their target sequence of the template strand in an OLA assay, comprise a UMI subunit that together make the UMI. Optionally, both the first and second locus-specific oligonucleotide ligation probes, that are capable of forming a ligation product upon hybridizing to their target sequence in the template strand followed by gap filling and ligation in a gap filling oligonucleotide ligation assay, comprise a UMI subunit that together make the UMI. Ligation of the oligonucleotide ligation probes thus preferably results in a polynucleotide comprising the sequence variant of interest, or its complement, and a UMI.

Fragmented Nucleic Acid Sample

In an embodiment, the polynucleotide used in the method of the invention is a double-stranded polynucleotide. The terms "double-stranded" and "duplex" as used herein, describe two complementary polynucleotides that are base-paired, i.e., hybridized together. Complementary nucleotide strands are also known in the art as reverse-complement. In this embodiment, the sequence variant of interest is a small or longer contiguous stretch of nucleotides in a single-strand DNA strand of the duplex DNA, wherein said duplex DNA further comprises a sequence complementary to the sequence variant of interest in the complementary strand of said duplex DNA.

Preferably in this embodiment, the polynucleotide comprises a fragment of the nucleic acid sample and further comprises a UMI. Preferably, the fragmented nucleic acid sample is fragmented genomic DNA (gDNA) and the UMI can be attached to the genomic fragment, preferably the UMI is attached to at least the genomic fragment comprising the sequence variant of interest.

The fragmented nucleic acid sample is preferably fragmented genomic DNA, wherein the genomic DNA is obtainable from a polyploid organism. DNA, and in particular genomic DNA, can be fragmented using any suitable method known in the art. Methods for DNA fragmentation include, but are not limited to, enzymatic digestion and mechanical force.

Non-limited examples of fragmenting the nucleic acid sample using mechanical force include the use of acoustic shearing, nebulization, sonication, point-sink shearing, needle shearing and French pressure cells.

Optionally, fragments of the nucleic acid samples may be modified to comprise an A-tail, preferably to facilitate ligation to a partly, or fully, double-stranded adapter comprising a T-overhang. Hence prior to annealing an adapter to the fragmented nucleic acid, the method of the invention may optionally comprise a step of A-tailing the fragmented nucleic acid sample. A-tailing reactions are well-known in the art and the skilled person straightforwardly understands how to perform an A-tailing reaction, such as e.g. using a Klenow fragment (exo-).

Enzymatic digestion for fragmenting the nucleic acid sample includes, but is not limited to, endonuclease restriction. Enzymatic digestion, such as e.g. used in AFLP® technology, may further result in a complexity reduction of the nucleic acid sample. The skilled person knows which enzymes to select for the DNA fragmentation. As a non-limiting example, at least one frequent cutter and at least one rare cutter can be used for the fragmentation of the nucleic acid sample. A frequent cutter preferably has a recognition site of about 3-5 bp, such as, but not limited to MseI. A rare cutter preferably has a recognition site of >5 bp, such as but not limited to EcoRI.

In certain embodiments, in particular when the sample contains or is derived from a relative large genome, it may be preferred to use a third enzyme, rare or frequent cutter, to obtain a larger set of restriction fragments of shorter size.

The method of the invention is not limited to any specific restriction endonucleases. The endonuclease may be a type II endonuclease, such as EcoRI, MseI, PstI etc. In certain embodiments a type IIS or type III endonuclease may be used, i.e. an endonuclease of which the recognition sequence is located distant from the restriction site, such as, but not limited to, AceIII, AlwI, AlwXI, Alw26I, BbvI, BbvII, BbsI, Bcd, Bce83I, BcefI, BcgI, BinI, BsaI, BsgI, BsmAI, BsmFI, BspMI, EarI, EciI, Eco3II, Eco57I, Esp3I, FauI, FokI, GsuI, HgaI, HinGUII, HphI, Ksp632I, MboII, MmeI, MnlI, NgoV-III, PleI, RleAI, SapI, SfaNI, TaqJI and ZthII III. Restriction fragments can be blunt-ended or have protruding ends, depending on the endonuclease used.

In a preferred embodiment, the recognition site of at least one of the frequent cutter and the rare cutter is within or in close proximity of the sequence variant of interest, e.g. the recognition site of the frequent cutter or the rare cutter is located about 0-10000, 10-5000, 50-1000 or about 100-500 bases from the sequence variant of interest.

The current method as disclosed herein can also be used in AFLP® technology for polyploid cells. The AFLP® technology is e.g. described in more detail in WO2007/114693, WO2006/137733 and WO2007/073165, which are incorporated herein by reference. The AFLP® technology as described in the art can be modified by attaching a UMI to the restricted nucleic acid sample.

In addition or alternatively, the nucleic acid sample may be digested using a programmable nuclease, preferably using at least one of CRISPR-Cas technology, Zinc finger nucleases, TALENs and meganucleases.

In addition or alternatively, prior to sequencing the polynucleotide, the fragmented DNA may be enriched. Before the enrichment step, first a UMI may be attached to the fragmented DNA. Alternatively or in addition, the UMI may be attached to fragmented DNA after the enrichment step and prior to the sequencing step. It is however understood herein that if the enrichment step, or complexity reduction step, involves a step of amplifying the polynucleotide, a UMI is attached to the fragmented DNA prior to amplification.

Enrichment, or complexity reduction, is defined herein above, and preferably the complexity reduction is reproducible complexity reduction. One or more complexity reduction steps can be used, such as, but not limited to, selected from the group consisting of Arbitrarily Primed PCR amplification, capture-probe hybridization, the methods described by Dong (see e.g., WO 03/012118, WO 00/24939) and indexed linking (Unrau P. and Deugau K. V. (1994) Gene 145:163-169), the methods described in WO2006/137733; WO2007/037678; WO2007/073165; WO2007/073171, US 2005/260628, WO 03/010328, US 2004/10153, genome portioning (see e.g. WO 2004/022758), Serial Analysis of Gene Expression (SAGE; see e.g. Velculescu et al., 1995, see above, and Matsumura et al., 1999, The Plant Journal, vol. 20 (6): 719-726) and modifications of SAGE (see e.g. Powell, 1998, Nucleic Acids Research, vol. 26 (14): 3445-3446; and Kenzelmann and Mühlemann, 1999, Nucleic Acids Research, vol. 27 (3): 917-918), MicroSAGE (see e.g. Datson et al., 1999, Nucleic Acids Research, vol. 27 (5): 1300-1307), Massively Parallel Signature Sequencing (MPSS; see e.g. Brenner et al., 2000, Nature Biotechnology, vol. 18:630-634 and Brenner et al., 2000, PNAS, vol. 97 (4): 1665-1670), self-subtracted cDNA libraries (Laveder et al., 2002, Nucleic Acids Research, vol. 30 (9): e38), Real-Time Multiplex Ligation-dependent Probe Amplification (RT-MLPA; see e.g. Eldering et al., 2003, vol. 31 (23): e153), High Coverage Expression Profiling (HiCEP; see e.g. Fukumura et al., 2003, Nucleic Acids Research, vol. 31 (16): e94), a universal micro-array system as disclosed in Roth et al. (Roth et al., 2004, Nature Biotechnology, vol. 22 (4): 418-426), a transcriptome subtraction method (see e.g. Li et al., Nucleic Acids Research, vol. 33 (16): e136), and fragment display (see e.g. Metsis et al., 2004, Nucleic Acids Research, vol. 32 (16): e127).

Preferably, the enrichment step is a hybridization-based capture method. The hybridization between the nucleic acid fragment and a probe can be performed in solution or on a solid support.

In solid-phase hybridization capture, also referred to as array-based hybrid selection (AHS), probes, preferably DNA probes, are bound to a solid support such as, but not limited to, a glass microarray slide. The fragmented DNA is applied to the surface of the support, and DNA fragments comprising the sequence variant of interest hybridize with the immobilized probes. Nonspecific unbound molecules can be washed away, and the enriched DNA can be eluted.

In solution hybridization capture, also referred to as solution-phase hybrid selection (SHS), free DNA or RNA probes may be biotinylated to enable the selection of targeted fragment-probe heteroduplexes using magnetic streptavidin beads. Non-targeted nucleic acid fragments, i.e. fragments not comprising a sequence variant of interest, may be removed from the liquid phase through one or more washes, and targeted fragments may be eluted from the beads (Gasc C. et al., *Sequence capture by hybridization to explore modern and ancient genomic diversity in model and nonmodel organisms*, Nucleic Acids Res. (2016); 44 (10): 4504-4518).

A preferred complexity-reduction method is a solution hybridization capture, preferably a capture-probe hybridization.

In an embodiment, the UMI is attached to the fragmented, and optionally enriched, nucleic acid fragment.

The UMI can be attached using any conventional method known in the art. As a non-limiting example, a short oligonucleotide comprising or consisting of the sequence of the UMI can be attached, e.g. ligated, to the nucleic acid fragment comprising the sequence variant of interest.

Alternatively or in addition, the UMI can be part of, or comprised within, an adapter. Hence, in an embodiment, the method of the invention comprises a step of ligating one or more adapters to the fragmented nucleic acid sample, wherein the UMI is located in at least one adapter. There can be a UMI located in more than one ligated adapter. For example, the UMI can be located in the first adapter, e.g. the adapter that is ligated to one end of the nucleic acid fragment. There may be an additional UMI located in the adapter that is ligated to the other end of the nucleic acid fragment.

Preferably, the UMI is comprised within an adapter, wherein the adapter can ligate to an overhang created by at least one of a frequent cutter and a rare cutter enzyme. Preferably, the UMI is located at least in an adapter that can ligate to the overhang created by a rare cutter. The adapter may optionally comprise one or more sequences for sequencing, preferably deep-sequencing, of the polynucle- otide of the method of the invention. Hence, preferably the adapter used in the method of the invention is compatible with one or more deep-sequencing platforms known in the art.

Preferably, the UMI comprised in the one or more adapt- ers can be located directly adjacent to the overhang that is compatible with the overhang created by the restriction enzyme. Put differently, when the UMI-comprising adapter is ligated to the polynucleotide, the UMI directly flanks the polynucleotide, i.e. is directly 5' or 3' of the polynucleotide. Alternatively or in addition, there can be one or more nucleotides in between the respective 5' end or 3' end of the polynucleotide and the UMI. For example, there can be one or more primer binding sites in between the UMI and the polynucleotide. In addition or alternatively, there can be a further identifier, such as about sample specific identifier, in between the UMI and the polynucleotide.

In an embodiment, the adapter may comprise the follow- ing order of elements: a UMI, a sequencing primer, a sample specific identifier, followed by the end of the adapter that can be ligated to respective 5' or 3' of the polynucleotide. In another embodiment, the adapter may comprise the follow- ing order of elements: a sample specific identifier, a sequenc- ing primer, a UMI, followed by the end of the adapter that can be ligated to respective 5' or 3' of the polynucleotide.

In an embodiment, the UMI is located in at least a P5 adapter and a P7 adapter.

In an embodiment, at least one of the adapters is a protective adapter. The protective adapter may also function as a sequencing adapter. A protective adapter is to be understood herein as an adapter that is specifically designed to protect the target nucleic acid fragment captured by the adapter for exonuclease digestion. Such adapter may protect against exonuclease degradation either by the inclusion of chemical moieties or blocking groups (e.g. phosphorothio- ate) or by a lack of terminal nucleotides (hairpin or stem- loop adapters, or circularizable adapters).

In case the protective adapter comprises chemical moi- eties that protect against exonuclease digestion, such moi- eties are preferably present in the 5'-terminal portion of the transferred strand of the adapter, and/or in the 3'-terminal portion of the non-transferred strand of the adapter. Such protective moieties may be phosphorothioates, which are known in the art to protect against nucleases. For instance phosphorothioates at the 5'-termini will prevent exonuclease degradation by a 5' to 3' exonuclease, such as T7 or lambda exonuclease. The 5'-terminal end of an adapter may com- prise at least 1, 2, 3, 4, 5, 6, 7, 8, 9 or 10 phosphorothioate (PS) bonds. A PS bond substitutes a sulfur atom for a non-bridging oxygen in the phosphate backbone of an oligonucleotide, which renders the internucleotide linkage resistant to nuclease degradation.

Stem-loop or hairpin adapters are single-stranded, but their termini are complementary such that the adapter folds back on itself to generate a double-stranded portion and a single-stranded loop. A stem-loop adapter can be linked to an end of a linear, double-stranded polynucleotide to protect the end from exonuclease degradation by removing the availability of the previously terminal nucleotides to the exonuclease. For example, where stem-loop adapters are joined to the ends of a double-stranded nucleic acid frag- ment, such that there are no terminal nucleotides (e.g., any gaps have been filled and ligated, using a polymerase and ligase, respectively), the resulting molecule lacks terminal nucleotides, instead bearing a single-stranded loop at each end.

Circularizable adapters may protect against exonuclease treatment by a circularization reaction, which is dependent upon the presence of specific sequences present in the adapters and does not rely on stem-loop or hairpin adapters. Fragments comprising the sequence variant of interest may be circularized by self-circularization of compatible struc- tures on either side of the fragment (which may be the result of adapter ligation or as a result of restriction enzyme digestion of ligated adapters) or circularized by hybridiza- tion to a selector probe that is complementary to the ends of the desired fragment. Extension and a final step of ligation creates a covalently closed circular, optionally double- stranded, polynucleotide.

Sample-Specific Identifier

In an embodiment, the polynucleotide may further com- prise at least one of a sample-specific identifier, an allele- specific identifier and a locus-specific identifier, in addition to a UMI. Hence in an embodiment of the method of the invention, additionally a sample identifier is attached to the polynucleotide.

A sample-specific identifier allows for the pooling of samples prior to sequencing, and subsequently is used to allocate a sequence read to the original sample, and can be applied in different assay types, such as sequencing of fragments or sequencing of ligation products in oligonucle- otide ligation assays. A locus-specific identifier and an allele-specific identifier are typically used in oligonucleotide ligation assays, and trace the sequence back to a specific locus and allele, respectively.

In an embodiment, one of the probes for use in e.g. an OLA assay, may comprise a UMI and another probe may comprise an allele-specific identifier. Alternatively or in addition, one of the probes comprises a UMI as well as an allele-specific identifier.

In addition or alternatively, one of the probes for use in e.g. an OLA assay, may comprise a UMI and another probe may comprise an locus-specific identifier. Alternatively or in addition, one of the probes comprises a UMI as well as a locus-specific identifier.

In addition or alternatively, one of the probes for use in e.g. an OLA assay, may comprise a UMI and another probe may comprise a sample-specific identifier. Alternatively or in addition, one of the probes comprises a UMI as well as a sample-specific identifier.

In addition or alternatively, the probe comprising a locus- specific identifier, and optionally comprising a UMI, further comprises a sample-specific identifier.

In addition or alternatively, the probe comprising an allele-specific identifier, and optionally comprising a UMI, further comprises a sample-specific identifier.

In an embodiment one of the adapters as defined herein comprises a sample-specific identifier. Alternatively or in addition, at least one of the adapters as defined herein comprises a UMI and an sample-specific identifier. Prefer- ably, at least two adapters may be used, wherein a first adapter comprises a UMI and a second adapter comprises a sample-specific identifier. Alternatively, at least the first adapter comprises a UMI and a sample-specific identifier.

Optionally, as further detailed herein, the sample-specific identifier may be located in one or more primers used in the amplification step of the method of the invention. Such one or more primers may in addition or alternatively, comprise a gene or locus identifier, or allele identifier, which traces the sequence back to a specific gene, locus or allele. Preferably, such primer further comprises a sequence that selectively hybridizes to a sequence specific for said gene or locus, or to a sequence specific for said allele, respectively, within the polynucleotide to be amplified.

Amplification and Sequencing

The method of the invention comprises a step of amplifying at least part of the polynucleotides derived from the nucleic acid sample for which the relative frequency of a sequence variant of interest needs to be determined, wherein each polynucleotide comprises a unique molecular index (UMI).

Amplification is well-known in the art and the skilled person knows how to perform an amplification method. A preferred amplification method includes, but is not limited to, a polymerase chain reaction, preferably using a high fidelity polymerase to limit the number of polymerase base substitution errors.

Amplification of the polynucleotides may entail amplification of all polynucleotides derived from the nucleic acid sample. Alternatively, only a part of the polynucleotides is amplified. Preferably, at least those polynucleotides that contain, or are suspected to contain, the sequence variant of interest are amplified in the method of the invention.

Optionally only part of each polynucleotide is amplified. Preferably at least the part of the polynucleotide comprising the UMI is amplified. More preferably, at least the part comprising the UMI and the sequence variant of interest is amplified. Optionally, the whole, or substantially the whole, polynucleotide is amplified. Therefore, within the polynucleotide to be amplified in the method of the invention, at least the UMI is located between a first and a second amplification primer binding site, more preferably the sequence variant of interest and UMI are located in between a first and a second amplification primer binding site. Optionally, the first and second amplification primer binding site is located each at one end of the polynucleotide.

In case the polynucleotide of the method of the invention is a ligation product of at least one oligonucleotide ligation probe for use in e.g. an OLA assay, said probe may comprise an amplification primer binding site. In case at least two or more oligonucleotides ligation probes are used, preferably at least one of the oligonucleotide ligation probes comprises a first amplification primer binding site and another oligonucleotide ligation probe comprises the reversed complement of a second amplification primer binding site, such that, after ligation of the probes, after hybridization to the sequence variant of interest, the ligation product can be amplified using a first and a second amplification primer. Preferably, the OLA assay is performed using an allele-specific probe and a locus-specific probe, that together may be ligated after hybridizing to the sequence variant of interest within the nucleic acid sample of the method of the invention. Preferably, the allele-specific probe comprises a first amplification primer binding site, and the locus-specific probe comprises the reversed complement of a second amplification primer binding site, or vice versa. This primer binding site and respective reversed primer binding site are preferably located at the tail of the probes such that after ligation, the ligation product can be amplified using a first and second amplification primer.

In case the polynucleotide of the method of the invention comprises a nucleic acid fragment of the sample, at least one adapter can be ligated to the nucleic acid fragment as defined herein, wherein the at least one adapter comprises at least a first amplification primer binding site. The first amplification primer binding site is preferably not located in between the UMI and sequence variant of interest, but is located 3' of the UMI and preferably located 3' of both the UMI and the sequence variant of interest. The adapter may comprise the following order of elements: at least a one amplification primer binding site, a UMI, followed by the end of the adapter that can be ligated to respectively the 5' or 3' of the fragment comprising the sequence variant of interest.

Optionally, there is an additional sequencing primer binding site located in between the UMI and a sample specific identifier.

Optionally, a second amplification primer binding site may be located in a second adapter, preferably having a similar order of elements as indicated for the first adapter, wherein preferably the first adapter can be ligated to one end of the fragment and the second adapter can be ligated to the other end of the fragment, rendering a polynucleotide that can be amplified with a first and second amplification primer. Alternatively or in addition, a second amplification primer binding site may be a sequence within the nucleic acid fragment. In this embodiment, there is preferably a selective amplification of the polynucleotide or at least the part of the polynucleotide comprising the sequence variant of interest. Hence in the embodiment wherein the amplification primer binding site is a sequence within the nucleic acid fragment, the amplification primer binding site is preferably located outside the sequence variant of interest.

The skilled person understands that a single type of adapters or a combination of different adapter types may be used in the method of the invention. Preferably at least one of the adapters used in the method of the invention comprises at least one amplification primer binding site, such that at least the polynucleotide and the UMI are amplified.

In addition or alternatively, an adapter may comprise two amplification primer binding sites, e.g. in case the adapter is a Y-shaped adapter wherein a first primer binding site may be located in the bottom strand of the single stranded structure of the Y-shaped adapter, and a reversed complement of a second primer binding site may be located in the top strand of the single stranded structure of the Y-shaped adapter.

The first and second primer, required for amplifying the polynucleotide or part thereof, comprise at their 3' end a sequence that is hybridisable to the amplification primer binding site. At least one of the first primer and the second primer further may comprise a sample-specific identifier and/or sequences that facilitate the deep-sequencing process, preferably at, or close to, the 5' end tail of the primer.

The method of the invention comprises a step of determining the sequences of at least part of the amplified polynucleotides to obtain sequence reads. Therefore, the amplicons resulting from the amplification step of the method of the invention are subjected to sequencing, preferably next-generation sequencing.

The skilled person knows how to perform a next-generation sequencing reaction to obtain sequencing reads of the UMI and sequence variant of interest. Hence, the amplicons may comprise a sequence that is required for or facilitates sequencing e.g. flow cell binding sites such as, but not limited to P5 and P7, for sequencing of at least the UMI and the sequence variant of interest, i.e. denominated herein sequence primer binding sites.

Sequencing may entail sequencing of all amplified polynucleotides derived from the nucleic acid sample. Alternatively, only a part of the amplified polynucleotides is sequenced. Preferably, at least those amplified polynucleotides that contain, or are suspected to contain, the sequence variant of interest are sequenced in the method of the invention.

Optionally only part of each amplified polynucleotide is sequenced. Preferably at least the part of the amplified polynucleotide comprising the UMI is sequenced. More preferably, at least the part comprising the UMI and the sequence variant of interest is sequenced. Optionally, the whole, or substantially the whole, amplified polynucleotide is sequenced.

Optionally, the primer binding sites that served as amplification primer binding sequences in the amplification step may serve as sequence primer binding sequences in the sequencing step. Alternatively, the amplicons comprise sequence primer binding sites separate from the amplification primer binding sites.

Preferably, the sequence primer binding sites are upstream and/or downstream of the UMI and the optional sample-specific identifier, preferably upstream and/or downstream of the UMI and the sequence variant of interest and the optional sample-specific identifier. Preferably, such sequences may be upstream and downstream of, i.e. flank, the UMI, the sequence variant of interest and the optional sample-specific identifier. Hence sequences that facilitate the sequencing process, can be present in at least one of a first and second primer used in the optional amplification step in the method of the invention, in at least one or more oligonucleotide ligation probes for use in e.g. an OLA reaction, and/or in one or more adapters.

In an embodiment, one or more adapters for use in the method of the invention may comprise the following order of elements: at least one amplification primer binding site, a sequencing primer binding site, a UMI, followed by the end of the adapter that can be ligated to respectively the 5' or 3' of the polynucleotide.

In an embodiment, the adapter may comprise the following order of elements: a sequencing primer binding site, a UMI, a sample specific identifier, followed by the end of the adapter that can be ligated to respectively the 5' or 3' of the polynucleotide, wherein optionally, the sequencing primer binding site is preceded by an amplification primer binding site. In another embodiment, the adapter may comprise the following order of elements: a sequencing primer binding site, a sample specific identifier, a UMI, followed by the end of the adapter that can be ligated to respectively the 5' or 3' of the polynucleotide, wherein optionally, the sequencing primer binding site is preceded by an amplification primer binding site.

A sample-specific identifier may be located in one or more oligonucleotide ligation probes for use in e.g. the OLA reaction, or may be located in one or more adapters. Alternatively or in addition, the sample-specific identifier may be located in one or more primers used for amplifying the polynucleotide. Hence, the sample-specific identifier may be located in at least one of the forward or reverse primers used for amplifying the polynucleotide.

In an embodiment, one or more additional adapters can be ligated to the amplified polynucleotide.

The obtained raw sequencing data can be further analysed, e.g. using software available in the art. Sequencing reads having the same UMI should belong to one specific template molecule (i,e, the source DNA molecule). Hence, reads comprising the same UMI can be collapsed into a single "family" of sequence reads, providing for a way to correct for any amplification bias. In addition, this method allows for the correction of sequencing and PCR errors in the individual reads of this "family" to arrive at a highly accurate consensus sequence of the template molecule (comprising the (sequence variant of interest).

Pooling and Multiplexing

It is understood herein that the nucleic acid sample derived from a polyploid organism comprises at least one sequence variant of interest. Put differently, the nucleic acid sample thus may comprise 1, 2, 3, 4, 5, 6, 7, 8, 9, 10 or more sequence variants of interest, such as at least about 50, 100, 150, 200, 250, 300, 350, 400, 450, 500, 750, 1000 or more sequence variants of interest, wherein preferably each sequence variant of interest is an allele. The method of the invention may provide for a simultaneous determination of the relative frequency of these sequences of interest in a nucleic acid sample. The plurality of sequence variants of interest may be two or more variants of the same gene. Alternatively or in addition, the plurality of sequence variants of interest may be sequence variants of different genes in the same nucleic acid sample. Optionally, the method of the invention is multiplexed, i.e. applied simultaneously and in parallel for multiple nucleic acid samples, such as for at least about 10, 20, 30, 40, 50, 60, 70, 80, 90, 100, 500, 1000 or more nucleic acid samples. The method may be performed in parallel for multiple samples.

The multiple samples may be obtainable from different individuals, or the same individual, wherein samples are e.g. obtained at different time points or at different locations (e.g. different tissues) of the same individual.

In addition or alternatively, one or more steps of the method of the invention may be performed on pooled samples. The samples may be tagged prior to pooling the samples, i.e. the samples may comprise a sample-specific identifier prior to pooling. In addition or alternatively, the samples can be pooled using a clever pooling strategy, such as, but not limited to, a 2D and 3D pooling strategy.

Optionally, the method further comprises a step of producing a report indicating the determined relative frequencies of the sequence variant of interest or any further conclusion derived there from. In addition or alternatively, the method may further comprise a step of reporting to a human subject the determined relative frequency of the sequence variant of interest.

Uses

In a second aspect, the invention pertains to the use of a UMI for determining the relative frequency of a sequence variant of interest in a nucleic acid sample derived from at least one polyploid cell.

Preferably, the UMI is located in at least one of: i) an oligonucleotide, preferably an allele-specific oligonucleotide for use in an oligonucleotide ligation assay and ii) an adapter.

In a third aspect, there is therefore also provided for the use of an oligonucleotide ligation probe comprising a UMI for determining the relative frequency of a sequence variant of interest in a nucleic acid sample derived from at least one polyploid cell. Preferably, the oligonucleotide ligation probe is suitable for use in an oligonucleotide ligation assay. Preferably, the oligonucleotide ligation probe is a UMI-comprising oligonucleotide probe as described in the first aspect.

In a fourth aspect, there is provided for the use of an adapter comprising a UMI for determining the relative frequency of a sequence variant of interest in a nucleic acid sample derived from at least one polyploid cell. Preferably, the adapter can be ligated to a fragmented nucleic acid sample as described herein.

Preferably, the adapter is a UMI-comprising adapter as described in the first aspect.

Kit of Parts

In a fifth aspect, the invention concerns a kit of parts, preferably for use in a method as defined herein. The kit of parts may comprise at least one of:

a vial comprising a mixture of oligonucleotide ligation probes suitable for use in an oligonucleotide ligation assay, wherein at least part, optionally all, of the individual oligonucleotide ligation probes comprise a UMI, and wherein preferably the mixture of oligonucleotide probes is specific for one or more alleles. The oligonucleotide ligation probes may further comprise at least one of a primer binding site, an allele-specific identifier and a sample-specific identifier;

a vial comprising a mixture of oligonucleotide ligation probes suitable for use in an oligonucleotide ligation assay, wherein the individual oligonucleotide ligations probes comprise a UMI and wherein preferably the mixture of oligonucleotides is specific for one or more loci. The oligonucleotides may further comprise at least one of a primer binding site, a locus-specific identifier and a sample-specific identifier;

a vial comprising a mixture of oligonucleotides, wherein one part of the mixture comprises oligonucleotide ligation probes specific for one or more alleles, and optionally comprising an allele-specific identifier, and the other part of the mixture comprises oligonucleotide ligation probes specific for one or more loci, and optionally comprising a locus-specific identifier, and wherein the individual allele-specific oligonucleotide ligation probes and/or the individual locus-specific oligonucleotide ligation probes comprise a UMI. Optionally the allele-specific oligonucleotide ligation probes and/or the allele-specific oligonucleotide ligation probes further comprise at least one of a primer binding site and a sample-specific identifier;

a vial comprising a mixture of adapters, wherein the individual adapter molecules comprise a UMI. The adapters may further comprise at least one of a sample identifier and a gene identifier; and a vial comprising one or more amplification primers, preferably an amplification primer as defined herein. Preferably, one of the primers may comprise at least one of a sample-specific identifier and a gene identifier.

Optionally, the oligonucleotides and/or adapters may further comprise one or more primer binding sites.

Preferably, the volume of any of the vials within the kit do not exceed 100 mL, 50 mL, 20 mL, 10 mL, 5 mL, 4 mL, 3 mL, 2 mL or 1 mL.

The reagents may be present in lyophilized form, or in an appropriate buffer. The kit may also contain any other component necessary for carrying out the present invention, such as buffers, pipettes, microtiter plates and written instructions. Such other components for the kits of the invention are known to the skilled person.

Further Aspects

In an aspect, the invention pertains to an oligonucleotide ligation probe, for use in an oligonucleotide ligation assay, wherein the oligonucleotide ligation probe comprises a UMI. Preferably, the oligonucleotide ligation probe is an allele-specific oligonucleotide ligation probe as specified herein above. Preferably, the allele-specific oligonucleotide ligation probe comprises a UMI and a primer binding site. Alternatively or in addition, the oligonucleotide is a locus-specific oligonucleotide ligation probe as specified herein above. Preferably, the allele-specific oligonucleotide ligation probe comprises a UMI and a primer binding site.

In an aspect, the invention further concerns a composition comprising a mixture of oligonucleotide ligation probes, preferably for use in an oligonucleotide ligation assay, wherein at least part of, optionally all, oligonucleotide ligation probes comprise a UMI. This mixture of oligonucleotide ligation probes may comprise one or more subsets of probes wherein the probes within each subset that have the same sequence with exception to the UMI. In other words, the probe sequences of a subset only differ in the sequence of their UMIs. Optionally, the probes between the different subsets differ in sequence for annealing. Optionally said sequence is for annealing to different loci.

Optionally, the oligonucleotide ligation probes of the one or more subsets are allele-specific oligonucleotide ligation probes. The allele-specific oligonucleotide ligation probes in a subset anneal to the same allelic variant. Optionally, a composition comprises multiple subsets of allele-specific oligonucleotide ligation probes, wherein the probes of the different subsets anneal to different allelic variants of the same locus. Alternatively or in addition, the allele-specific oligonucleotide ligation probes of different subsets anneal to an allelic variant at different loci. Alternatively or in addition, the composition may further comprise one or more locus-specific oligonucleotide ligation probes. Preferably, the one or more locus-specific oligonucleotide ligation probes within the composition can be used together with one or more allele-specific oligonucleotide ligation probes of the composition in an OLA assay as described herein.

Preferably, the oligonucleotide ligation probes comprise a primer binding site. The primer binding site may be identical for all allele-specific oligonucleotide ligation probes present in the composition. Alternatively or in addition, the primer binding site may be identical for all locus-specific oligonucleotide ligation probes present in the composition. Alternatively, a combination of primer binding sites may be used, e.g. depending on the allelic variant and/or locus.

The invention further pertains to a method for genotyping a sequence variant of interest in a nucleic acid sample derived from at least one polyploid cell, wherein the method comprises steps a)-f) as defined herein.

The invention further concerns a method for determining one or more allele ratios in a nucleic acid sample derived from at least one polyploid cell, wherein the method comprises steps a)-f) as defined herein.

The invention further relates to a method for determining one or more allele frequencies in a nucleic acid sample derived from at least one polyploid cell, wherein the method comprises steps a)-f) as defined herein.

The invention further pertains to a report mentioning the relative frequency of a sequence variant of interest in a nucleic acid sample derived from at least one polyploid cell, wherein the relative frequency is determined by a method as defined herein.

FIGURE LEGEND

Figure 1:
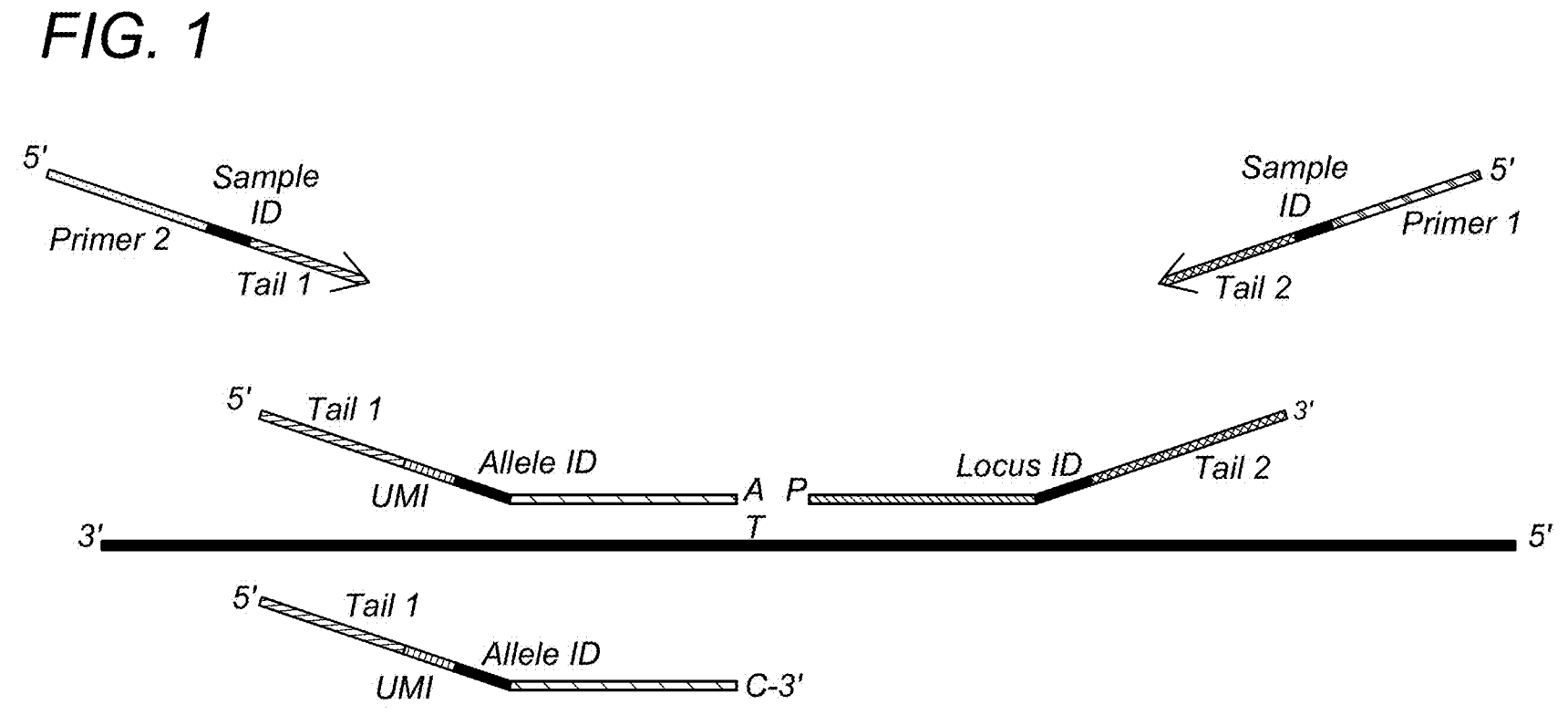

FIG. 1: Exemplary oligonucleotide probe design for an oligonucleotide ligation assay (OLA) using a UMI.

FIGS. 2A-2B: Exemplary adapter design for next-generation sequencing using a UMI. FIG. 2A is an exemplary rare cutter adapter design with UMI and FIG. 2B is an exemplary frequent cutter adapter design with UMI.

Figures 3A, 3B, 3C, 3D:
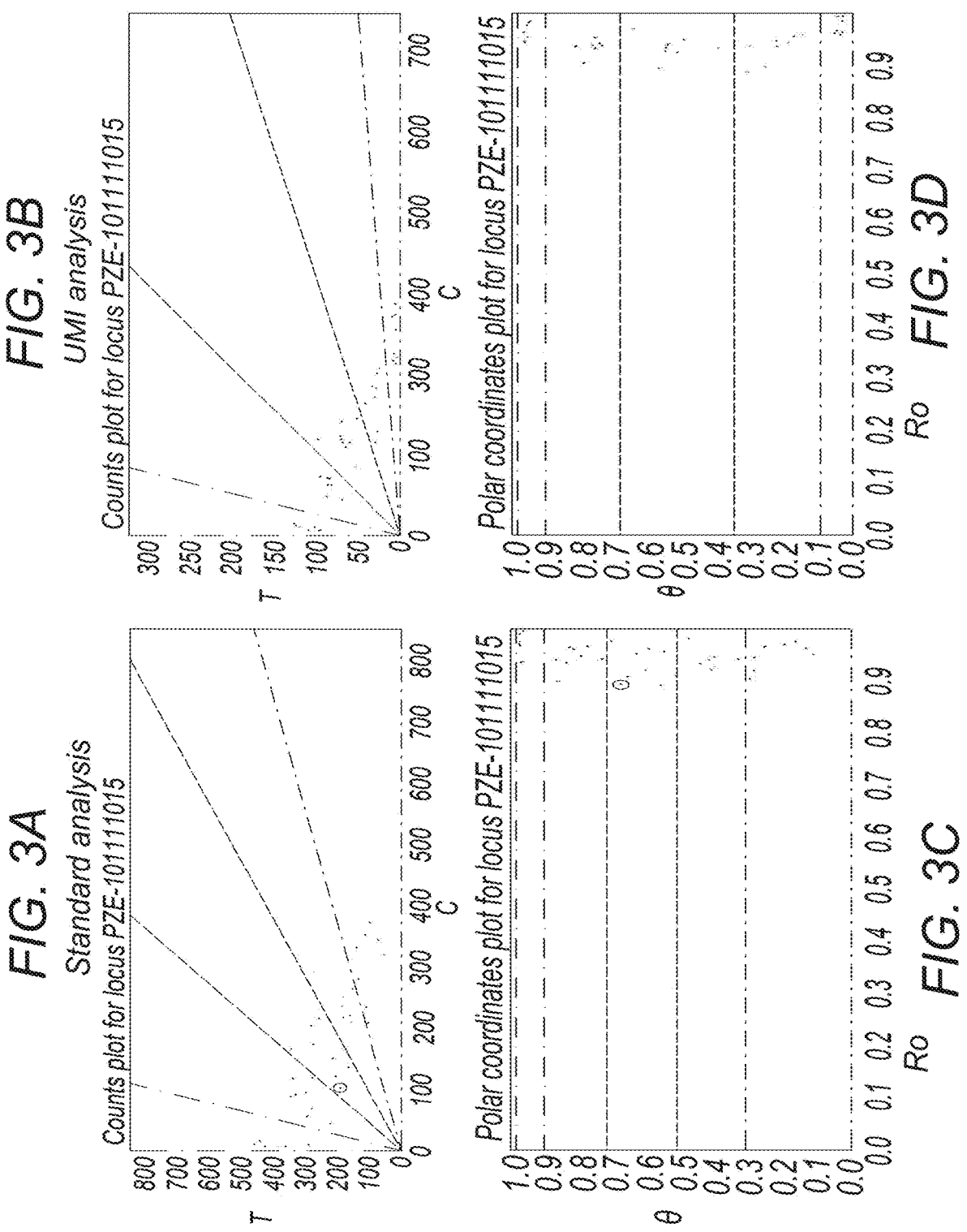

FIGS. 3A-3E: overview of the analysis results for a single locus (detectable using the locus probe of SEQ ID NO: 149, the first allele probe of SEQ ID NO: 475 and the second allele probe of SEQ ID NO: 801) using either standard analysis (FIGS. 3A and 3C) and using the UMI information (FIGS. 3B and 3D). The base calling using a standard analysis was incorrect in two instances (see arrows, FIG. 3E). When including the UMI information in the analysis, there was no discrepancy between the expected and called alleles.

The invention is explained in Example 1, 2 and 3 with reference to FIGS. 1, 2A, 2B, 3A, 3B, 3C, 3D and 3E.

Example 1

UMIs can be implemented in oligonucleotide ligation (OLA)/genotyping assays for polyploid cells e.g. through the addition of random DNA sequences just before and/or after the Allele Specific Identifier present in the Allele Specific probe. Furthermore, addition of UMIs is possible in the Locus Specific Probe or in both probes. An example of the probe design, including the UMI in the Allele Specific probe, is outlined in FIG. 1.

Example 2

Application of UMIs in next-generation sequencing and genotyping of polyploid cells can be implemented through addition of UMIs in e.g. the rare cutter adapter sequence used for sequence-based genotyping. An outline of a rare cutter adapter including a UMI is presented in FIGS. 2A and 2B. UMIs might also be added to the P7 adapter, e.g. if a non-selective amplification is used after adapter ligation. For this, the P7 adapter can be designed to comprise the UMI and a sequencing primer sequence, followed by the overhang specific for the restriction endonuclease used. Such adapter is compatible with paired end sequencing of the amplification products.

Example 3

Validation of Oligonucleotide Probes with UMIs

An experiment was performed using UMI-comprising oligonucleotide ligation probes. Analysis was subsequently performed with and without use of the UMI information.

Oligonucleotides were designed to detect 326 different SNPs in the maize genome (*Zea mays*), each having 2 alleles (i.e. 326-plex), in an OLA assay. The probes were produced and used for genotyping different genomic maize DNA samples. Two sets of homozygous diploid germplasm lines were mixed in varying amounts to mimic tetraploid genomic samples. Set 1 consisted of germplasm lines PH207 (P1) and CO125 (P2), whereas set 2 consisted of the germplasm lines B73 (P3) and Mo17 (P4). These germplasm lines are available at U.S. National Plant Germplasm System (https://npgsweb.ars-grin.gov/gringlobal/search.aspx?). The ratios in which DNA of the germplasm lines were mixed is shown in table 1 and 2.

TABLE 1

| P1 and P2 mixing ratios | | | |
|---|---|---|---|
| RATIO | | | |
| P1 | P2 | ng P1 | ng P2 |
| 4 | 0 | 100 | 0 |
| 3 | 1 | 75 | 25 |
| 2 | 2 | 50 | 50 |
| 1 | 3 | 25 | 75 |
| 0 | 4 | 0 | 100 |

TABLE 2

| P3 and P4 mixing ratios | | | |
|---|---|---|---|
| RATIO | | | |
| P3 | P4 | ng P3 | ng P4 |
| 4 | 0 | 100 | 0 |
| 3 | 1 | 75 | 25 |
| 2 | 2 | 50 | 50 |
| 1 | 3 | 25 | 75 |
| 0 | 4 | 0 | 100 |

Reproducibility of OLA assays using the probes produced was tested by comparing the genotype calling between duplicates of each of the different maize genomic DNA sample mixes. Additionally, genotype calls obtained from OLA assays using the probes were validated by comparing the genotype calling within these different maize genomic DNA sample mixes, wherein the data is analyzed using the standard data analysis, or preprocessed using the UMI information which is present in the probes, to count the number of ligated probe molecules and thereby the number of template molecules.

The oligonucleotide probes were designed using common procedures based on the known sequence of the loci, and selected to discriminate the SNP alleles for each of the 326 loci.

The sequences of the locus probes are shown in SEQ ID NOs: 1-326. The sequences of the allele 1 UMI-comprising probes and the allele 2 UMI-comprising probes are shown in respectively SEQ ID NOs: 327-652 and SEQ ID NOs: 653-978 (5'-3' orientation). The allele 1 and allele 2 probes without an UMI are identical to SEQ ID NOs: 327-978, with the exception that after the first 29 nucleotides, the 6 nt UMI (annotated in the sequences as nnnnnn, wherein n is any one of a, g, c or t) was excluded from the sequence.

PCR primer binding regions, UMIs, locus and allele identifiers were included. Adjacent to the 5' end of the allele-specific probe sequence are the following elements (in the 5' to 3' direction): a universal sequence of 29 nucleotides, a 6 nt UMI (NNNNNN), a 4-nt allele identifier, and a first target-specific sequence. Adjacent to the 5' end of the locus-specific probe sequence are the following elements (in the 3' to 5' direction): a universal sequence of 31 nucleotides, an 8-nt locus identifier, and a second target specific sequence.

Below, the procedure of an OLA assay is outlined using probes as described above.

The total amount of probes of the 326 loci used per OLA reaction is 1 μl of a 1.304 μM mixture containing 4 nM of probes per locus, being 1 nM of each of the two allele-specific probes and 2 nM of the locus-specific probe.

OLA Assay Procedure

Ligation reactions were prepared as follows: 100 ng (mixed) genomic DNA in 5 μL was combined with 1 μl 10×Taq DNA Ligase Buffer (200 mM Tris-HCl PH 7.6, 250 mM KAc, 100 mM MgAc, 10 mM NAD, 100 mM Dithiothreitol, 1% Triton-X100), 4 units Taq DNA ligase (New England BioLabs), 1 μl 326-plex-probe mix (with or without UMI) (4 nM per locus; 1.304 UM total). Ligation reactions were setup in duplicate per mixed genomic DNA sample. The reaction mixtures was incubated for 1 minute and 30 seconds at 94° C. followed by a temperature decrease of 1.0° C. per 30 seconds until 60° C., followed by an incubation at 60° C. for approximately 18 hours. Reactions were kept at 4° C. until further use. Ligation reactions were diluted 4× with MilliQ water.

Amplification of the ligation products was performed using a first and second amplification primer. The first amplification primer is designed to comprise at its 3' terminus a sequence (16 nucleotides) for annealing to the first primer binding sequence, a P7 sequence located at its 5' terminus, and in between these elements a 5-nt sample identifier. The second primer was designed to comprise at its 3' terminus a sequence (18 nucleotides) for annealing to the second primer binding sequence, a P5 sequence located at its 5' terminus, and between these elements a 6-nt plate identifier.

Amplification of the ligation products was carried out in the following reaction mixture: 10 μl 4× diluted ligation reaction, 0.05 μM (end concentration) of each primer (first and second amplification primer), 20 μL of Phusion Hot Start FLX 2× master mix (Bioké) and MilliQ water to a total of 40 μl. Each ligation product was amplified two times; in total PCRs were performed. The thermocycling profile was performed on a PE9700 (Perkin Elmer Corp.) with a gold or silver block using the following conditions: Step 1: Pre PCR incubation: 30 seconds at 98° C. Step 2: Denaturation: 10 seconds at 98° C.; Annealing: 15 seconds at 65° C.; Extension: 15 seconds at 72° C. Total cycle number was 29. Step 3: Extension 5 minutes at 72° C. Reactions were kept at 4° C. until further use. Amplification products of the in total 40 PCR reactions were pooled (40×40 μl) and purified using four PCR purification columns (Qiagen) and eluted in 15 μl MilliQ water per column, 60 μL total.

Purification of the amplicons was done with a Pippin Prep of Sage Science. Four times 900 ng was purified using a 3% cassette and marker C with no overflow. The range 170 bp until 230 bp was eluted. The eluted product were purified using the Minelute kit (Qiagen) and eluted in 15 μL Elution Buffer (10 mM Tris-Cl pH8.5).

Sequencing of the amplicons was performed on an Illumina HiSeq2500. Sequencing data were de-multiplexed, with reads assigned to each of the samples used. Data from each sample of the genomic DNA mixes used were further processed. Processing was performed either using the standard analysis process, or with a pre-analysis step that took into account the UMI information present in each read of the sequencing run. In the analysis process genotypes calling was performed which takes allele dosage for a tetraploid genome into account, i.e. allele dosage classes discriminated were 4:0 (A), 3:1 (D), 2:2 (H), 1:3 (C) and 0:4 (B).

Purification of the amplicons was done with a Pippin Prep from Sage Science. Four times 900 ng was purified using a 3% cassette and marker C with no overflow. The range 170 bp until 230 bp was eluted. The eluted product were purified using the Minelute kit (Qiagen) and eluted in 15 μL Elution Buffer (10 mM Tris-Cl pH8.5).

Sequencing of the amplicons was performed on an Illumina HiSeq2500. Sequencing data were de-multiplexed, with reads assigned to each of the samples used. Data from each sample of the genomic DNA mixes used were further analysed. Processing was performed using either the standard analysis process, or with an analysis that took into account the UMI information present in each read of the sequencing run. In the standard analysis process the combination of, and the distance between, the Locus and Allele identifier sequence was used to assign a sequence read from each sample to a certain locus-allele combination. The analysis that took the UMI information into account, selected only a single count for each locus-allele specific combination that was found more than once with the same UMI, to provide an universal count of the number of sample molecules for every SNP allele. Genotype calling took the expected allele dosage for a tetraploid genome into account, i.e. that the defined allele dosage classes were 4:0 (A), 3:1 (D), 2:2 (H), 1:3 (C) and 0:4 (B).

Results

For the 40 samples (comprising a total theoretical number of 40×326=13040 genotypes), a total of 12716 genotypes were called, when the data set was analyzed without taken the UMI information into account. When using the UMI information, a total of 12585 genotypes were called.

Analysis of the called genotypes showed that when the UMI information was taken into consideration, the correlation between the expected and called alleles was respectively 98.0% and 97.6% (experiment performed in duplicate). Strikingly, the correlation between the expected and called alleles was substantially lower when the UMI information was disregarded, i.e. 94.6% and 94.5%.

FIGS. 3A-3E shows an overview of the analysis results for a single locus (detectable using the locus probe of SEQ ID NO: 149, the first allele probe of SEQ ID NO: 475 and the second allele probe of SEQ ID NO: 801) using both data processing methods. When taking the UMI information into account, samples in the same genotype class clustered more tightly. As shown in FIGS. 3A-3E, alleles were correctly called when taking the UMI information into account, while there was a discrepancy between the expected and called alleles when the UMI information was disregarded.

The invention claimed is:

1. A method for determining the genotype of a polyploid cell by determining the relative frequency of an allelic variant of interest in a nucleic acid sample, wherein the nucleic acid sample comprises genomic DNA derived from the polyploid cell, wherein the method comprises:

(a) providing polynucleotides derived from the nucleic acid sample, wherein the polynucleotides comprise the sequence of the allelic variant of interest or the reversed complement thereof, and wherein each polynucleotide comprises a unique molecular index (UMI), (b) amplifying the polynucleotides provided in (a);

(c) determining the sequences of the amplified polynucleotides to obtain sequence reads;

(d) grouping the sequence reads using at least the UMI and obtaining a consensus sequence of the grouped sequence reads; and (e) determining the genotype of the polyploid cell by calculating the number of times the allelic variant of interest occurs in the nucleic acid sample in relation to the total of the number of times all allelic variants thereof occur in the nucleic acid sample.

2. The method according to claim 1, wherein the polynucleotides of (a) are at least one of:

(i) fragments of nucleic acids from the sample, wherein each fragment is attached to a UMI; and (ii) ligation products of probes capable of hybridizing to the allelic variant of interest in a nucleic acid from the sample, wherein each ligation product comprises a UMI.

3. The method according to claim 1, wherein (d) comprises collapsing sequence reads obtained in (c).

4. The method according to claim 1, wherein the allelic variant is present on a single locus.

5. The method according to claim 1, wherein the method is preceded by determining the ploidy level of the at least one polyploid cell.

6. The method according to claim 1, wherein the relative frequency of two or more allelic variants of interest is determined.

7. The method according to claim 2, wherein the polynucleotides are ligation products, and wherein the UMI is present in an allele-specific oligonucleotide ligation probe.

8. The method according to claim 1, wherein prior to sequencing (c), the polynucleotides or amplified polynucleotides are enriched.

9. The method according to claim 8, wherein polynucleotides or amplified polynucleotides are enriched using a hybridization-based capture method.

10. The method according to claim 1, wherein the polynucleotides further comprise a sample identifier.

11. The method according to claim 2, wherein the polynucleotides are fragments, and wherein at least a first adapter is ligated to the fragments and wherein the UMI is located in the first adapter, wherein optionally a second adapter is ligated to the fragment.

12. The method according to claim 11, wherein a sample identifier is present in the first or optional second adapter.

13. The method according to claim 1, wherein the method is multiplexed.

\* \* \* \* \*